(12) United States Patent
Xia et al.

(10) Patent No.: US 9,156,870 B2
(45) Date of Patent: Oct. 13, 2015

(54) PHOSPHORESCENT EMITTERS

(75) Inventors: Chuanjun Xia, Lawrenceville, NJ (US); Dinesh Rayabarapu, Overland Park, KS (US); Yonggang Wu, Hunan (CN); Suman Layek, Lawrenceville, NJ (US); James Fiordeliso, Yardley, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 435 days.

(21) Appl. No.: 12/712,802

(22) Filed: Feb. 25, 2010

(65) Prior Publication Data

US 2011/0204333 A1    Aug. 25, 2011

(51) Int. Cl.
*H01L 51/54* (2006.01)
*C09K 11/06* (2006.01)
*C07F 15/00* (2006.01)
*H01L 51/00* (2006.01)
*H01L 51/50* (2006.01)

(52) U.S. Cl.
CPC ........ *C07F 15/0033* (2013.01); *H01L 51/0085* (2013.01); *C09K 11/06* (2013.01); *C09K 2211/1044* (2013.01); *C09K 2211/185* (2013.01); *H01L 51/0072* (2013.01); *H01L 51/0074* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |

(Continued)

FOREIGN PATENT DOCUMENTS

| | | |
|---|---|---|
| CN | 101525354 | 9/2009 |
| EP | 0650955 | 5/1995 |

(Continued)

OTHER PUBLICATIONS

Kuwabara, Yoshiyuki et al., "Thermally Stable Multilayered Organic Electroluminescent Devices Using Novel Starburst Molecules, 4,4',"-Tri(*N*-carbazolyl)triphenylamine (TCTA) and 4,4',4"-Tris(3-methylphenylphenyl-amino)triphenylamine (*m*-MTDATA), as Hole-Transport Materials," *Adv. Mater*, 6(9):677-679 (1994).

(Continued)

*Primary Examiner* — Marie R. Yamnitzky
(74) *Attorney, Agent, or Firm* — Duane Morris LLP

(57) ABSTRACT

Compounds including a ligand with a dibenzo-fused 5-membered ring substituent are provided. In particular, the compounds may be iridium complexes including imidazole coordinated to the dibenzo-substituted ligand. The dibenzo-fused 5-membered ring moiety of the ligand may be twisted or minimally twisted out of plane with respect to the rest of the ligand structure. The compound may be used in organic light emitting devices, particularly as emitting dopants in blue devices. Devices comprising the compounds may demonstrate improved stability while maintaining excellent color.

21 Claims, 3 Drawing Sheets

(56) References Cited

U.S. PATENT DOCUMENTS

| | | |
|---|---|---|
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 6,936,716 B1 | 8/2005 | Lin |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0088167 A1 | 4/2007 | Lin et al. |
| 2007/0190359 A1 | 8/2007 | Knowles et al. |
| 2007/0196691 A1* | 8/2007 | Ikemizu et al. ............... 428/690 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0066226 A1* | 3/2009 | Sugita et al. ............... 313/504 |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0200927 A1 | 8/2009 | D'Andrade et al. |
| 2009/0243479 A1 | 10/2009 | Tanaka et al. |
| 2012/0037889 A1 | 2/2012 | Tanaka et al. |

FOREIGN PATENT DOCUMENTS

| | | |
|---|---|---|
| EP | 1725079 | 11/2006 |
| EP | 1988143 | 11/2008 |
| EP | 2034538 | 3/2009 |
| EP | 2066150 | 6/2009 |
| JP | 200511610 | 1/2005 |
| JP | 2007123392 | 5/2007 |
| JP | 2007254297 | 10/2007 |
| JP | 2008074939 | 10/2009 |
| JP | 2010-118381 | 5/2010 |
| JP | 2010-135467 | 6/2010 |
| TW | I237524 | 8/2005 |
| TW | 200907018 | 2/2009 |
| TW | 200925150 | 6/2009 |
| TW | 200948183 | 11/2009 |
| WO | WO 01/39234 | 5/2001 |
| WO | WO 02/02714 | 1/2002 |
| WO | WO 02/15645 | 2/2002 |
| WO | WO 03/040257 | 5/2003 |
| WO | WO 03/060956 | 7/2003 |
| WO | WO 2004/093207 | 10/2004 |
| WO | WO 2004/107822 | 12/2004 |
| WO | WO 2005/014551 | 2/2005 |
| WO | WO 2005/019373 | 3/2005 |
| WO | WO 2005/030900 | 4/2005 |
| WO | WO 2005/089025 | 9/2005 |
| WO | WO 2005/123873 | 12/2005 |
| WO | WO 2006/009024 | 1/2006 |
| WO | WO 2006/056418 | 6/2006 |
| WO | WO 2006/072002 | 7/2006 |
| WO | WO 2006/082742 | 8/2006 |
| WO | WO 2006/098120 | 9/2006 |
| WO | WO 2006/100298 | 9/2006 |
| WO | WO 2006/103874 | 10/2006 |
| WO | WO 2006/114966 | 11/2006 |
| WO | WO 2006/132173 | 12/2006 |
| WO | WO 2007/002683 | 1/2007 |
| WO | WO 2007/004380 | 1/2007 |
| WO | WO 2007/063754 | 6/2007 |
| WO | WO 2007/063796 | 6/2007 |
| WO | WO 2007/108362 | 9/2007 |
| WO | WO 2007/108459 | 9/2007 |
| WO | WO 2008/056746 | 5/2008 |
| WO | WO 2008/101842 | 8/2008 |
| WO | WO 2008/132085 | 11/2008 |
| WO | WO 2008/140657 | 11/2008 |
| WO | WO 2009/000673 | 12/2008 |
| WO | WO 2009/003898 | 1/2009 |
| WO | WO 2009/008311 | 1/2009 |
| WO | WO 2009/018009 | 2/2009 |
| WO | WO 2009/021126 | 2/2009 |
| WO | WO 2009/050290 | 4/2009 |
| WO | 2009060779 | 5/2009 |
| WO | WO 2009/062578 | 5/2009 |
| WO | WO 2009/063833 | 5/2009 |
| WO | WO 2009/066778 | 5/2009 |
| WO | WO 2009/066779 | 5/2009 |
| WO | WO 2009/073246 | 6/2009 |
| WO | WO 2009/086028 | 7/2009 |
| WO | WO 2009/100991 | 8/2009 |
| WO | 2009107497 | 9/2009 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral $Ru^{II}$ PHosphorescent Emitters," *Adv. Mater.*, 17(8):1059-1064 (2005).

Huang, Jinsong et al., "Highly Efficient Red-Emission Polymer Phosphorescent Light-Emitting Diodes Based on Two Novel Tris(1-phenylIsoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

(56) References Cited

OTHER PUBLICATIONS

Tang, C.W. and VanSlyke, S.A., "Organic Electroluminescent Diodes," *Appl. Phys. Lett.*, 51(12):913-915 (1987).
Adachi, Chihaya et al., "Organic Electroluminescent Device Having a Hole Conductor as an Emitting Layer," *Appl. Phys. Lett.*, 55(15):1489-1491 (1989).
Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).
Gao, Zhiqiang et al., "Bright-Blue Electroluminescence From a Silyl-Substituted ter-(phenylene-vinyiene) derivative," *Appl. Phys. Lett.*, 74(6):865-867 (1999).
Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).
Hung, L.S. et al., "Anode Modification in Organic Light-Emitting Diodes by Low-Frequency Plasma Polymerization of $CHF_3$," *Appl. Phys. Lett.*, 78(5):673-675 (2001).
Ikai, Masamichi et al, "Highly Efficient Phosphorescence From Organic Light-Emitting Devices with an Exciton-Block Layer," *Appl. Phys. Lett.*, 79(2):156-158 (2001).
Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Nighty Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett.*, 78(11):1622-1624 (2001).
Wong, Keith Man-Chung et al.,"A Novel Class of Phosphorescent Gold(III) Alkynyl-Based Organic Light-Emitting Devices with Tunable Colour," *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota, Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).
Sakamoto, Youichi et al., "Synthesis, Characterization, and Electron-Transport Property of Perfluorinated Phenylene Dendrimers," *J. Am. Chem. Soc.*, 122(8)1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al., 1,2,4-Triazole Derivative as an Electron Transport Layer in Organic Electroluminescent Devices, *Jpn. J. Appl. Phys.*, 32:L917-L920 (1993).
Van Slyke, S. A. et al., "Organic Electroluminescent Devices with Improved Stability," *Appl. Phys. Lett.*, 69(15 ):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based on Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes of Poly(3-Hexylthiophene): Electro-Optical Characteristics Related to Structure," *Synthetic Metals*, 88:171-177 (1997).
Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).
Salbeck, J. et al., "Low Molecular Organic Glasses for Blue Electroluminescence," *Synthetic Metals*, 91:209-215 (1997).
Baldo et al., "Highly Efficient Phosphorescent Emission from Organic Electroluminescent Devices," Nature, vol. 395, 151-154, (1998).
Baldo et al., "Very high-efficiency green organic light-emitting devices based on 1 electrophosphorescence," Appl. Phys. Lett., vol. 75, No. 1, 4-6 (1999).
The Search/Examination report corresponding to the PCT/US11/25807 application, (dated Apr. 29, 2011).
Notice of Reasons for Rejection dated Sep. 29, 2014 issued for corresponding Japanese Patent Application No. 2012-555090.
Office Action issued on Oct. 27, 2014 in corresponding Chinese Application No. 201180010862.7.

* cited by examiner

PHOSPHORESCENT EMITTERS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention relates to phosphorescent organic materials containing a ligand with a dibenzo-fused 5-membered ring substituent and devices containing these compounds.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

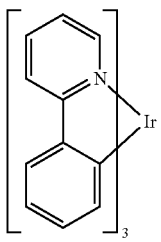

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

The compounds provided herein comprising a ligand L having the formula:

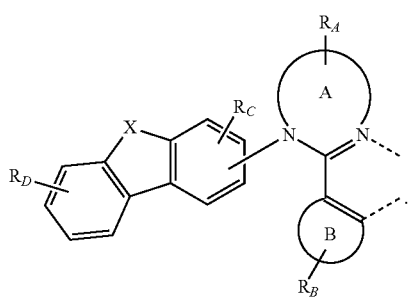

Formula I

A and B are each independently a 5-membered or 6-membered carbocyclic or heterocyclic ring. Preferably, B is phenyl. $R_A$, $R_B$, $R_C$, and $R_D$ represent mono, di, tri, or tetra substitutions. $R_A$, $R_B$, $R_C$, and $R_D$ are independently selected from hydrogen, halogen, alkyl, alkoxy, amino, alkenyl, alkynyl, aryl and heteroaryl. $R_A$, $R_B$, $R_C$, and $R_D$ are optionally fused. X is selected from the group consisting of CRR', NR, O, and S. R and R' are independently selected from the group consisting of alkyl and aryl. The ligand L is coordinated to a metal M having an atomic number greater than 40. Preferably, M is Ir.

In one aspect, the compound is homoleptic. Examples of homoleptic compounds include, without limitation, Compounds 1-72 and Compounds 83-114.

In another aspect, the compound is heteroleptic and all of the ligands L in the compound have Formula I. In yet another aspect, the compound is heteroleptic and at least one of the ligands L in the compound have Formula I.

In one aspect, $R_C$ is two alkyl substituents. In another aspect, $R_C$ is two alkyl substituents having 3 or more carbon atoms.

The ring containing $R_C$ may have further substitutions at the positions ortho to the carbon atom connected to A. In one aspect, the ring containing $R_C$ is substituted at one of the positions ortho to the carbon atom connected to A. In another aspect, the ring containing $R_C$ has two substituents located at the positions ortho to the carbon atom connected to A. In a further aspect, the ring containing $R_C$ has one substituent that is located at a position ortho to the carbon atom attached to A and the other position ortho to the carbon atom attached to A is occupied by the substituted dibenzo moiety.

In one aspect, $R_C$ is hydrogen.

In one aspect, the compound is selected from the group consisting of Compound 1-Compound 114.

In one aspect, $R_A$ is fused to A. Preferably, $R_A$ is an aryl or heteroaryl. More preferably, $R_A$ is imidazole.

Compounds including a dibenzo-substituted benzimidazole ligand include compounds selected from the group consisting of Compound 37-Compound 72.

In one aspect, the compound comprises a ligand L wherein X is O. Compounds comprising a dibenzofuran ligand include compounds selected from the group consisting of Compound 1-Compound 48.

In one aspect, the compound comprises a ligand L wherein X is S. Compounds comprising a dibenzothiophene ligand include compounds selected from the group consisting of Compound 13-Compound 60.

In one aspect, the compound comprises a ligand L wherein X is NR. Compounds comprising a carbazole ligand include compounds selected from the group consisting of Compound 25-Compound 72.

A first device comprising an organic light emitting device is also provided. The organic light emitting device further comprises an anode, a cathode, and an organic layer, disposed between the anode and the cathode, the organic layer comprising a compound comprising a ligand L having Formula I, as discussed above. Selections for the substituents described as preferred for the compound including the ligand L having Formula I are also preferred for use in a device that comprises a compound including a ligand L having Formula I. These selections include those described for B, M, $R_C$, $R_A$, and X.

A and B are each independently a 5-membered or 6-membered carbocyclic or heterocyclic ring. Preferably, B is phenyl. $R_A$, $R_B$, $R_C$, and $R_D$ represent mono, di, tri, or tetra substitutions. $R_A$, $R_B$, $R_C$, and $R_D$ are independently selected from hydrogen, halogen, alkyl, alkoxy, amino, alkenyl, alkynyl, aryl and heteroaryl. $R_A$, $R_B$, $R_C$, and $R_D$ are optionally fused. X is selected from the group consisting of CRR', NR, O, and S. R and R' are independently selected from the group consisting of alkyl and aryl. The ligand L is coordinated to a metal M having an atomic number greater than 40. Preferably, M is Ir.

In one aspect, the first device is a consumer product. In one particular aspect, the first device is an organic light emitting device. In another particular aspect, the first device is a display.

In one aspect, the compound is homoleptic. In another aspect, the compound is heteroleptic and all of the ligands L in the compound have Formula I. In yet another aspect, the compound is heteroleptic and at least one of the ligands L in the compound have Formula I.

In one aspect, $R_C$ is two alkyl substituents. In another aspect, $R_C$ is two alkyl substituents having 3 or more carbon atoms.

In one aspect, the ring containing $R_C$ is substituted at both positions ortho to the carbon atom connected to A.

In one aspect, $R_C$ is hydrogen.

Particular devices are provided wherein the devices include a compound selected from the group consisting of Compound 1-Compound 114.

Additionally, devices are provided wherein the organic layer is an emissive layer and the compound comprising a ligand L having Formula I is an emitting dopant. Moreover, the organic layer further comprises a host. Preferably, the host has the formula:

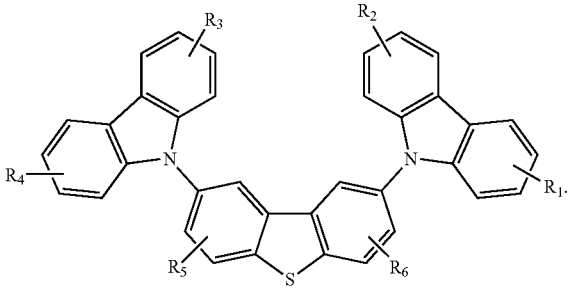

Formula II $R_1$, $R_2$, $R_3$, $R_4$, $R_5$, and $R_6$ are independently selected from the group consisting of hydrogen, alkyl and aryl.

Most preferably, the host is H1.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
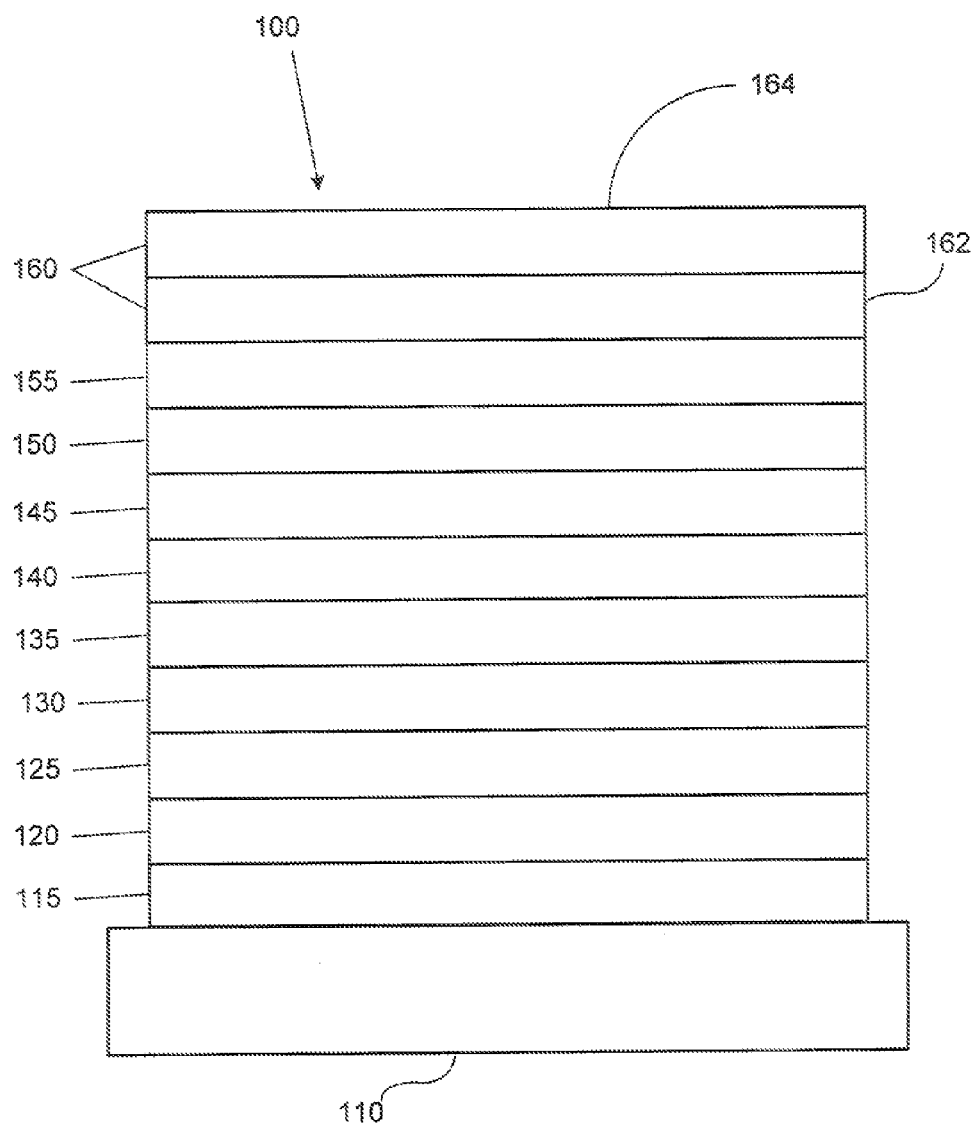
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
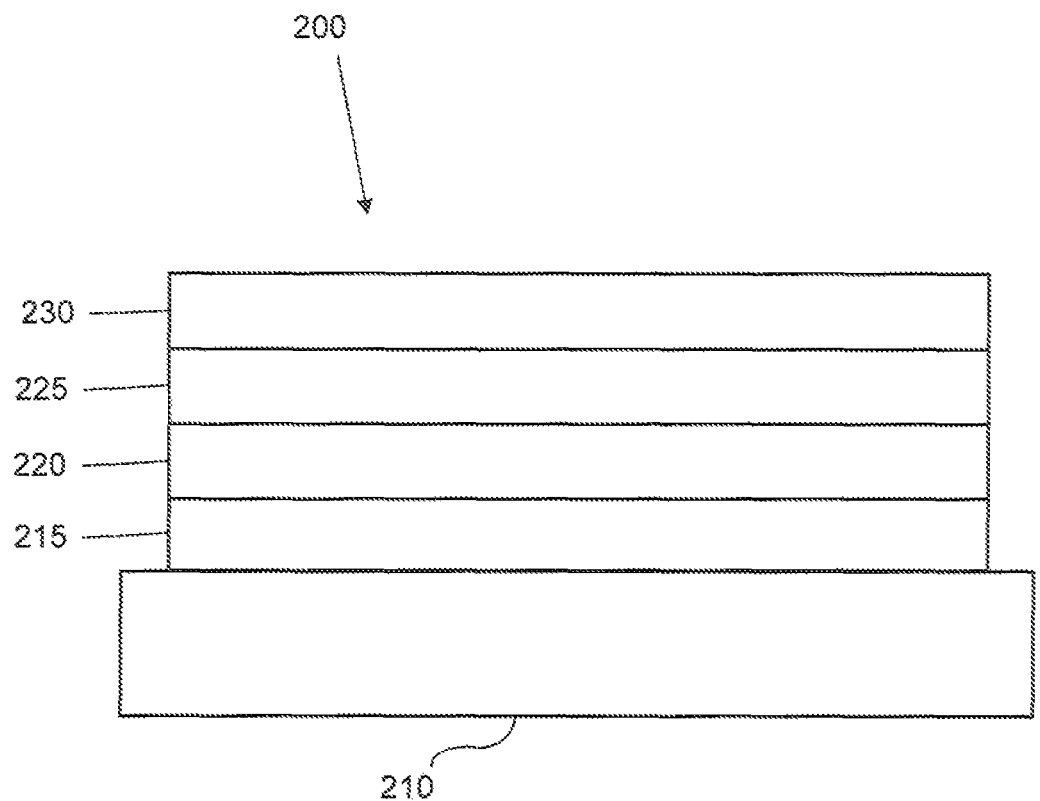
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
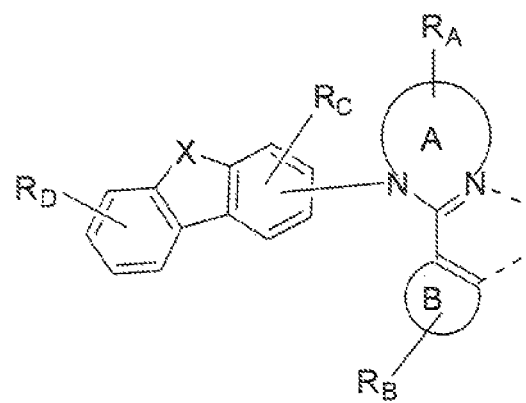
FIG. 3 shows a ligand with a dibenzo-fused 5-membered ring substituent.

Novel compounds including a ligand with a dibenzo-fused 5-membered ring substituent are provided (illustrated in FIG. 3). In particular, the dibenzo-fused 5-membered ring substituents on the ligand include dibenzothiophene, dibenzofuran, carbazole, and fluorene ligands. The dibenzo-fused 5-membered ring substituent is twisted or minimally twisted out of plane with respect to the cyclometalling moiety of the ligand. These compounds may demonstrate particularly beneficial properties, and may be advantageously used in organic light emitting devices.

When two aromatic carbocyclic and/or heterocyclic rings are connected, the two rings may twist out of plane with respect to each other. For example, Formula I shows a structure containing two rings, ring Y and ring Z, that may twist out of plane with respect to one another.

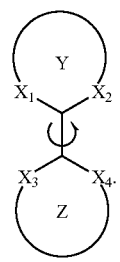

Formula I

The dihedral angle can be small, such as about 0° to about 40°. For example, biphenyl has two phenyl rings that are connected to each other and the dihedral angle is about 40°. In the previous example, the dihedral angle may be less than or about 40° if one or both of ring Y and ring Z is a 5-membered ring, or if one or more of $X_1$-$X_4$ is N instead of C—H. The dihedral angle has a significant effect on the conjugation between the two aromatic rings. It is believed that the two rings in biphenyl are fully conjugated to each other. As used herein, minimally twisted is defined as a dihedral angle between 0° to 40°, and twisted is defined as a dihedral angle is between 41°-90°.

Organometallic compounds with a twisted aryl substituent have been reported in the literature (see US20070088167 and US20060251923). However, the compounds provided herein contain novel structures and demonstrate improved properties. The compounds herein comprise a ligand with a dibenzo-fused 5-membered ring substituent in which the dibenzo-fused 5-membered ring substituent may be twisted or minimally twisted with respect to the plane of the A ring. The dibenzo-fused 5-membered ring substituent may be twisted out of plane with respect to the A ring by the addition of bulky substituents at one or more of the positions ortho to the point of attachment between the dibenzo-fused 5-membered ring substituent and the rest of the ligand, i.e., the A ring. The addition of a bulky substituent at one ortho position may twist the dibenzo-fused 5-membered ring substituent to some extent, and decrease the conjugation between the A ring and the dibenzo-fused 5-membered ring substituent. Bulky substituents at both ortho positions will disrupt the conjugation completely, i.e., a dihedral angle close of 90°.

Compounds including a ligand with a twisted dibenzo-fused 5-membered ring substituent may have improved properties. Without being bound by theory, it is believed that the bulkiness of the ortho substituent can twist the dibenzo-fused 5-membered ring substituent out of plane and disrupt conjugation. In particular, compounds with phenyl imidazole are prone to oxidation. It is thought that the steric effects created by the ortho substituent protects the A ring from attack by oxygen, which may increase the stability of the compound. The bulkiness of the ortho substituents also decreases stacking of the compound and thereby increases the quantum yield. Therefore, the twisted dibenzo-fused 5-membered ring substituted ligand may improve device efficiency and device lifetime.

The LUMO is thought to be localized on the dibenzo-fused 5-membered ring substituent, i.e., C ring, on the ligand in the compounds. Dibenzofuran and dibenzothiophene segments in hosts can stabilize electrons. It is believed that increasing the conjugation of C ring may improve device stability. The compounds provided herein have a dibenzo-fused 5-membered ring as the LUMO position such that the compounds may provide better device stability. In particular, compounds including dibenzofuran and/or dibenzothiophene as the C ring may have a more stabilized LUMO and improved device stability. For example, Compound 1 includes a dibenzofuran moiety and E1 includes a phenyl. Compound 1 showed improved stability in devices compared to E1.

In addition, the compounds provide beneficial properties while maintaining desirable emission spectra. For example, the color of Compound 1 is only slightly shifted compared to E1.

Further, the compounds provided have shorter excited state lifetimes and have higher radiative rates than previously reported compounds. The shortened transient lifetime of these compounds may provide improved photophysical properties. In particular, these compounds may spend less time in the excited state, thereby decreasing the possibility for photochemical reactions or quenching to occur. For example, the measured transient lifetime of compounds provided is shorter than that of previously reported compounds (see Table 4). Therefore, these compounds may provide devices with improved stability.

Novel compounds including a ligand with a dibenzo-fused 5-membered ring substituent are provided herein. These compounds provide a new type of material which may be advantageously used in OLEDs.

The compounds provided herein comprising a ligand L having the formula:

Formula I

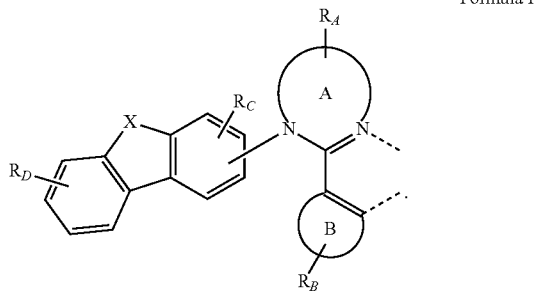

A and B are each independently a 5-membered or 6-membered carbocyclic or heterocyclic ring. Preferably, B is phenyl. $R_A$, $R_B$, $R_C$, and $R_D$ represent mono, di, tri, or tetra substitutions. $R_A$, $R_B$, $R_C$, and $R_D$ are independently selected from hydrogen, halogen, alkyl, alkoxy, amino, alkenyl, alkynyl, aryl and heteroaryl. $R_A$, $R_B$, $R_C$, and $R_D$ are optionally fused. X is selected from the group consisting of CRR', NR, O, and S. R and R' are independently selected from the group consisting of alkyl and aryl. The ligand L is coordinated to a metal M having an atomic number greater than 40. Preferably, M is Ir.

In one aspect, the compound is homoleptic. Homoleptic compounds may have several advantageous properties, such as straightforward synthesis and purification and predictable photophysical properties. In particular, homoleptic compounds may be easier to synthesize and purify because all of the ligands in the complex are the same. Examples of homoleptic compounds include, without limitation, Compounds 1-72 and Compounds 83-114.

The compounds provided herein may also be heteroleptic. Heteroleptic compounds may have several beneficial properties, including the ability to modify the properties of the compound. In particular, heteroleptic compounds provide highly tunable phosphorescent emissive materials, because the complex can contain different ligands with different HOMO/LUMO levels. Additionally, heteroleptic compounds may have a lower sublimation temperature. In another aspect, the compound is heteroleptic and all of the ligands L in the compound have Formula I. Example of these compounds include, without limitation, Compounds 81 and 82. In yet another aspect, the compound is heteroleptic and at least one of the ligands L in the compound have Formula I. Examples of these compounds include, without limitation, Compounds 73-82.

In one aspect, $R_C$ is two alkyl substituents. In another aspect, $R_C$ is two alkyl substituents having 3 or more carbon atoms. Alkyl substituents having 3 or more carbon atoms may include straight chain alkyls having more than 3 carbon atoms (e.g., butyl), branched alkyls having more than 3 carbon atoms (e.g., isobutyl), and cycloalkanes having more than 3 carbon atoms (e.g., cyclohexyl). Examples of compounds wherein $R_C$ is two alkyl substituents having 3 or more carbon atoms include, without limitation, Compounds 1-82.

The ring containing $R_C$ may have further substitutions at the positions ortho to the carbon atom connected to A. In one aspect, the ring containing $R_C$ is substituted at one of the positions ortho to the carbon atom connected to A. In another aspect, the ring containing $R_C$ has two substituents located at the positions ortho to the carbon atom connected to A. These compounds may include, for example, Compounds 1, 2 and 4-6. In a further aspect, the ring containing $R_C$ has one substituent that is located at a position ortho to the carbon atom attached to A and the other position ortho to the carbon atom attached to A is occupied by the substituted dibenzo moiety. These compounds may include, for example, Compounds 3, 7, and 11.

In one aspect, $R_C$ is hydrogen. The dibenzo-fused 5-membered ring substituent of such compounds is minimally twisted out of plane with respect to the A ring, e.g. imidazole. Examples of compounds comprising a minimally-twisted dibenzo-fused 5-membered ring substituted ligand include, without limitation, Compounds 83-114.

In one aspect, the compound is selected from the group consisting of:

Compound 1

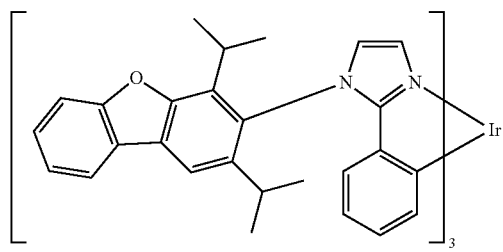

Compound 2

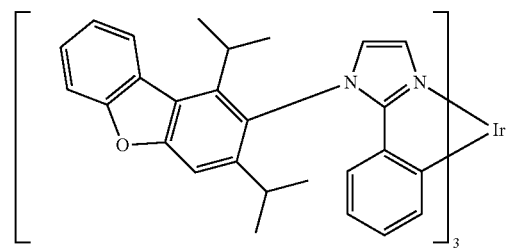

Compound 3
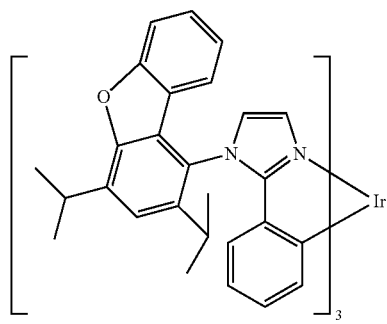
Compound 4
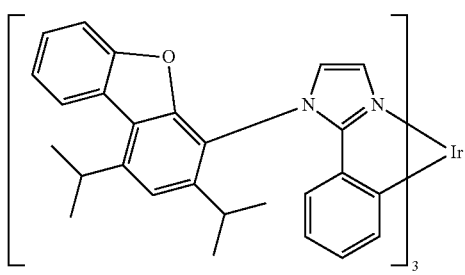
Compound 5
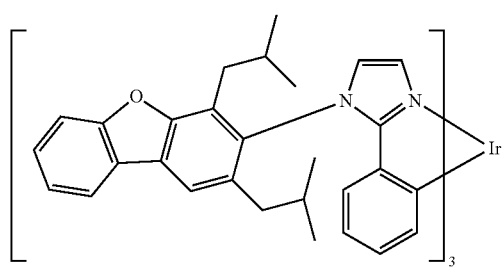
Compound 6
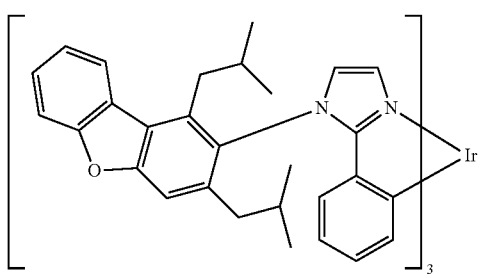
Compound 7
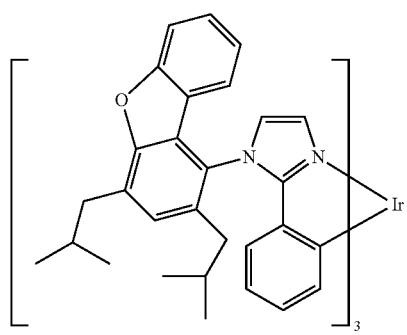
Compound 8
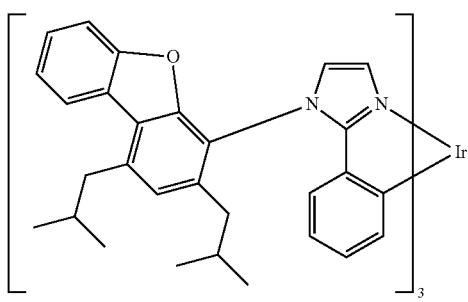
Compound 9
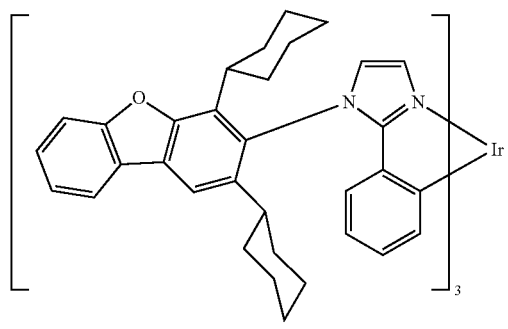
Compound 10
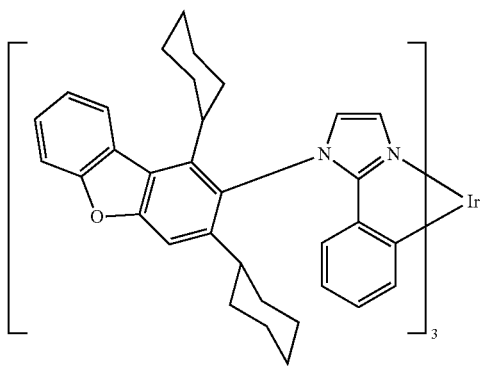

-continued
Compound 11
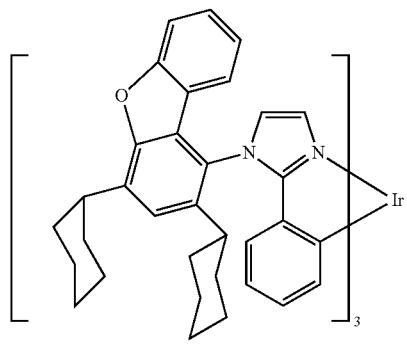
Compound 12
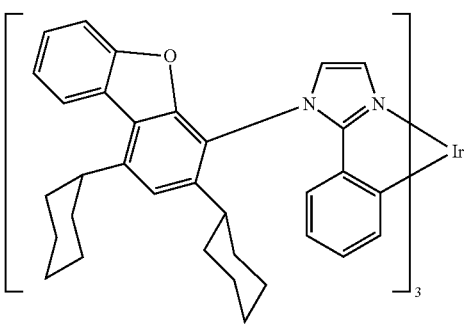
Compound 13
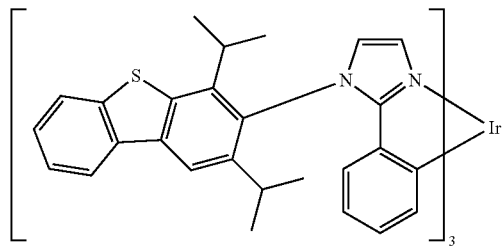
Compound 14
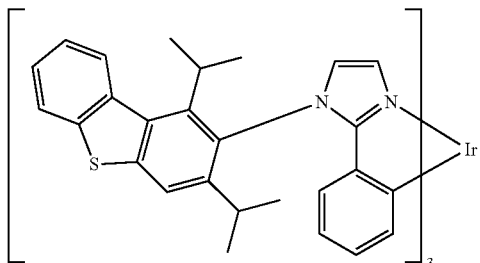
Compound 15
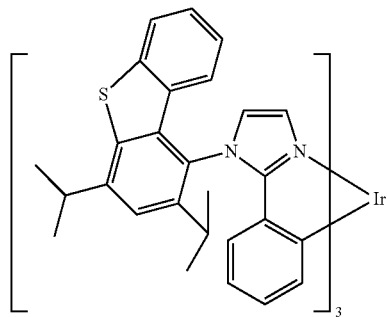
Compound 16
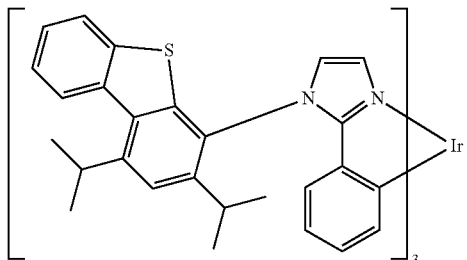
Compound 17
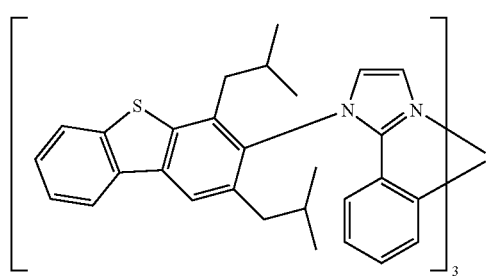
Compound 18
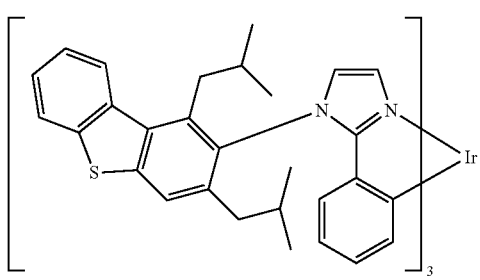
Compound 19
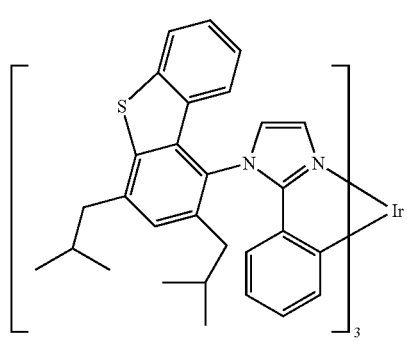
Compound 20
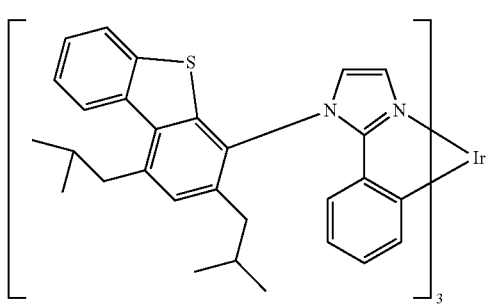

-continued
Compound 21
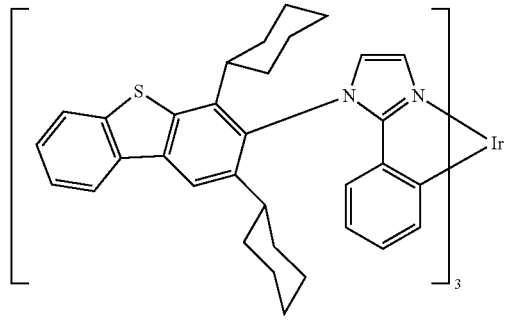
Compound 22
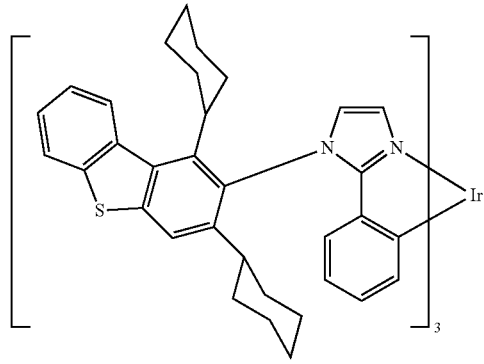
Compound 23
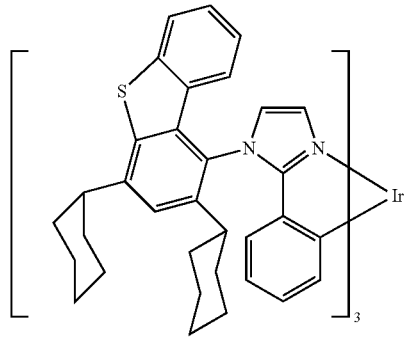
Compound 24
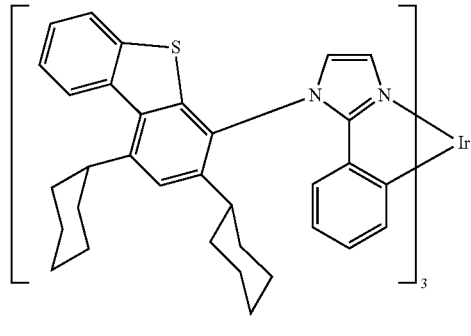
Compound 25
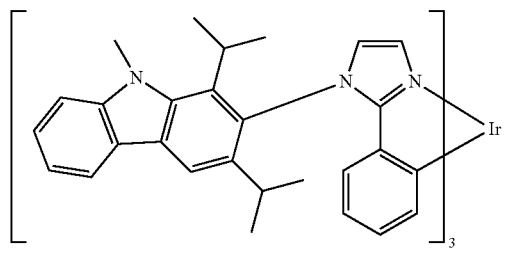
Compound 26
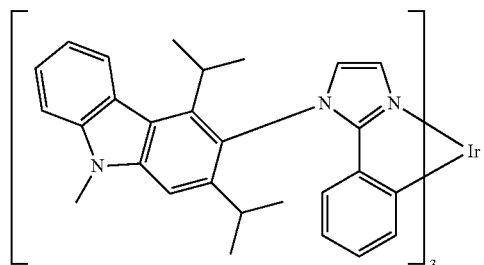
Compound 27
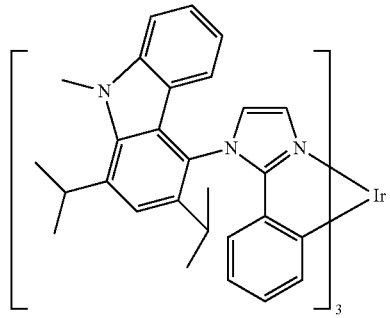
Compound 28
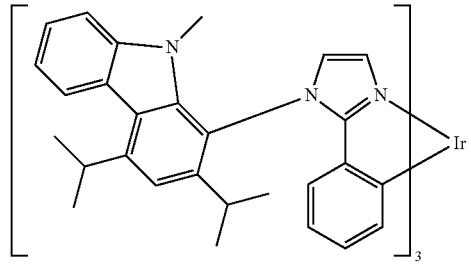
Compound 29
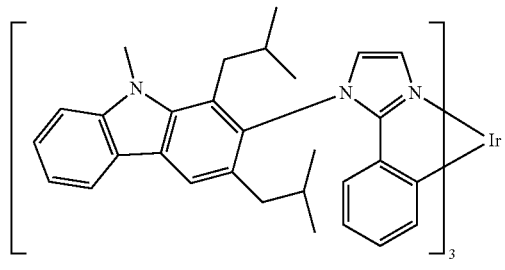
Compound 30
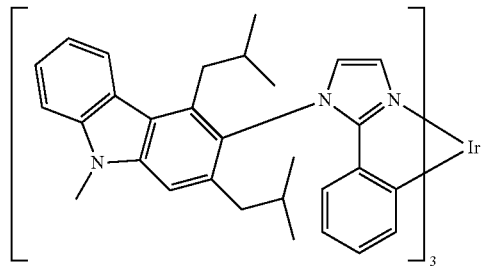

-continued
Compound 31
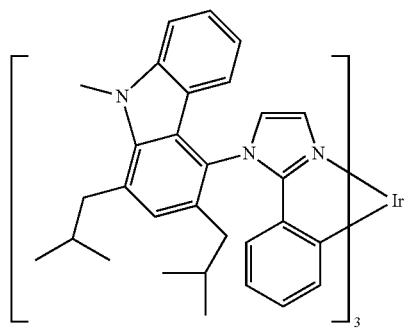
Compound 32
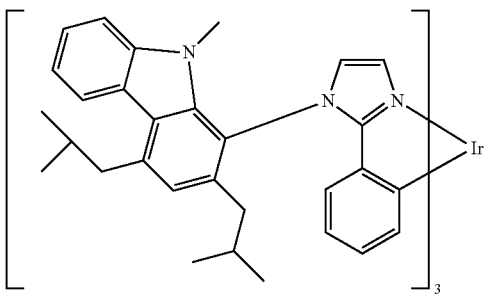
Compound 33
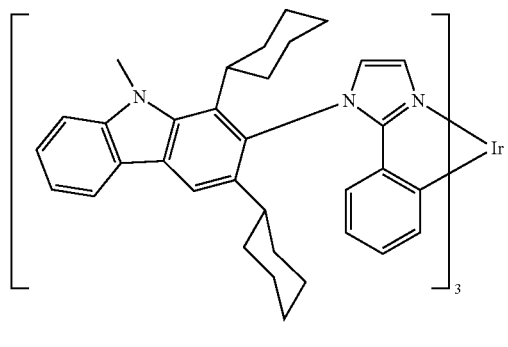
Compound 34
Compound 35
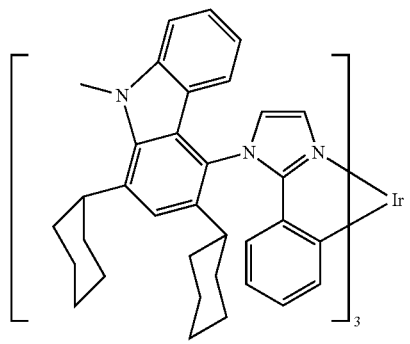
Compound 36
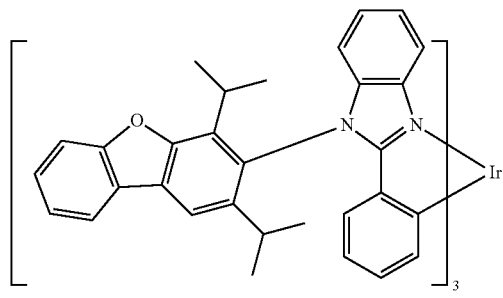
Compound 37
Compound 38
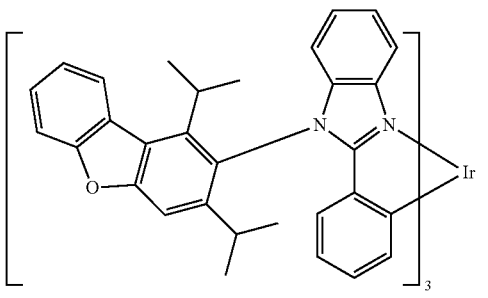

-continued
Compound 39
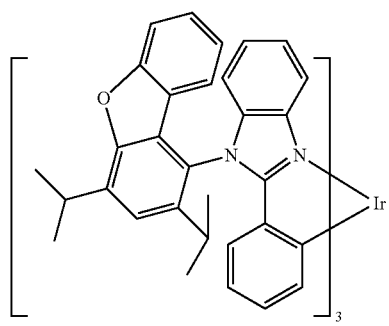
Compound 40
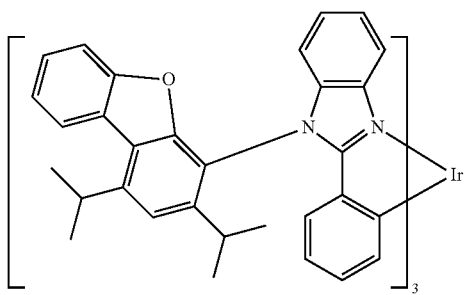
Compound 41
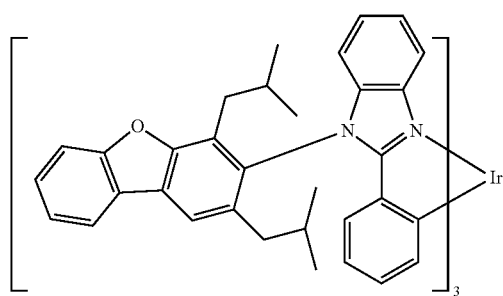
Compound 42
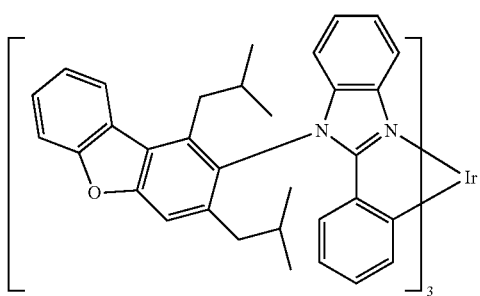
Compound 43
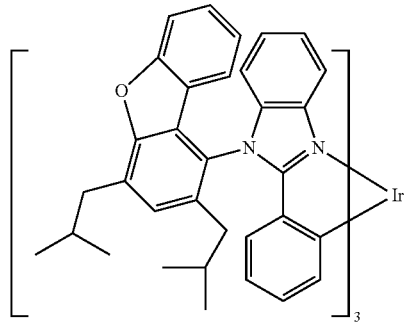
Compound 44
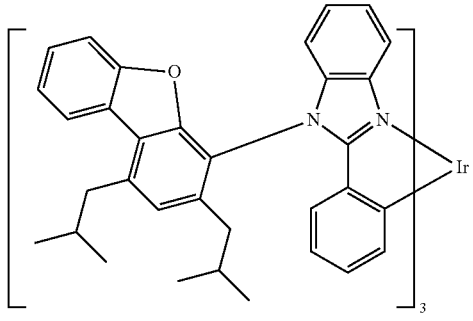
Compound 45
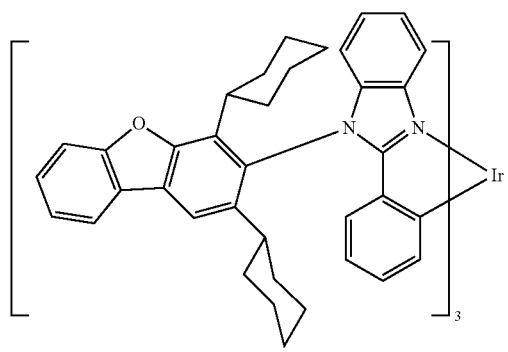
Compound 46
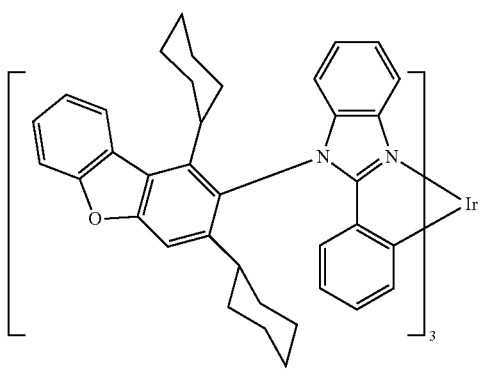

-continued
Compound 47
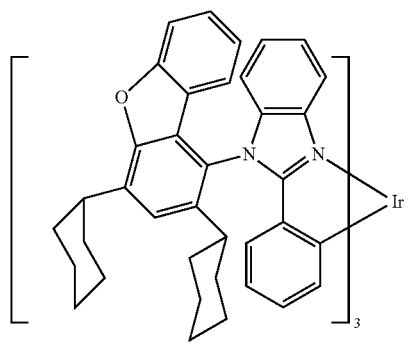
Compound 48
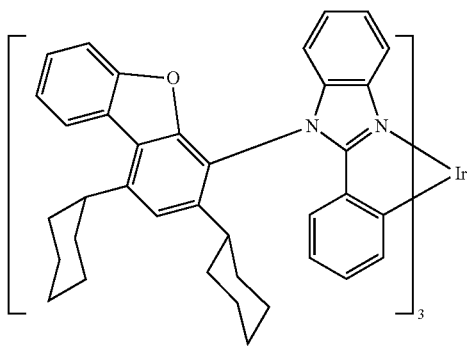
Compound 49
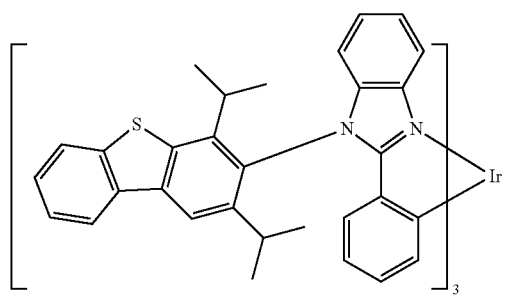
Compound 50
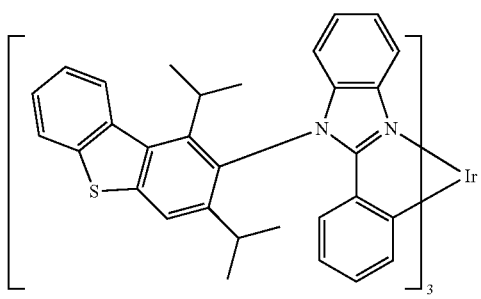
Compound 51
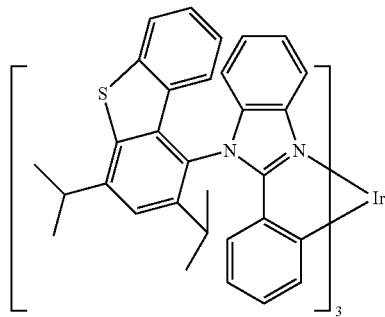
Compound 52
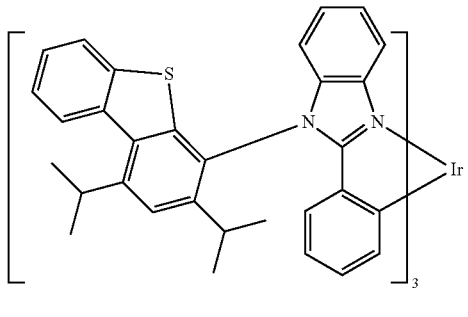
Compound 53
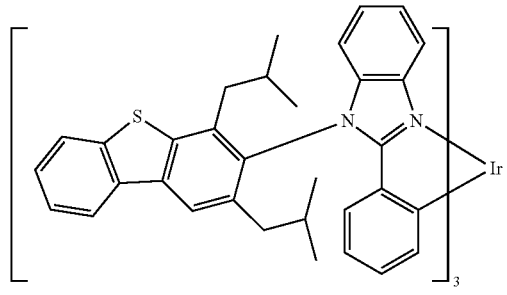
Compound 54
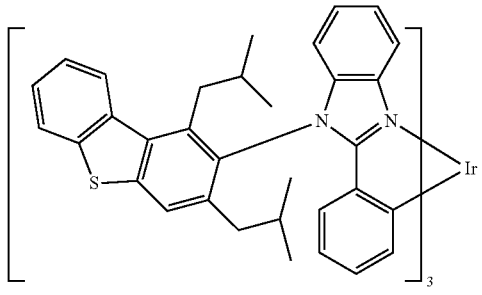
Compound 55
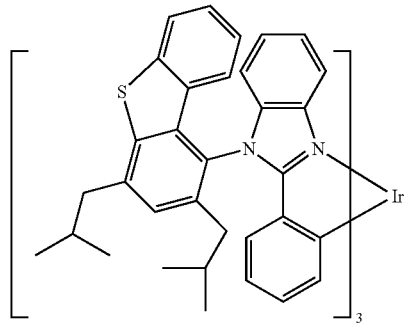
Compound 56
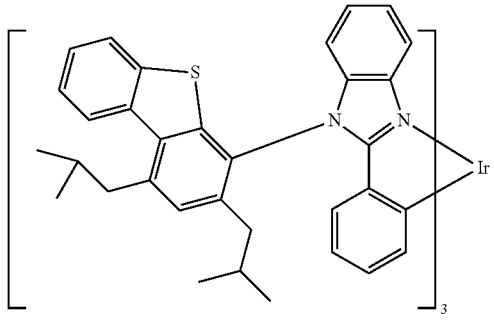

-continued
Compound 57
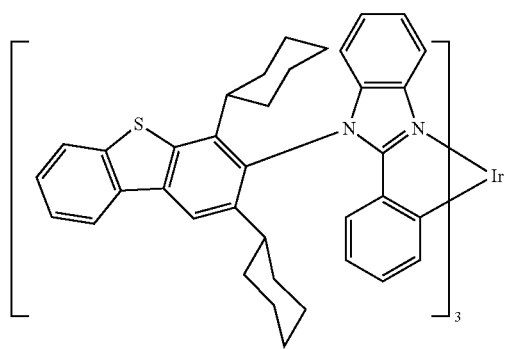
Compound 58
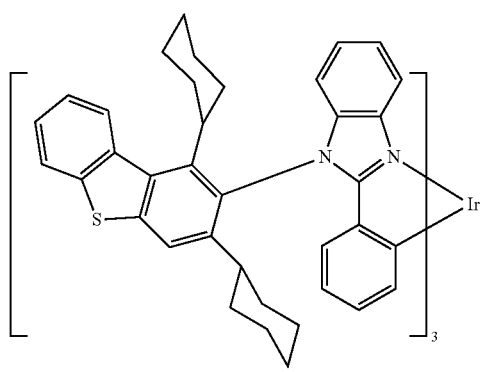
Compound 59
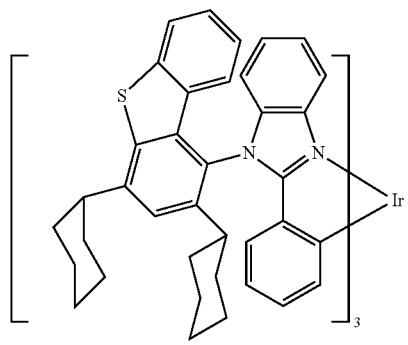
Compound 60
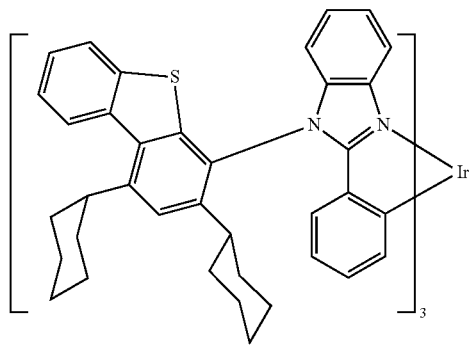
Compound 61
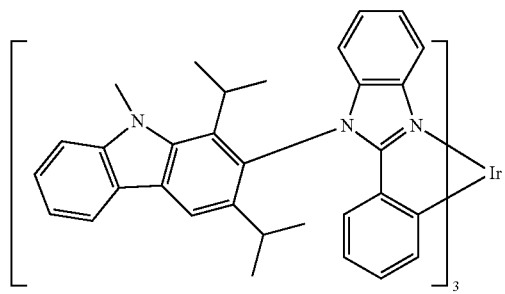
Compound 62
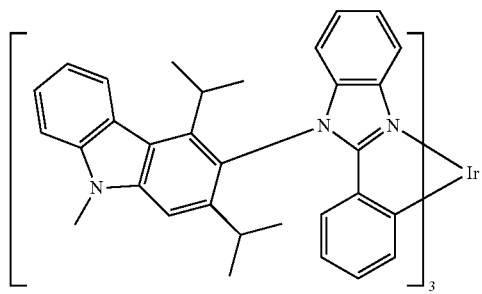
Compound 63
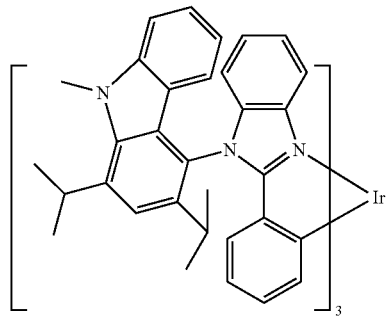
Compound 64
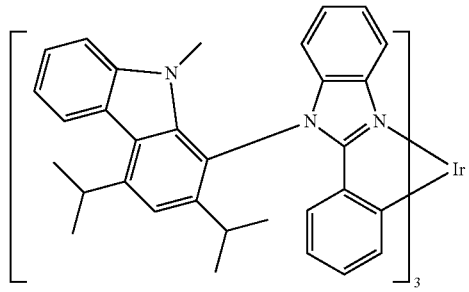

-continued
Compound 65
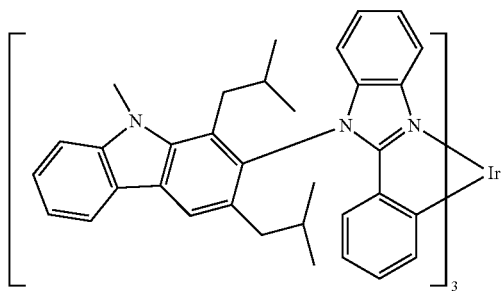
Compound 66
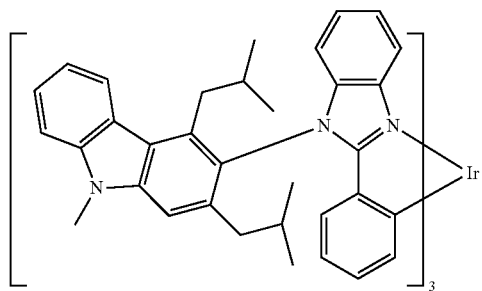
Compound 67
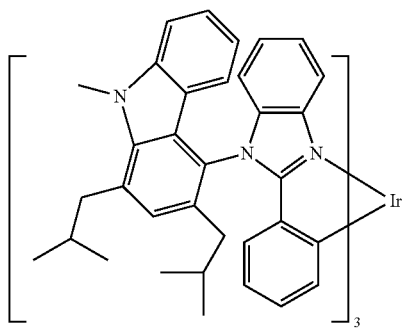
Compound 68
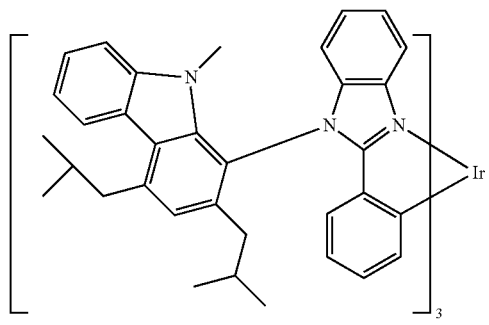
Compound 69
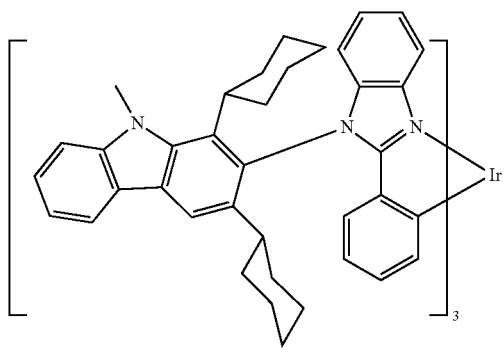
Compound 70
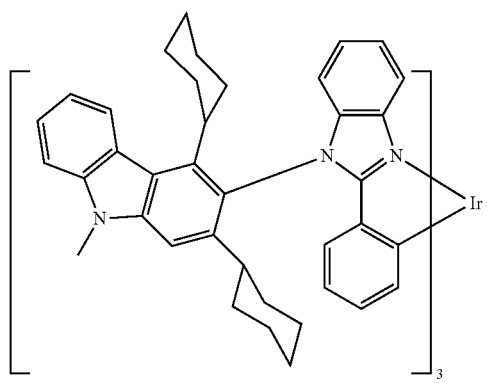
Compound 71
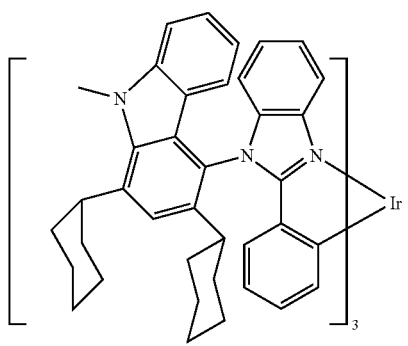
Compound 72
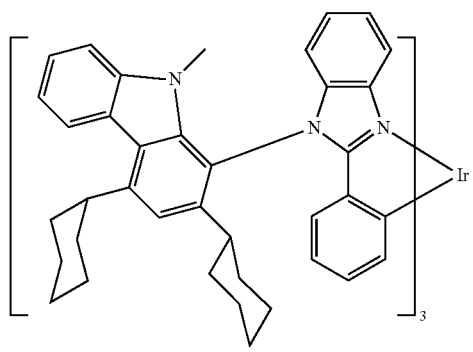

-continued
Compound 73
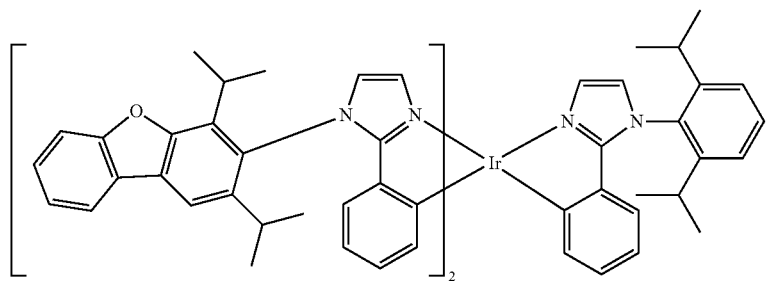
Compound 74
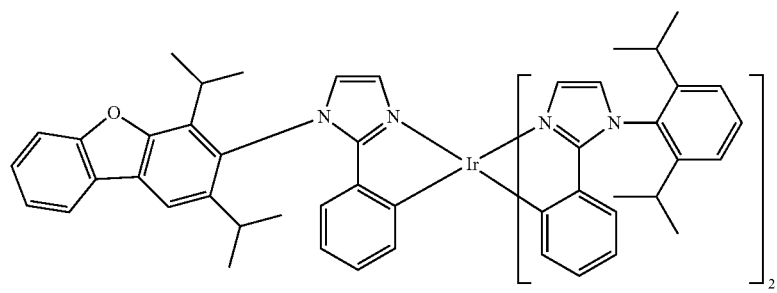
Compound 75
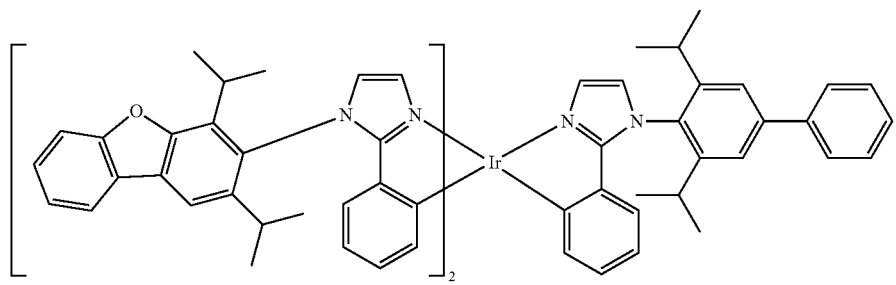
Compound 76
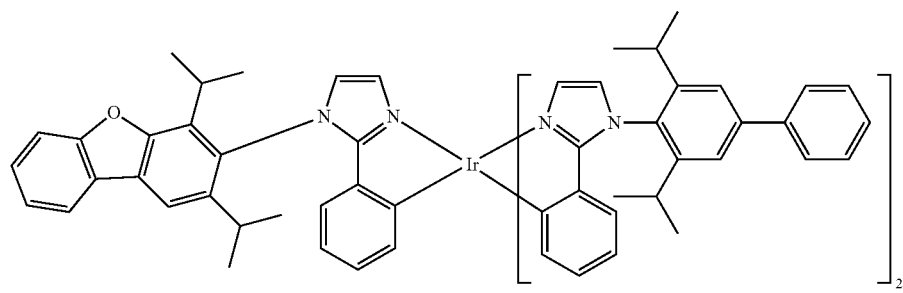
Compound 77
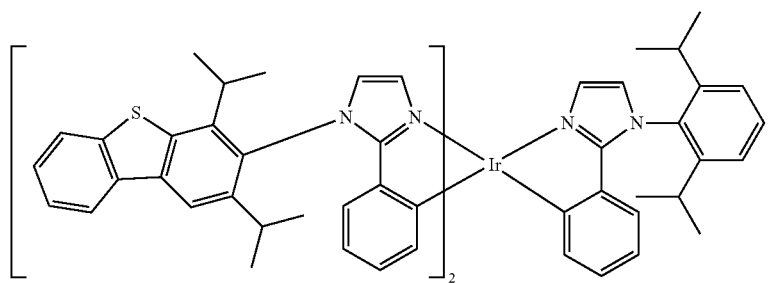

-continued
Compound 78
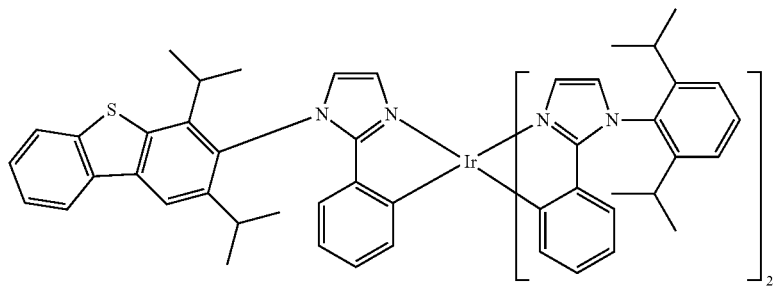
Compound 79
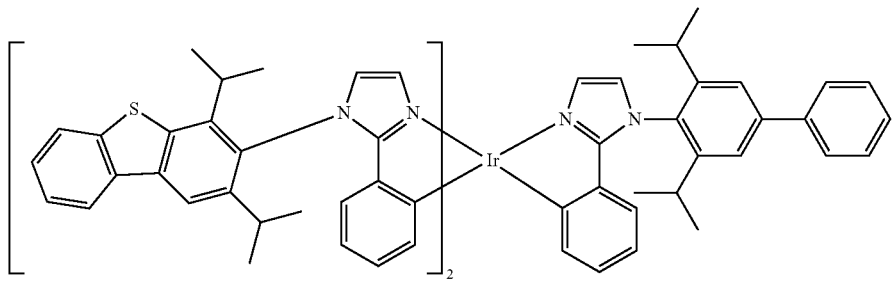
Compound 80
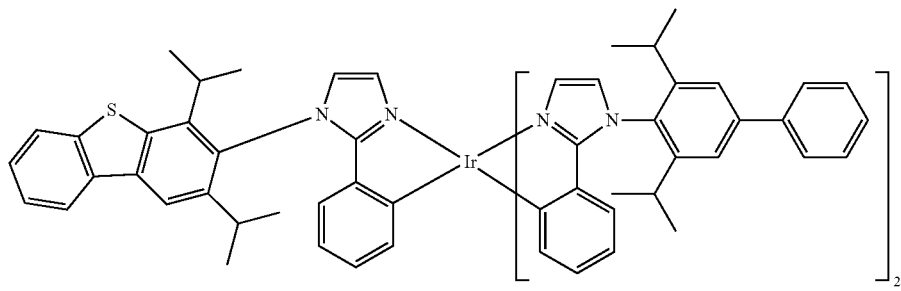
Compound 81
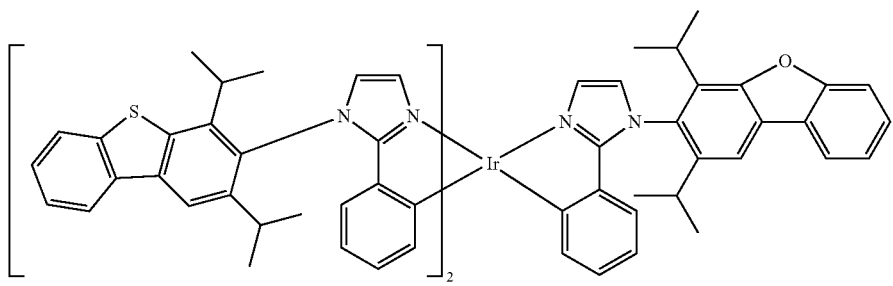
Compound 82
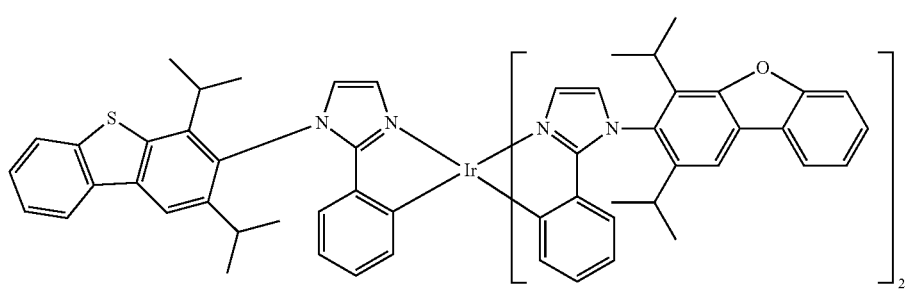

Compound 83
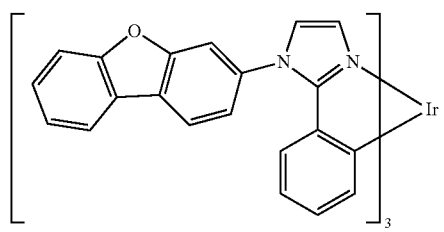
Compound 84
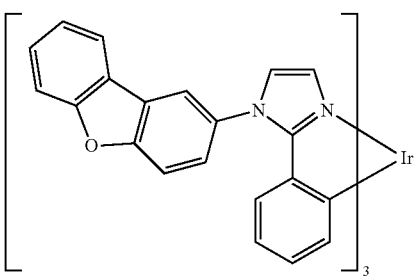
Compound 85
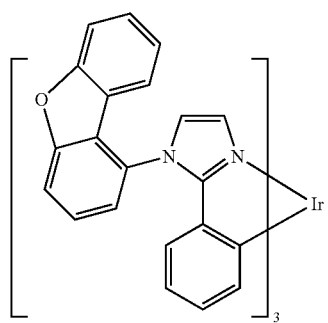
Compound 86
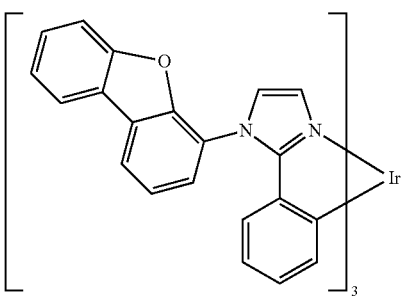
Compound 87
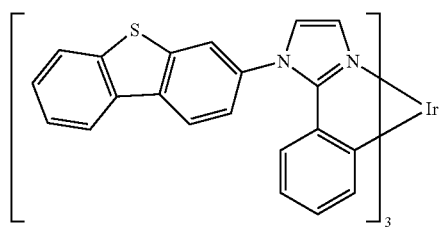
Compound 88
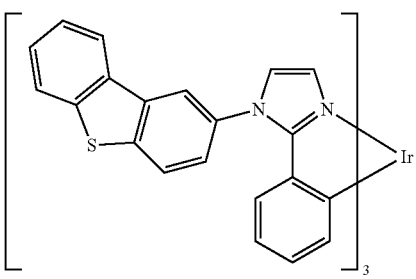
Compound 89
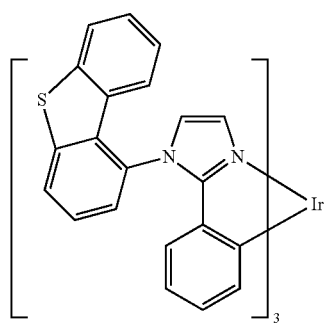
Compound 90
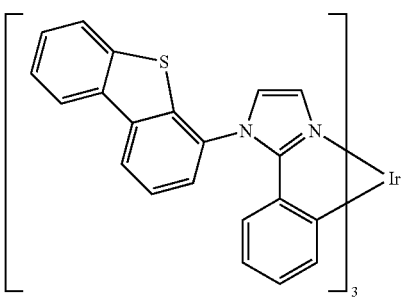
Compound 91
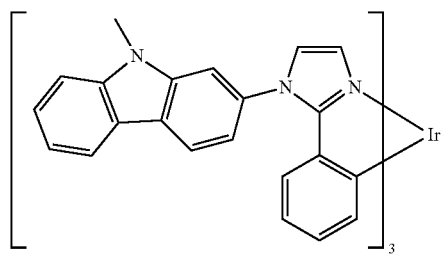
Compound 92
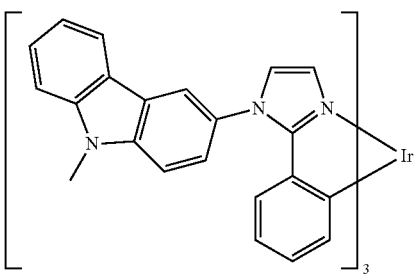

-continued
Compound 93
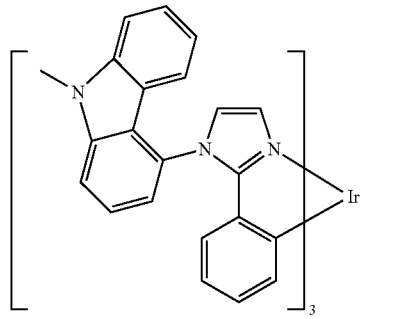
Compound 94
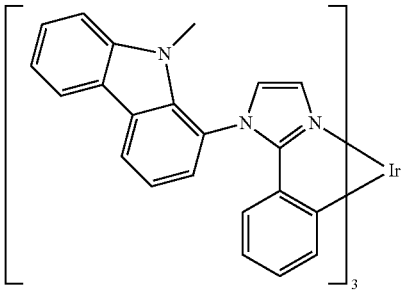
Compound 95
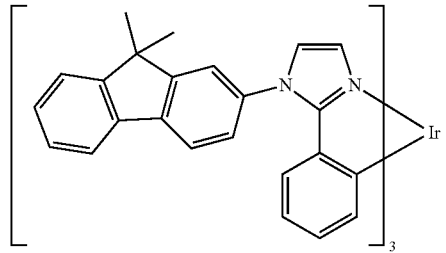
Compound 96
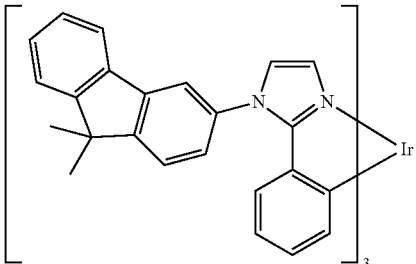
Compound 97
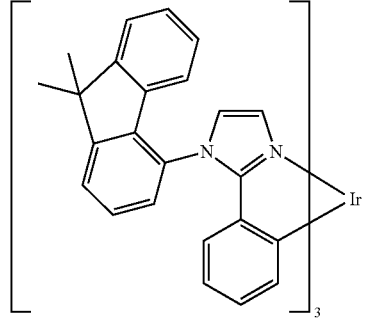
Compound 98
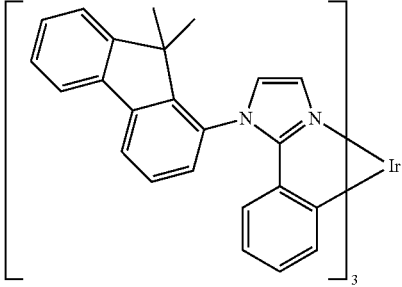
Compound 99
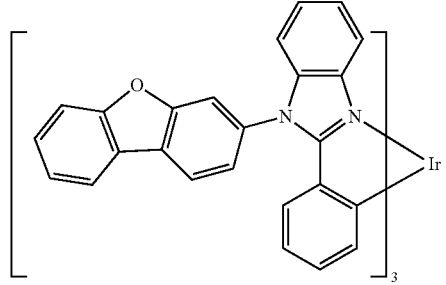
Compound 100
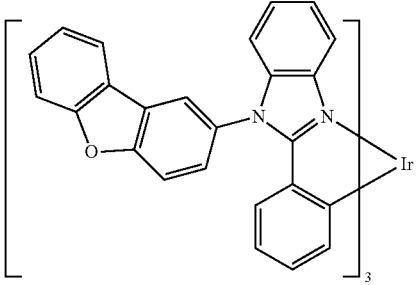
Compound 101
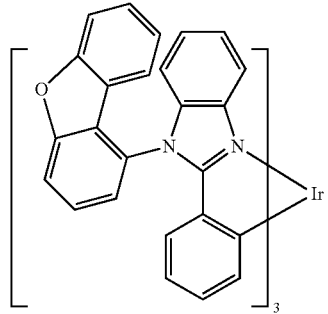
Compound 102
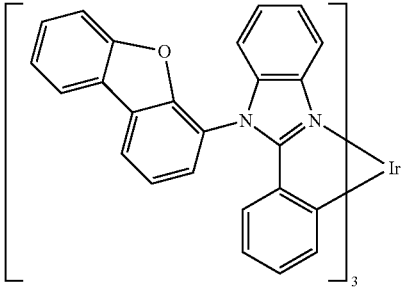

-continued
Compound 103
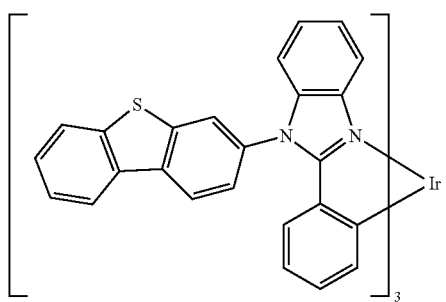
Compound 104
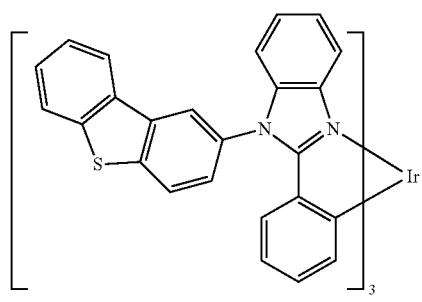
Compound 105
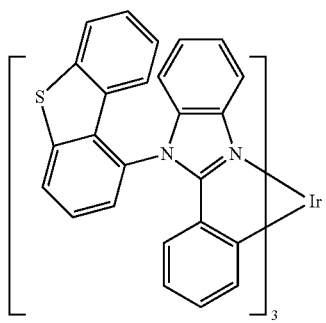
Compound 106
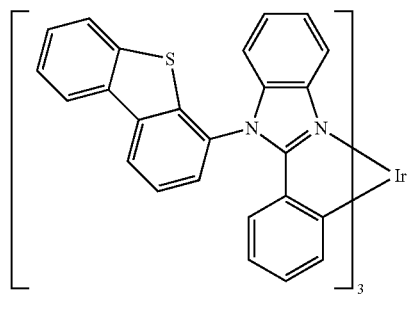
Compound 107
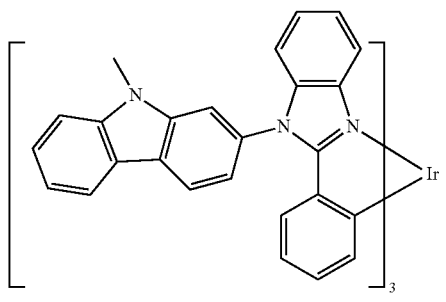
Compound 108
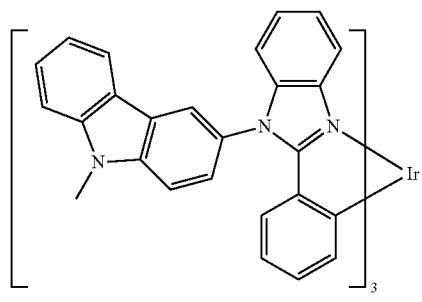
Compound 109
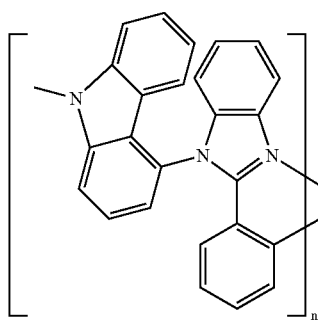
Compound 110
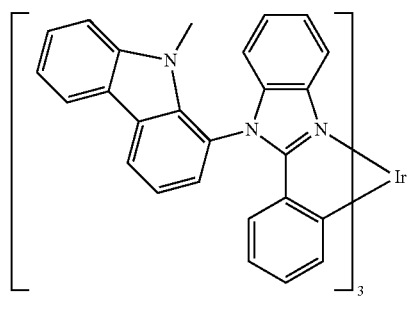
Compound 111
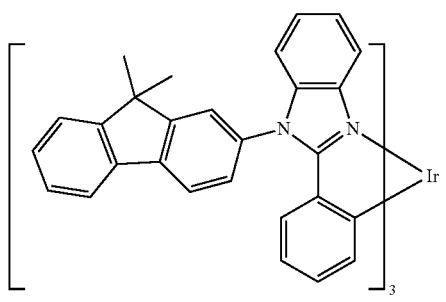
Compound 112
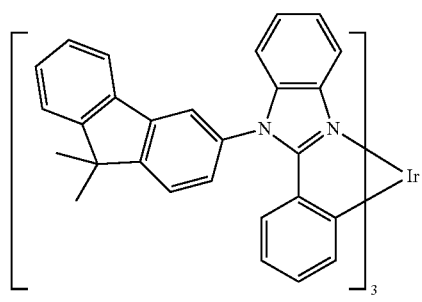

-continued

Compound 113

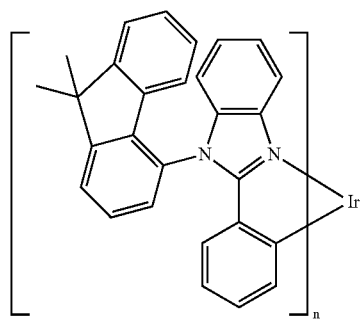

Compound 114

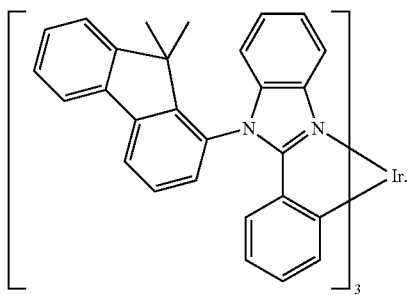

In one aspect, $R_A$ is fused to A. Preferably, $R_A$ is an aryl or heteroaryl. More preferably, $R_A$ is imidazole. Compounds including a dibenzo-fused 5-membered ring substituted benzimidazole ligand may have especially desirable properties, such as improved quantum efficiency and stability.

Compounds including a dibenzo-fused 5-membered ring substituted benzimidazole ligand include compounds selected from the group consisting of:

Compound 37

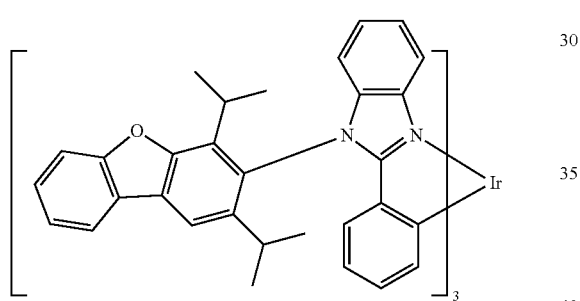

Compound 38

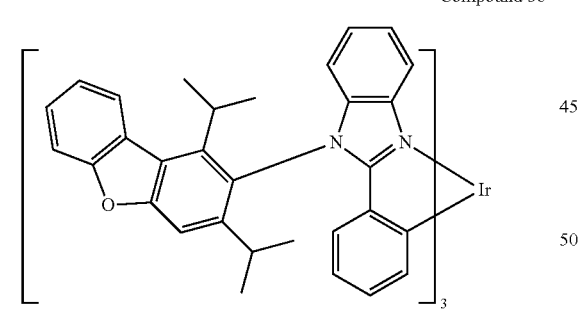

Compound 39

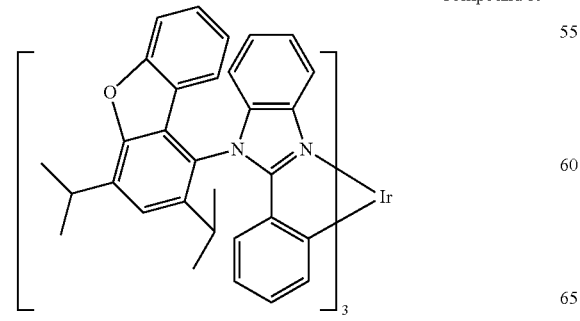

-continued

Compound 40

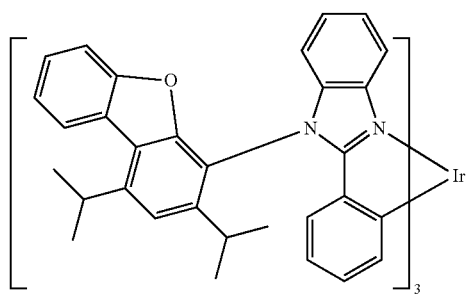

Compound 41

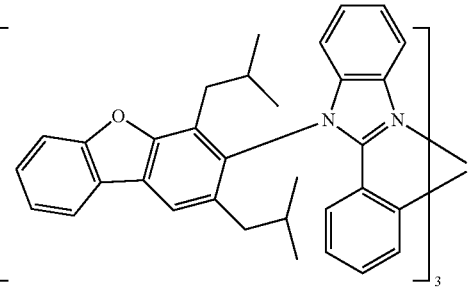

Compound 42

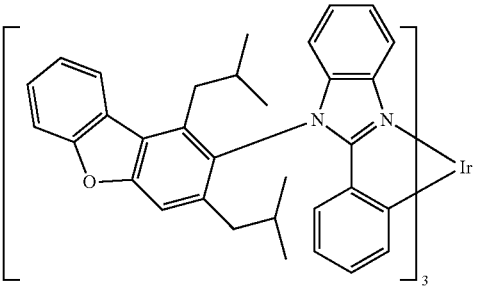

Compound 43
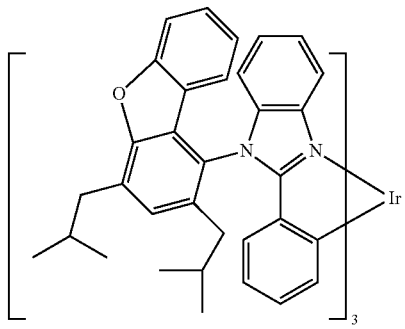
Compound 44
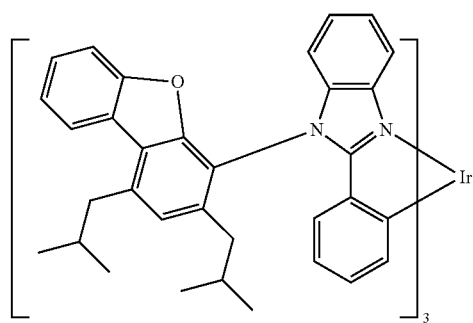
Compound 45
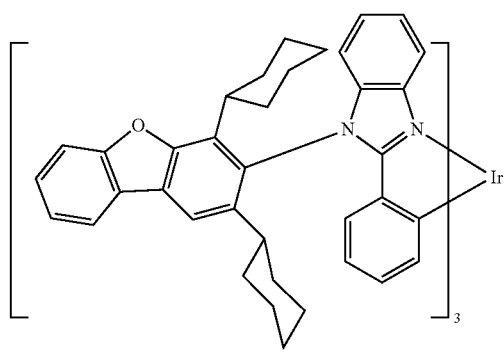
Compound 46
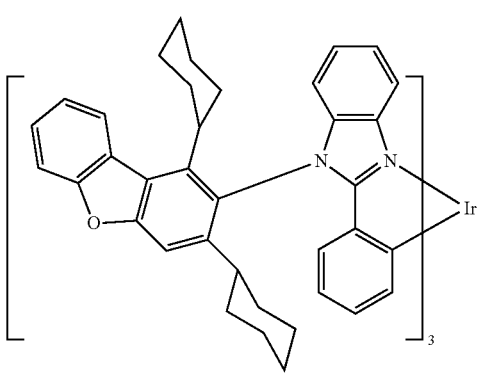
Compound 47
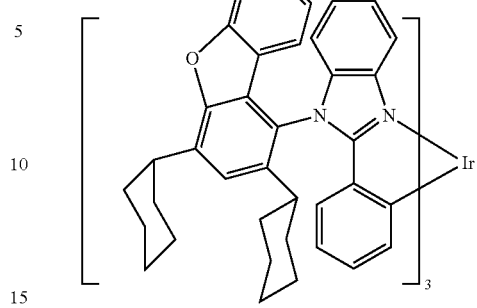
Compound 48
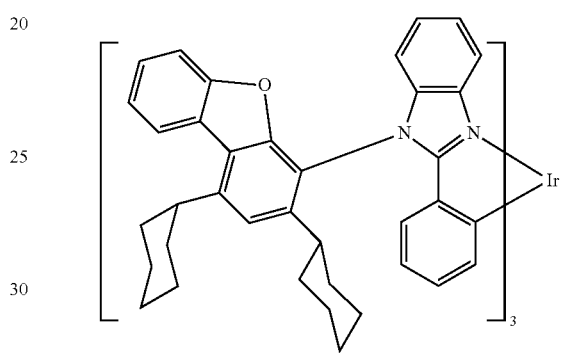
Compound 49
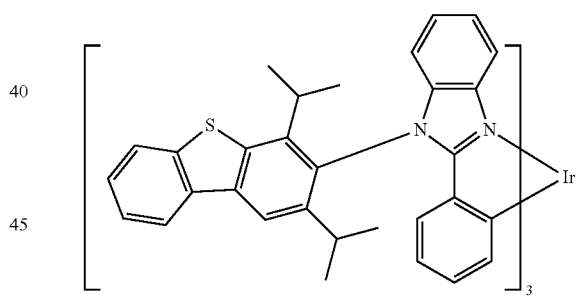
Compound 50
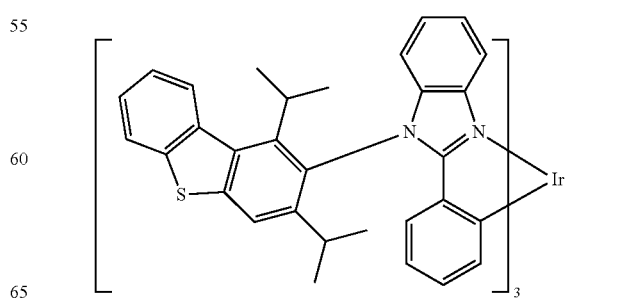

Compound 51
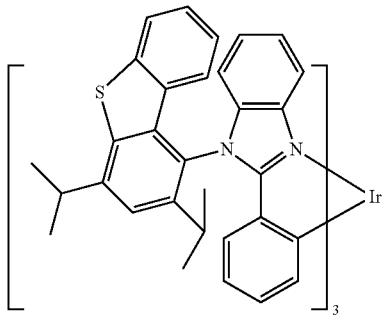
Compound 52
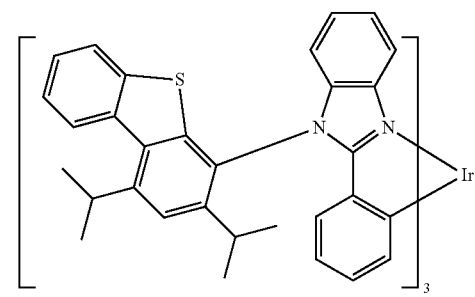
Compound 53
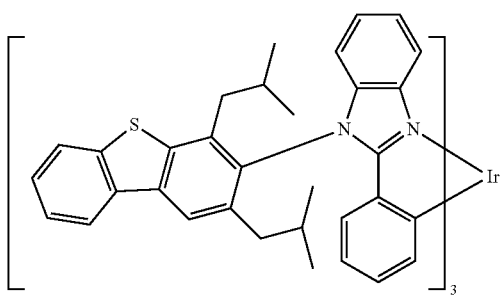
Compound 54
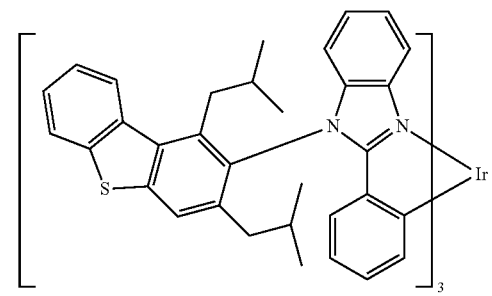
Compound 55
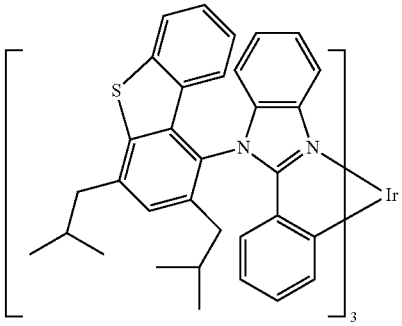
Compound 56
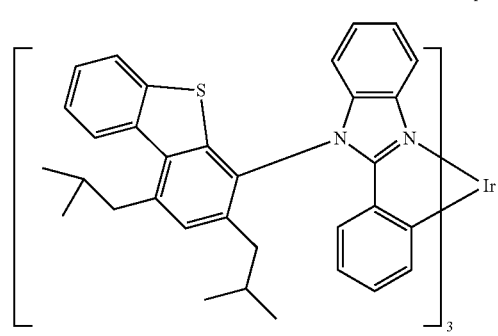
Compound 57
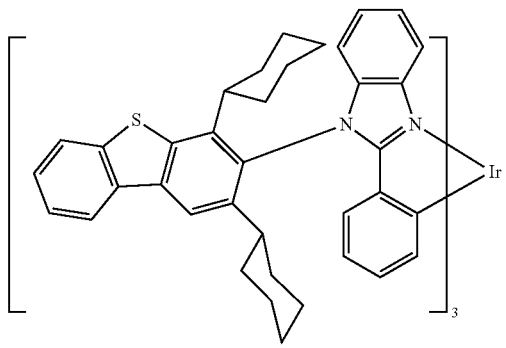
Compound 58
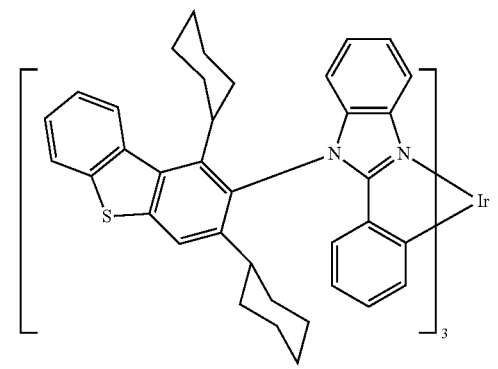
Compound 59
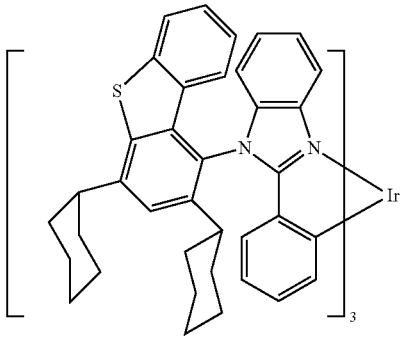

Compound 60
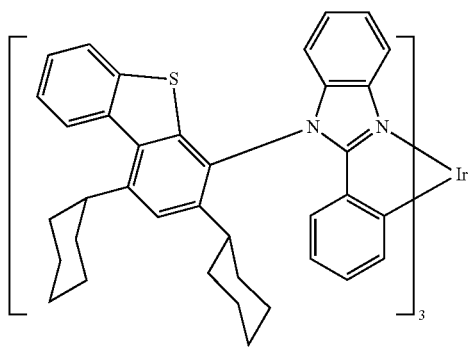
Compound 61
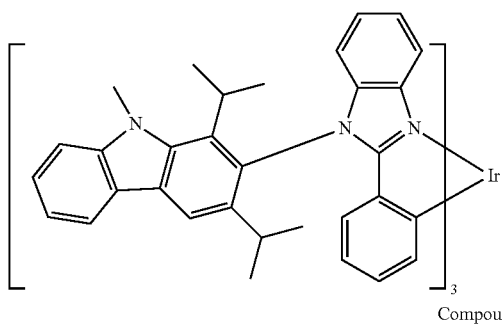
Compound 62
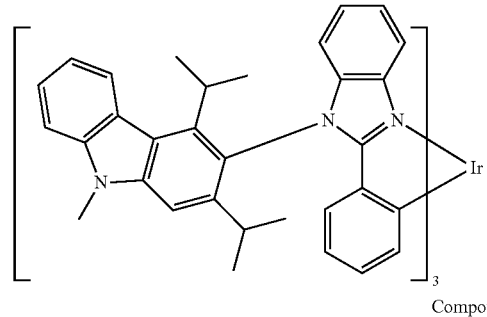
Compound 63
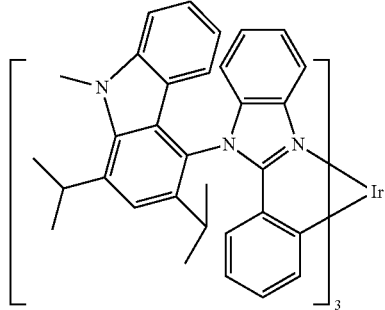
Compound 64
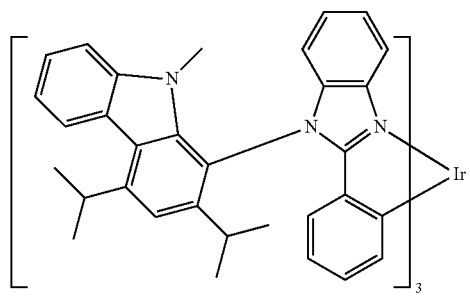
Compound 65
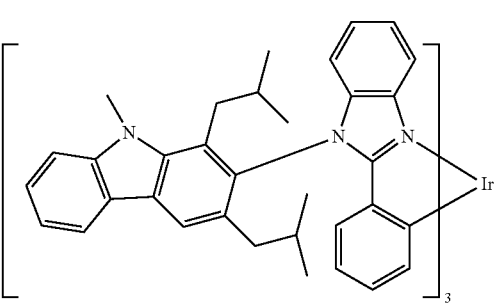
Compound 66
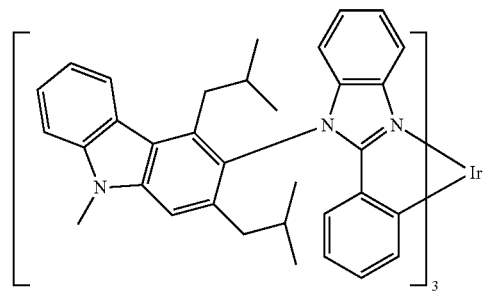
Compound 67
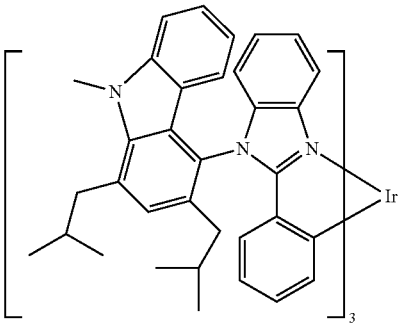
Compound 68
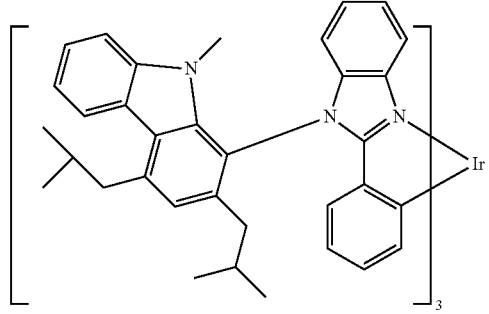

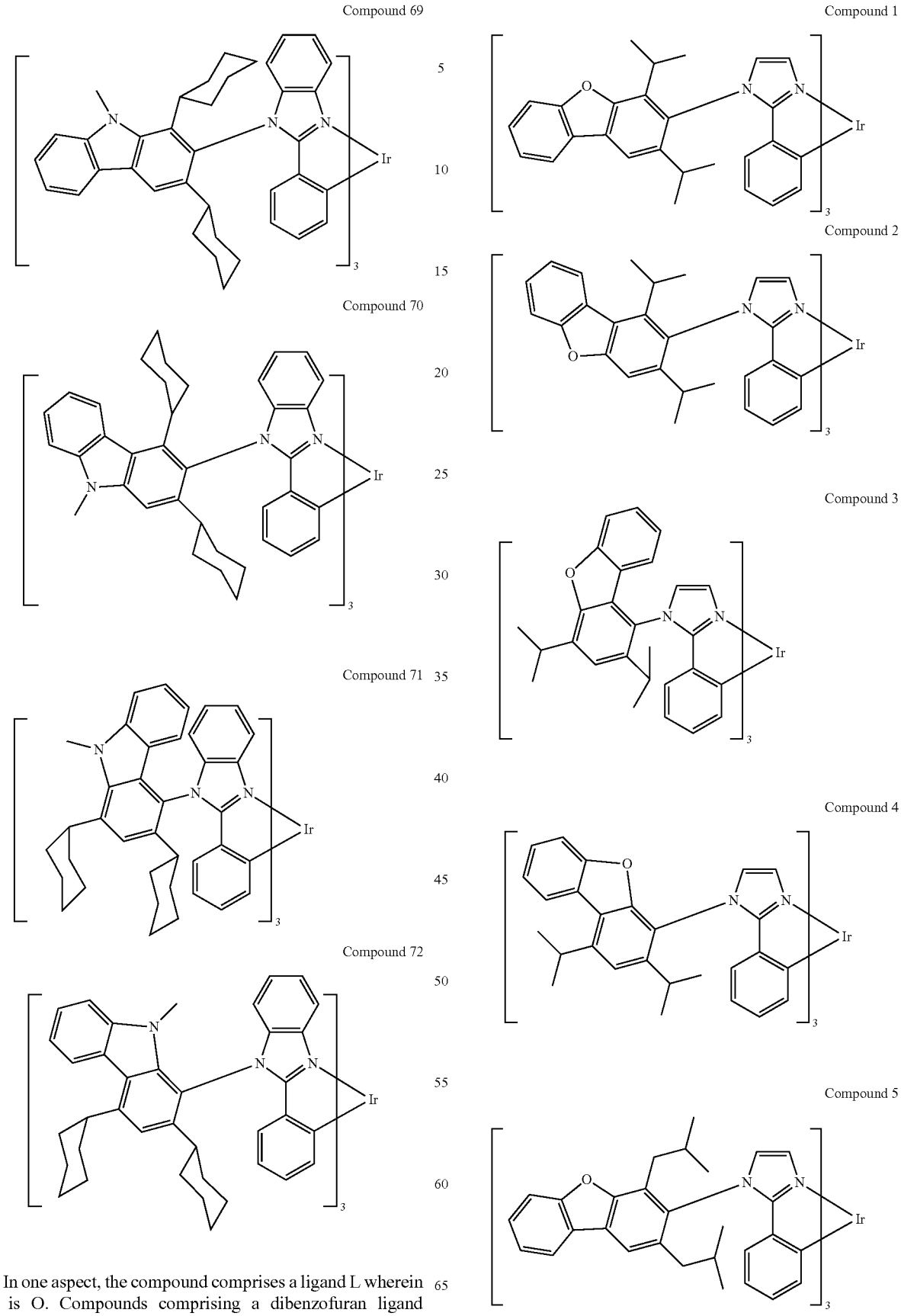
In one aspect, the compound comprises a ligand L wherein X is O. Compounds comprising a dibenzofuran ligand include compounds selected from the group consisting of:

Compound 5
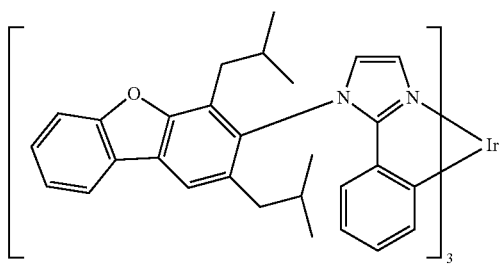
Compound 6
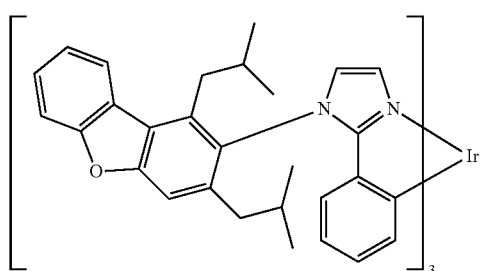
Compound 7
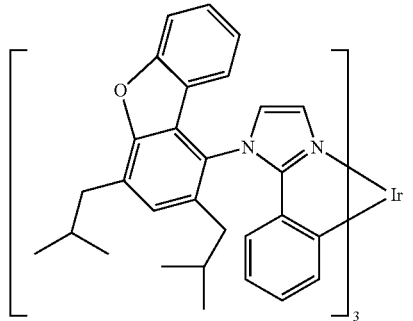
Compound 8
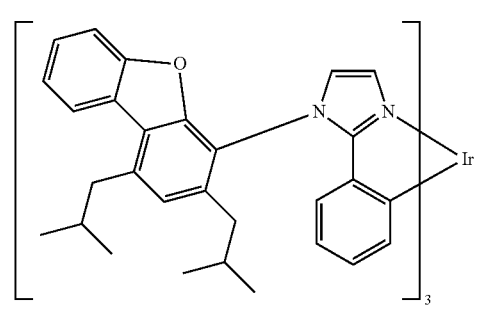
Compound 9
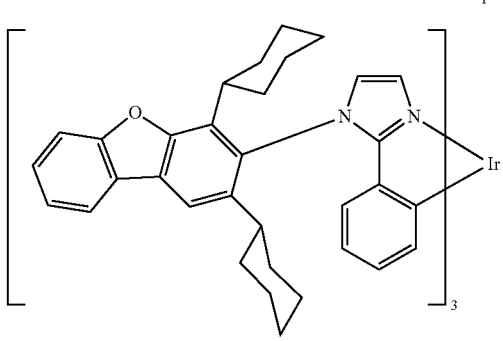
Compound 10
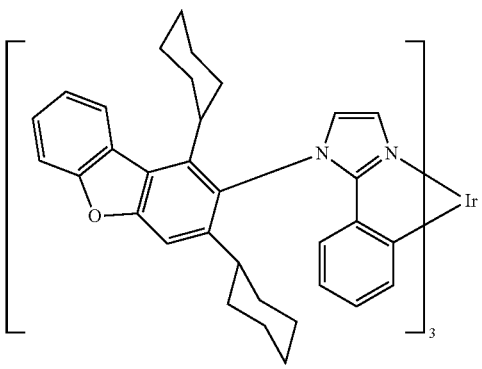
Compound 11
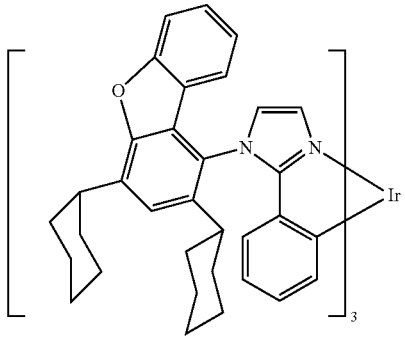
Compound 12
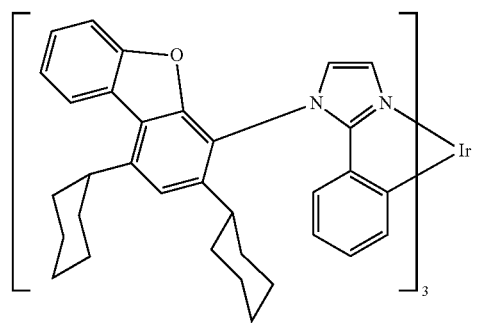
Compound 37
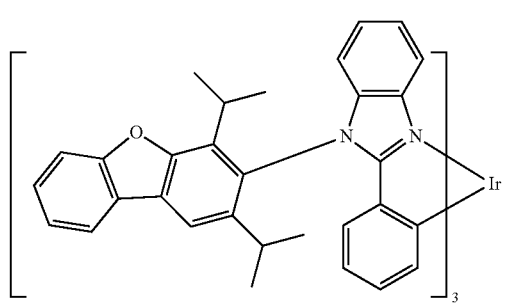

Compound 38
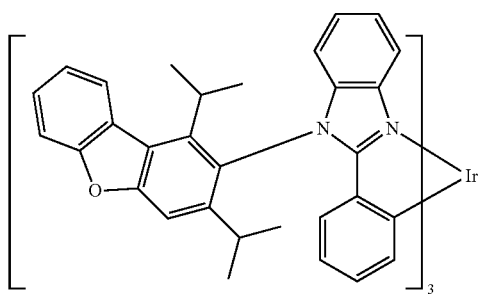
Compound 39
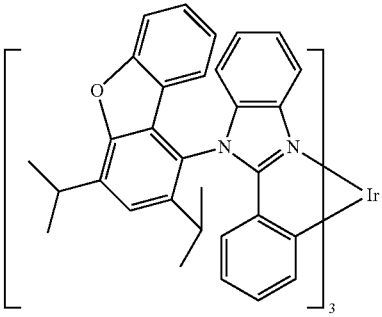
Compound 40
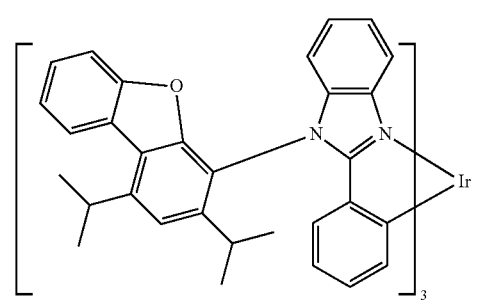
Compound 41
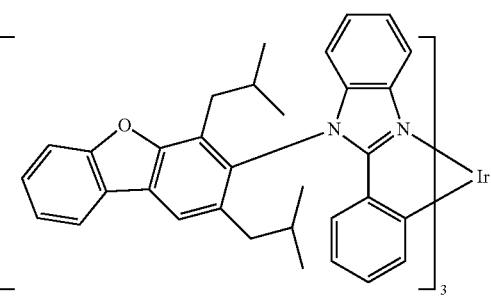
Compound 42
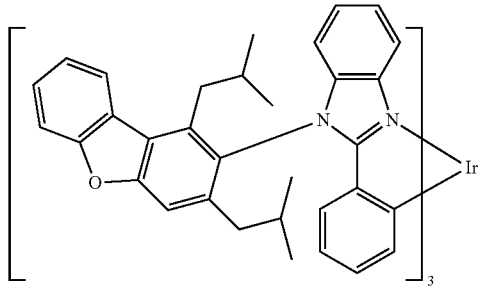
Compound 43
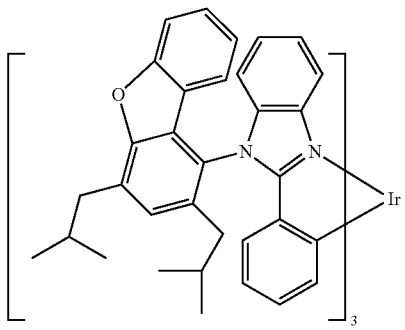
Compound 44
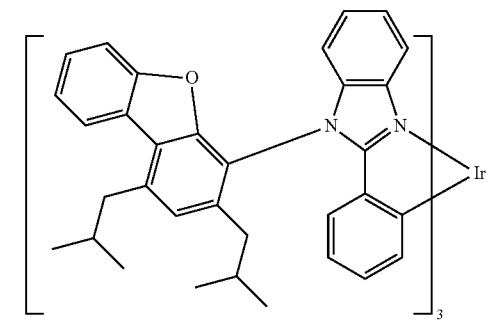
Compound 45
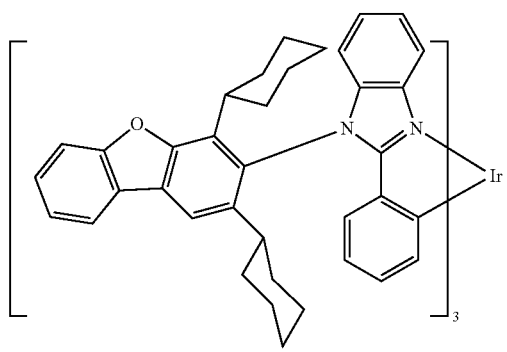
Compound 46
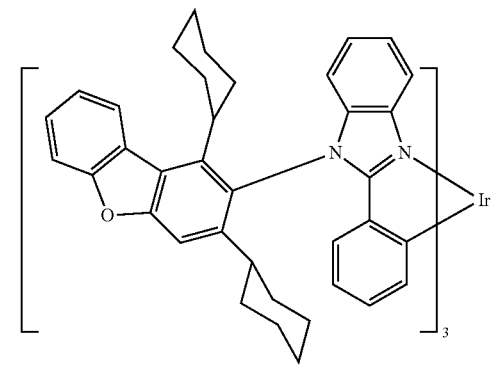

Compound 47
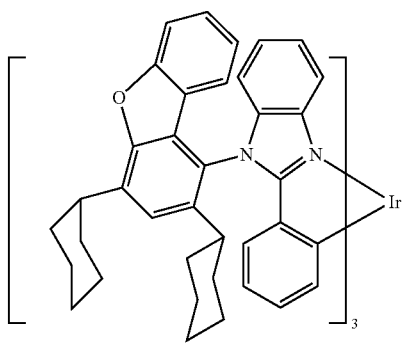
Compound 48
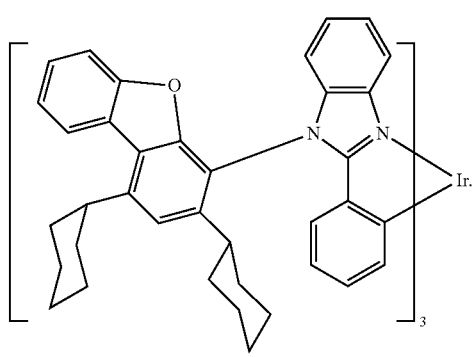
In one aspect, the compound comprises a ligand L wherein X is S. Compounds comprising a dibenzothiophene ligand include compounds selected from the group consisting of:
Compound 13
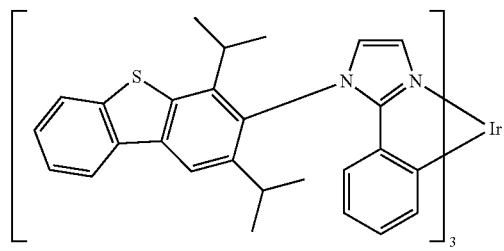
Compound 14
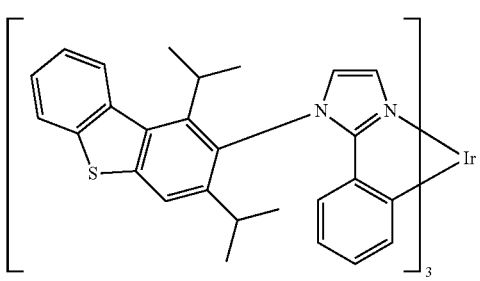
Compound 15
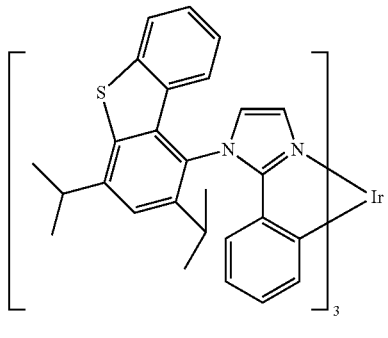
Compound 16
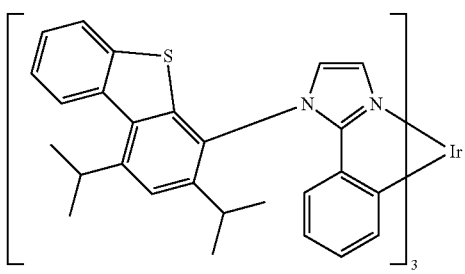
Compound 17
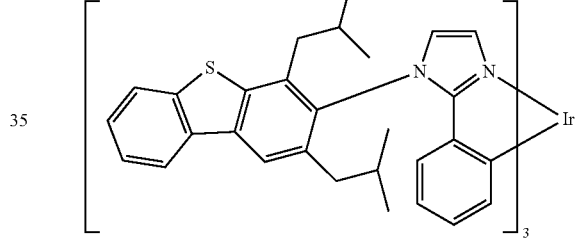
Compound 18
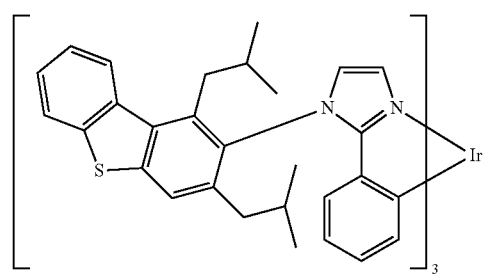
Compound 19
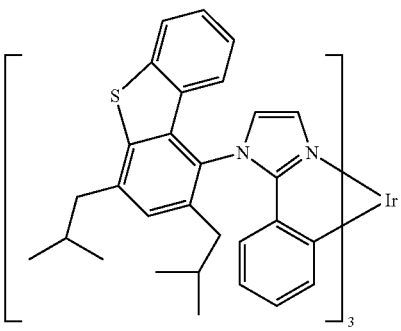

Compound 20
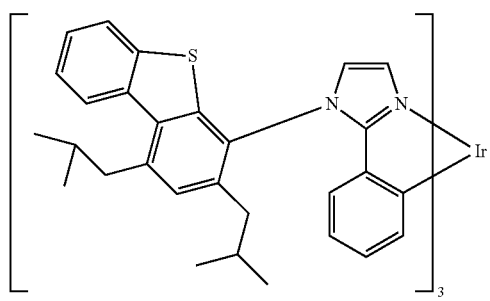
Compound 21
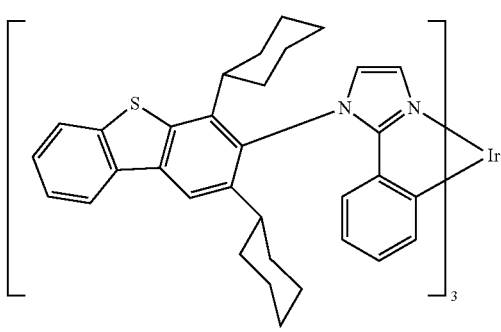
Compound 22
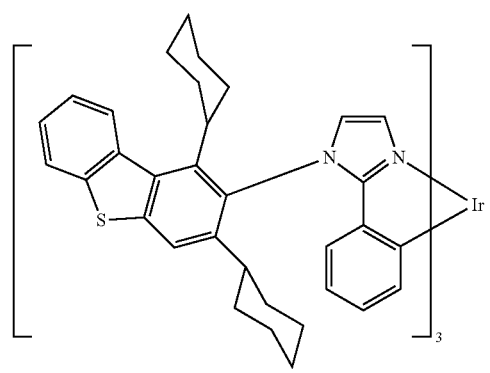
Compound 23
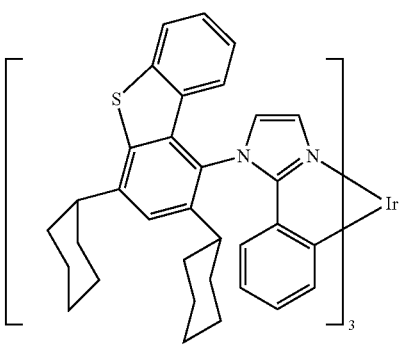
Compound 24
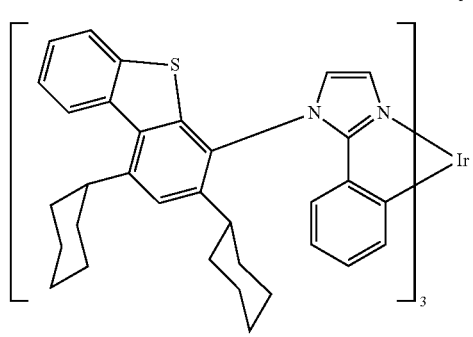
Compound 49
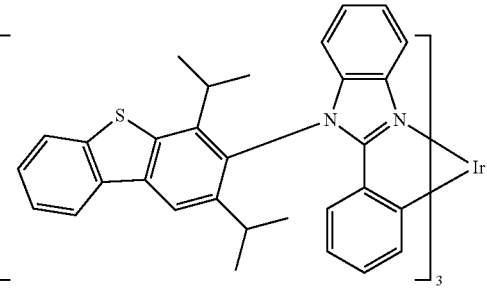
Compound 50
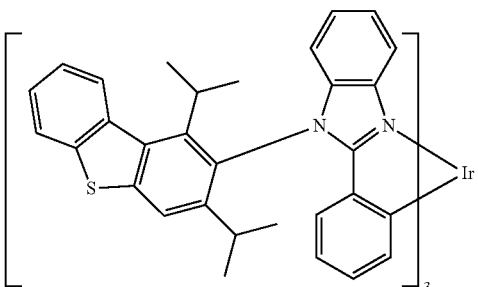
Compound 51
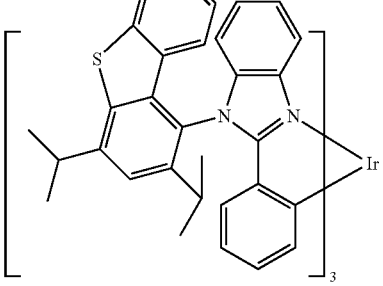
Compound 52

Compound 53
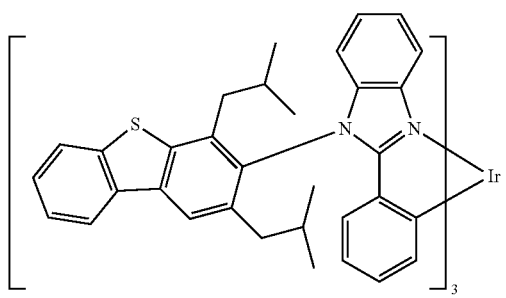
Compound 54
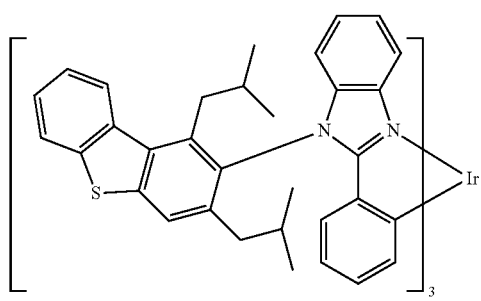
Compound 55
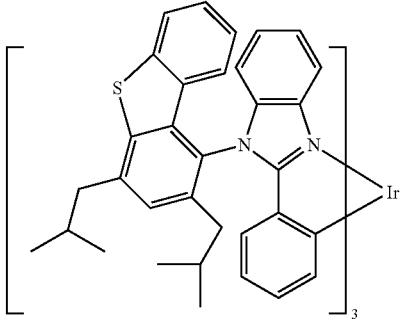
Compound 56
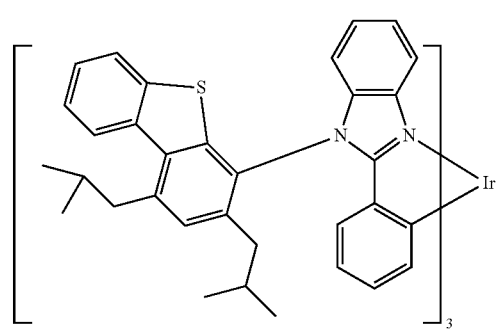
Compound 57
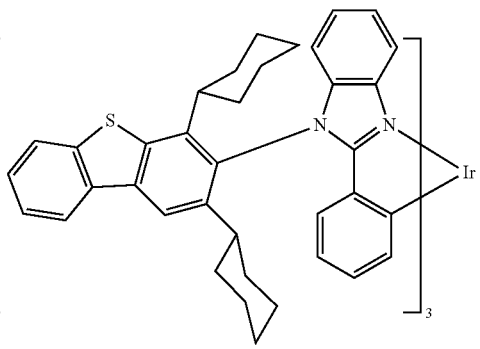
Compound 58
Compound 59
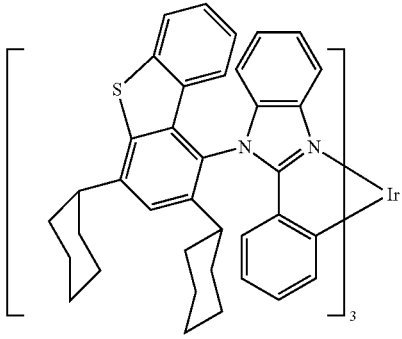
Compound 60
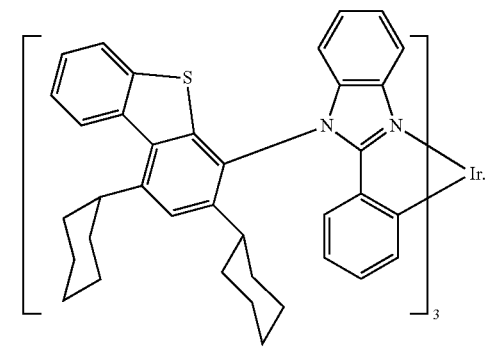
In one aspect, the compound comprises a ligand L wherein X is NR. Compounds comprising a carbazole ligand include compounds selected from the group consisting of:

Compound 25
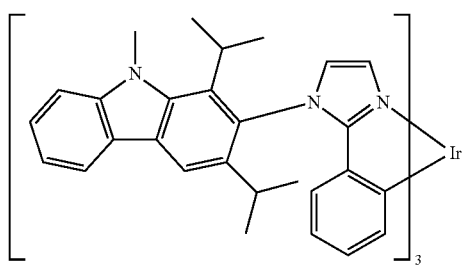
Compound 30
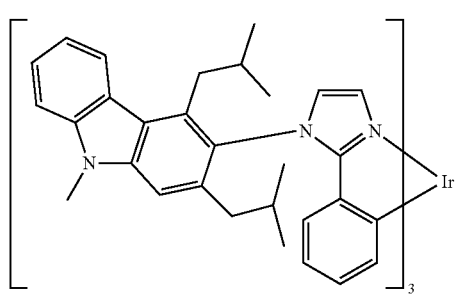
Compound 26
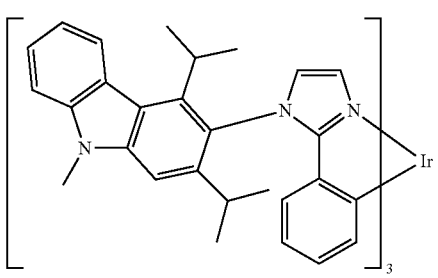
Compound 27
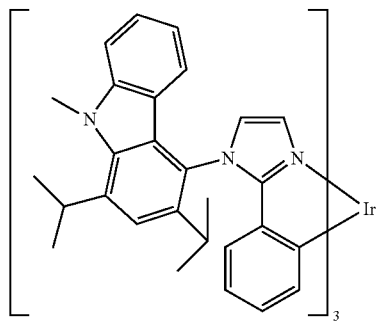
Compound 31
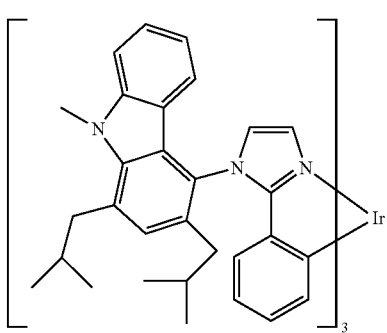
Compound 28
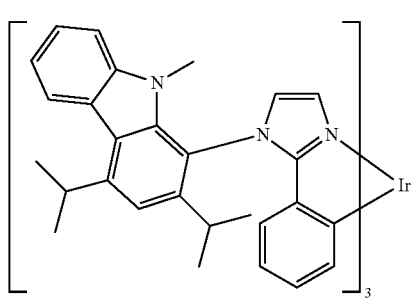
Compound 32
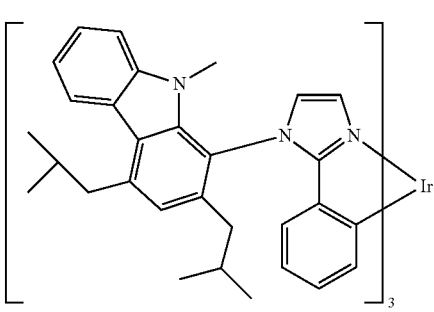
Compound 29
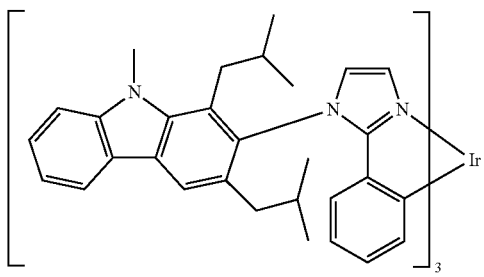
Compound 33
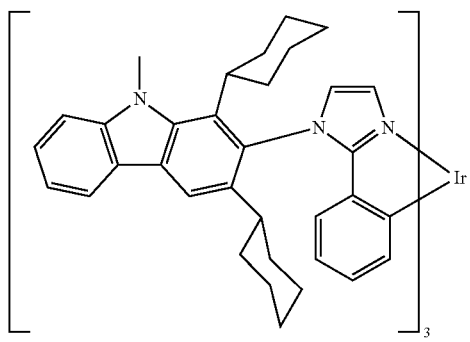

Compound 34
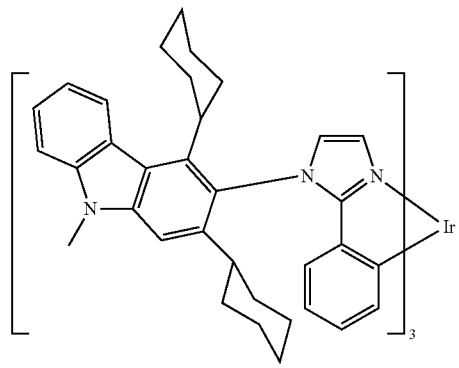
Compound 35
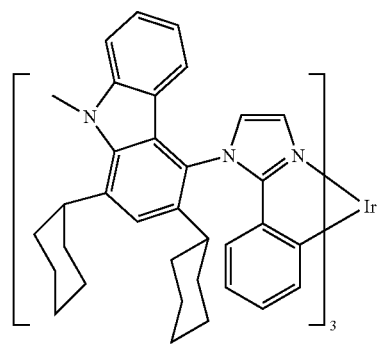
Compound 36
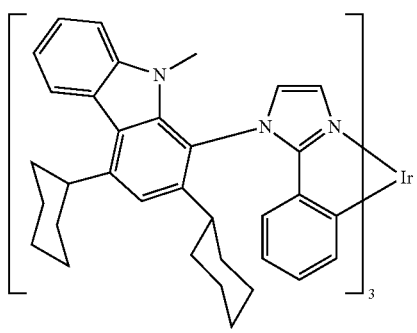
Compound 61
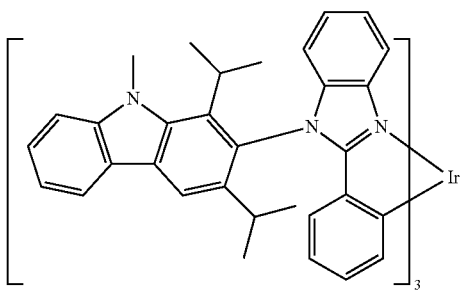
Compound 62
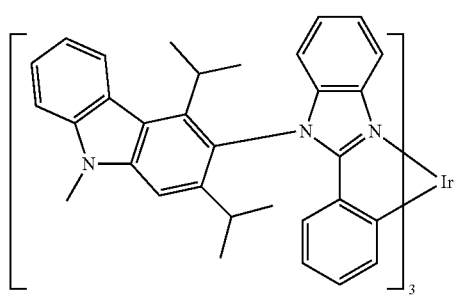
Compound 63
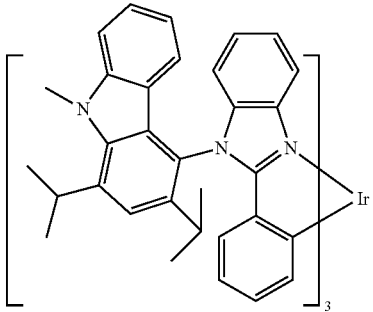
Compound 64
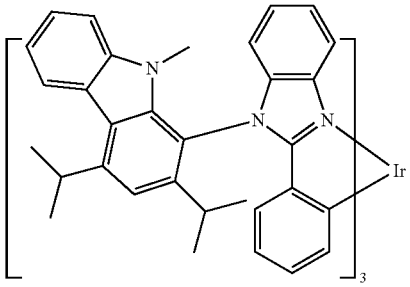
Compound 65
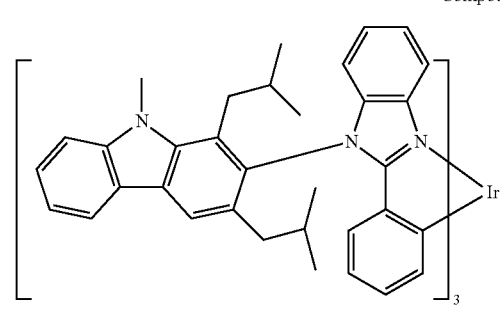
Compound 66
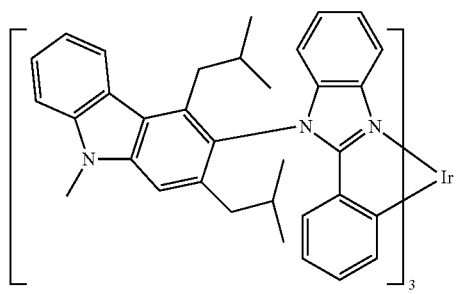

Compound 67
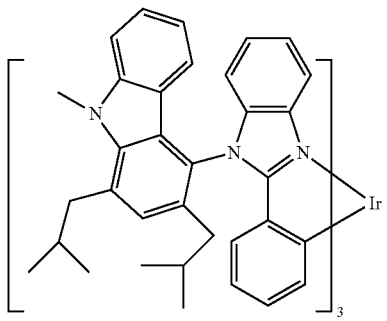

Compound 68
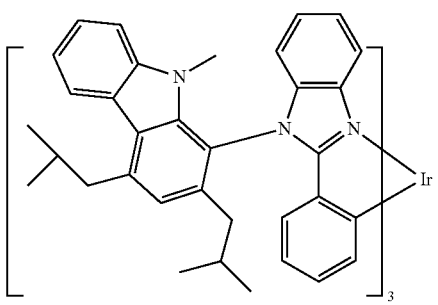

Compound 69
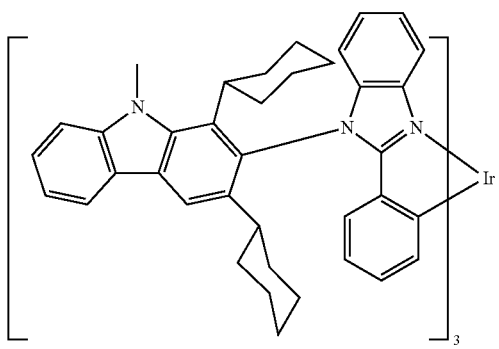

Compound 70
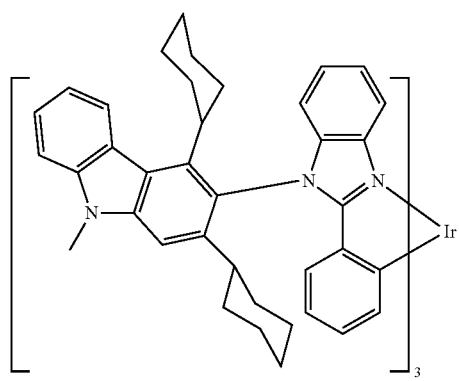

Compound 71
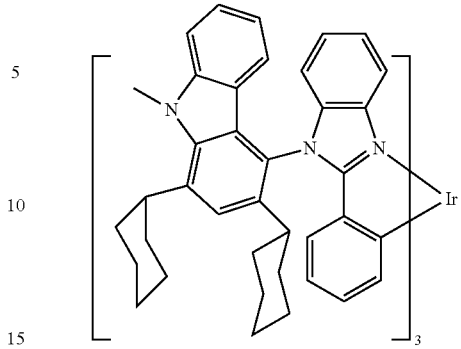

Compound 72
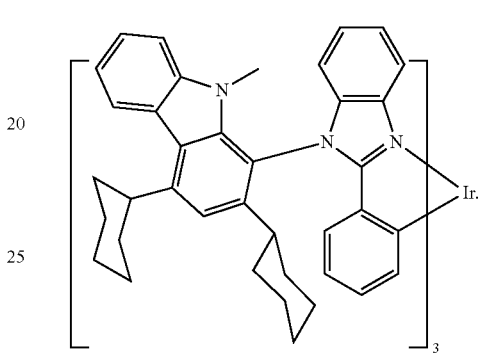

A first device comprising an organic light emitting device is provided. The organic light emitting device further comprises an anode, a cathode, and an organic layer, disposed between the anode and the cathode, the organic layer comprising a compound comprising a ligand L having Formula I, as discussed above. Selections for the substituents described as preferred for the compound including the ligand L having Formula I are also preferred for use in a device that comprises a compound including a ligand L having Formula I. These selections include those described for B, M, $R_C$, $R_A$, and X.

A and B are each independently a 5-membered or 6-membered carbocyclic or heterocyclic ring. Preferably, B is phenyl. $R_A$, $R_B$, $R_C$, and $R_D$ represent mono, di, tri, or tetra substitutions. $R_A$, $R_B$, $R_C$, and $R_D$ are independently selected from hydrogen, halogen, alkyl, alkoxy, amino, alkenyl, alkynyl, aryl and heteroaryl. $R_A$, $R_B$, $R_C$, and $R_D$ are optionally fused. X is selected from the group consisting of CRR', NR, O, and S. R and R' are independently selected from the group consisting of alkyl and aryl. The ligand L is coordinated to a metal M having an atomic number greater than 40. Preferably, M is Ir.

In one aspect, the first device is a consumer product. In one particular aspect, the first device is an organic light emitting device. In another particular aspect, the first device is a display.

In one aspect, the compound is homoleptic. As discussed previously, homoleptic compounds may have many desirable properties. Examples of homoleptic compounds include, without limitation, Compounds 1-72 and Compounds 83-114. In another aspect, the compound is heteroleptic and all of the ligands L in the compound have Formula I. In yet another aspect, the compound is heteroleptic and at least one of the ligands L in the compound have Formula I. Examples of these compounds include, without limitation, Compounds 73-82. As discussed previously, heteroleptic compounds may be advantageously used.

In one aspect, $R_C$ is two alkyl substituents. In another aspect, $R_C$ is two alkyl substituents having 3 or more carbon atoms.

The ring containing $R_C$ may have further substitutions at the positions ortho to the carbon atom connected to A. In one aspect, the ring containing $R_C$ is substituted at one of the positions ortho to the carbon atom connected to A. In another aspect, the ring containing $R_C$ has two substituents located at the positions ortho to the carbon atom connected to A. These compounds may include, for example, Compounds 1, 2 and 4-6. In a further aspect, the ring containing $R_C$ has one substituent that is located at a position ortho to the carbon atom attached to A and the other position ortho to the carbon atom attached to A is occupied by the substituted dibenzo moiety. These compounds may include, for example, Compounds 3, 7, and 11.

In one aspect, $R_C$ is hydrogen.

Particular devices are provided wherein the devices includes a compound selected from the group consisting of Compound 1-Compound 114.

Additionally, devices are provided wherein the organic layer is an emissive layer and the compound comprising a ligand L having Formula I is an emitting dopant. Moreover, the organic layer further comprises a host. Preferably, the host has the formula:

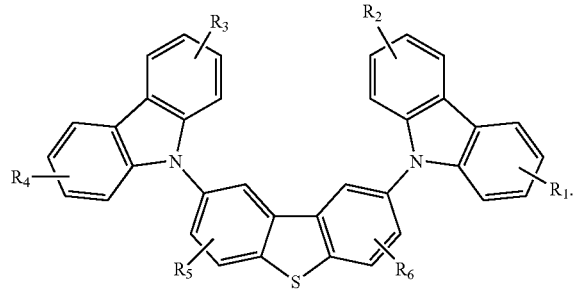

Formula II $R_1$, $R_2$, $R_3$, $R_4$, $R_5$, and $R_6$ are independently selected from the group consisting of hydrogen, alkyl and aryl.

Most preferably, the host is:

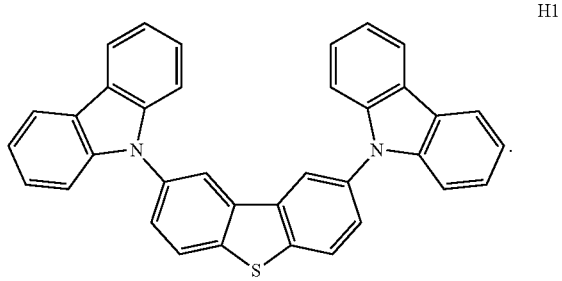 [SMILES: c1ccc2c(c1)c1ccccc1n2-c1ccc2sc3ccc(-n4c5ccccc5c5ccccc54)cc3c2c1]

H1

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluorohydrocarbon polymer | $-(CH_xF_y)_n-$ | Appl. Phys. Lett. 78, 673 (2001) |

TABLE 1-continued
| MATERIAL | EXAMPLES OF MATERIAL | PUBLICATIONS |
|---|---|---|
| Conducting polymers (e.g., PEDOT:PSS, polyaniline, polyphthiophene) | 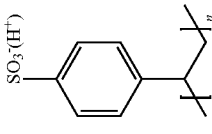 | Synth. Met. 87, 171 (1997) WO2007002683 |
| Phosphonic acid and silane SAMs | 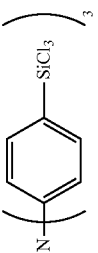 | US20030162053 |
| Triarylamine or polythiophene polymers with conductivity dopants | 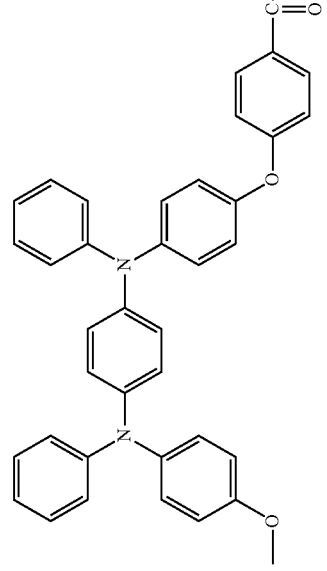 and 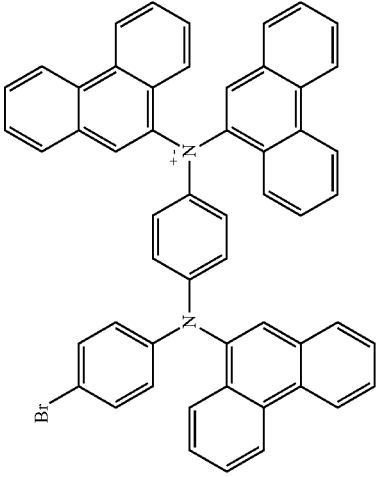 | EA01725079A1 |

TABLE 1-continued
| MATERIAL | EXAMPLES OF MATERIAL | PUBLICATIONS |
|---|---|---|
| Arylamines complexed with metal oxides such as molybdenum and tungsten oxides |  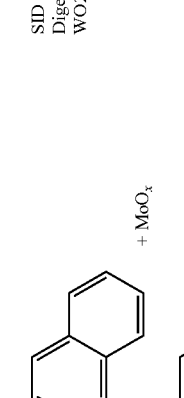 | SID Symposium Digest 37, 923 (2006) WO2009018009 |
| p-type semiconducting organic complexes | 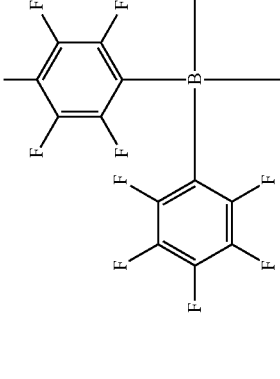 | US20020158242 |

TABLE 1-continued
| MATERIAL | EXAMPLES OF MATERIAL | PUBLICATIONS |
|---|---|---|
| Metal organometallic complexes | 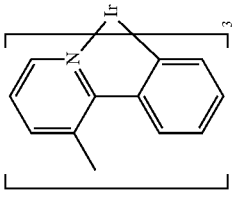 | US20060240279 |
| Cross-linkable compounds | 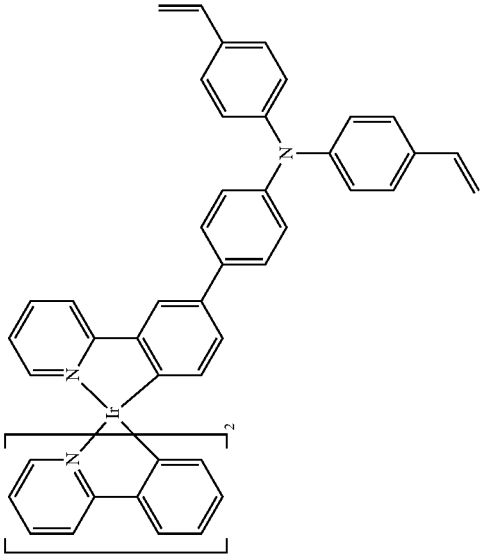 | US20080220265 |
| Hole transporting materials | | |
| Triarylamines (e.g., TPD, α-NPD) | 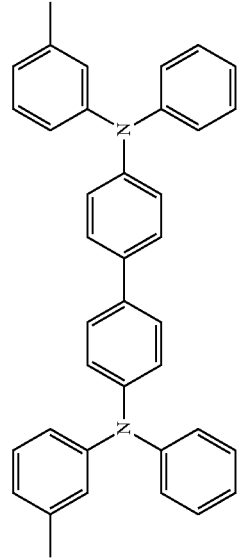 | Appl. Phys. Lett. 51, 913 (1987) |

TABLE 1-continued
| MATERIAL | EXAMPLES OF MATERIAL | PUBLICATIONS |
|---|---|---|
| | 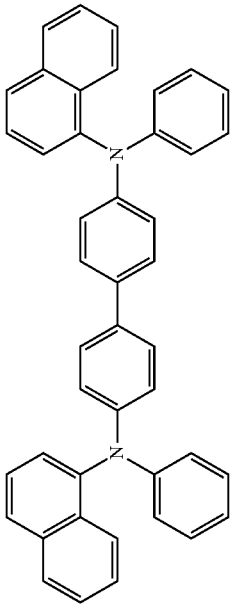 | U.S. Pat. No. 5,061,569<br><br>EP650955 |

| MATERIAL | EXAMPLES OF MATERIAL | PUBLICATIONS |
|---|---|---|
| | | J. Mater. Chem. 3, 319 (1993) |

TABLE 1-continued

TABLE 1-continued
| MATERIAL | EXAMPLES OF MATERIAL | PUBLICATIONS |
|---|---|---|
| | 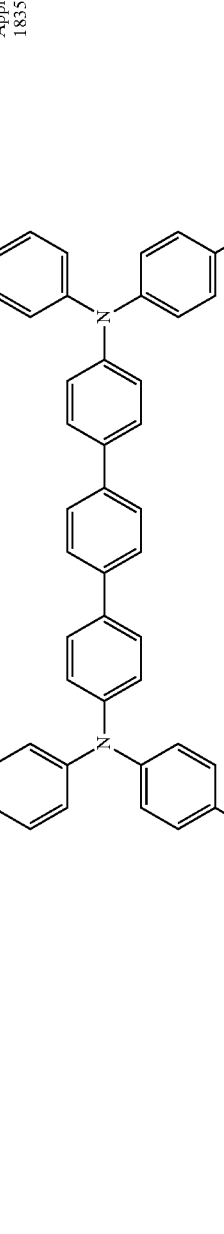 | Appl. Phys. Lett. 90, 183503 (2007) |

TABLE 1-continued
| MATERIAL | EXAMPLES OF MATERIAL | PUBLICATIONS |
|---|---|---|
| | | Appl. Phys. Lett. 90, 183503 (2007) |
| Triaylamine on spirofluorene core | 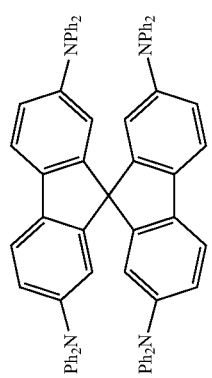 | Synth. Met. 91, 209 (1997) |

TABLE 1-continued
| MATERIAL | EXAMPLES OF MATERIAL | PUBLICATIONS |
|---|---|---|
| Arylamine carbazole compounds | 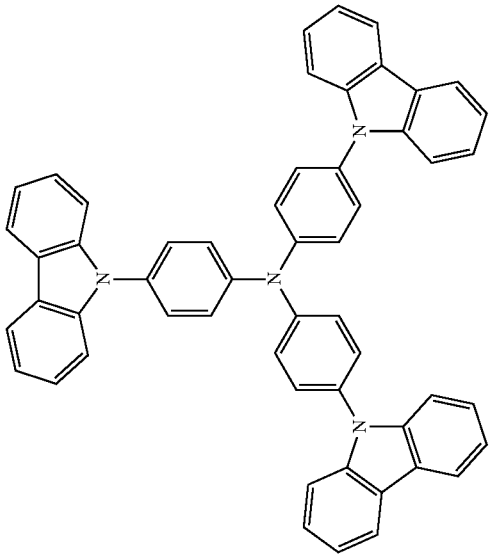 | Adv. Mater. 6, 677 (1994), US20080124572 |
| Triarylamine with (di)benzothiophene/ (di)benzofuran | 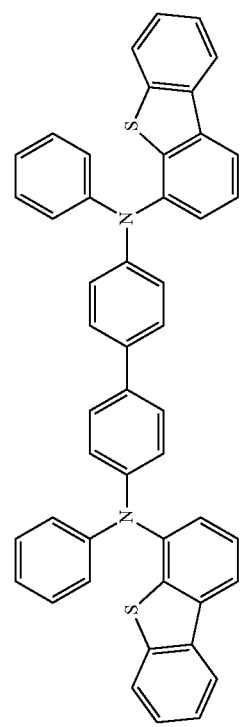 | US20070278938, US20080106190 |

TABLE 1-continued
| MATERIAL | EXAMPLES OF MATERIAL | PUBLICATIONS |
|---|---|---|
| Indolocarbazoles | 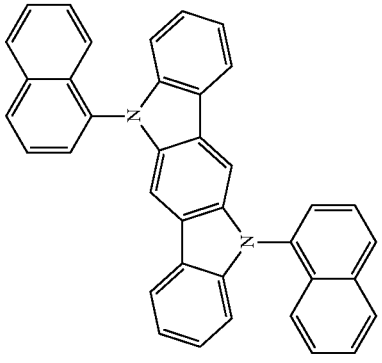 | Synth. Met. 111, 421 (2000) |
| Isoindole compounds | 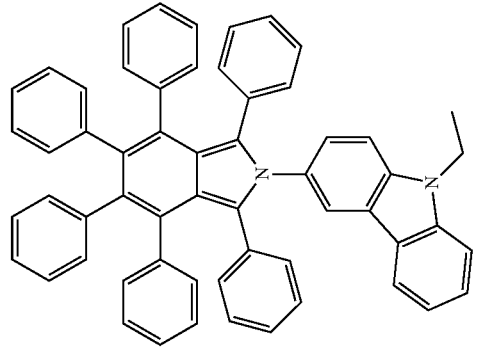 | Chem. Mater, 15, 3148 (2003) |

TABLE 1-continued

| MATERIAL | EXAMPLES OF MATERIAL | PUBLICATIONS |
|---|---|---|
| Metal carbene complexes | | US20080018221 |
| Phosphorescent OLED host materials | | |
| Red hosts | | |
| Arylcarbazoles | | Appl. Phys. Lett. 78, 1622 (2001) |
| | | Nature 395, 151 (1998) |
| Metal 8-hydroxyquinolates (e.g., Alq$_3$, BAlq) | | US2006202194 |

TABLE 1-continued
| MATERIAL | EXAMPLES OF MATERIAL | PUBLICATIONS |
|---|---|---|
| | 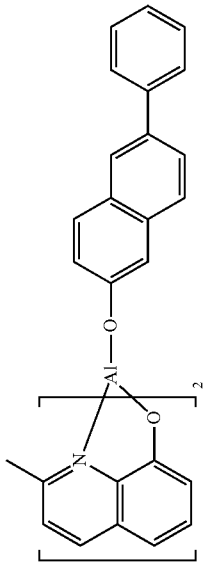 | WO2005014551 |
| | 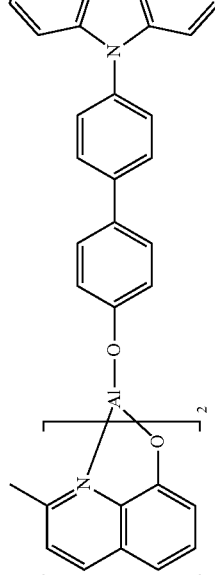 | WO2006072002 |
| Metal phenoxybenzothiazole compounds | 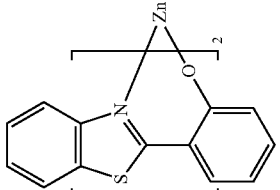 | Appl. Phys. Lett. 90, 123509 (2007) |
| Conjugated oligomers and polymers (e.g., polyfluorene) | 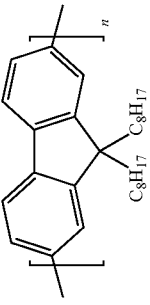 | Org. Electron. 1, 15 (2000) |

TABLE 1-continued
| MATERIAL | EXAMPLES OF MATERIAL | PUBLICATIONS |
|---|---|---|
| Aromatic fused rings | 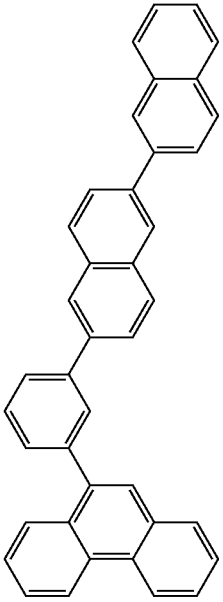 | WO2009066779, WO2009066778, WO2009063833, US20090045731, US20090045730, WO2009008311, US20090008605, US20090009065 |
| Zinc complexes | 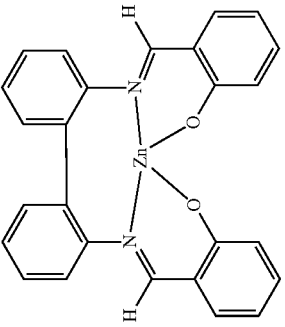 | WO2009062578 |
| Green hosts | | |
| Arylcarbazoles | 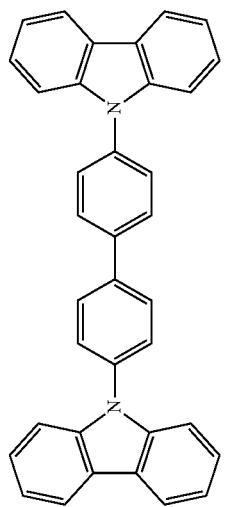 | Appl. Phys. Lett. 78, 1622 (2001) |
| | 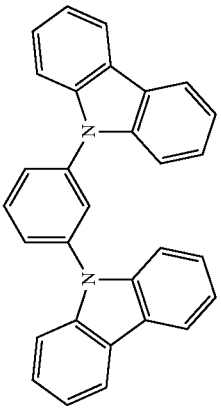 | US20030175553 |

TABLE 1-continued
| MATERIAL | EXAMPLES OF MATERIAL | PUBLICATIONS |
|---|---|---|
| | 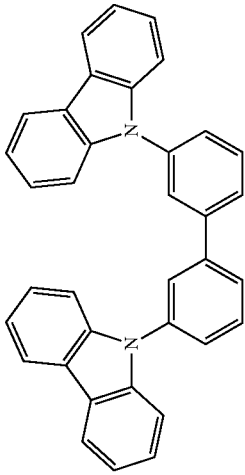 | WO2001039234 |
| Aryltriphenylene compounds | 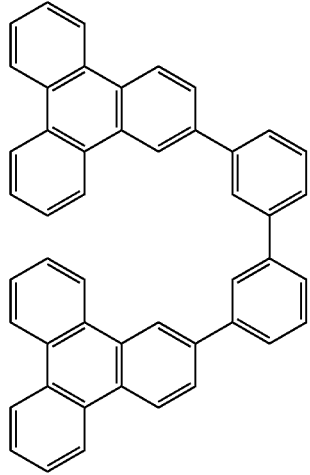 | US20060280965 |
| | 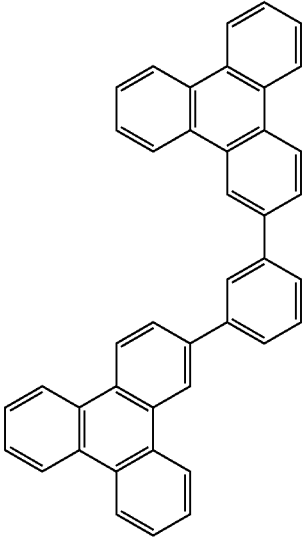 | US20060280965 |

TABLE 1-continued

| MATERIAL | EXAMPLES OF MATERIAL | PUBLICATIONS |
|---|---|---|
| | | WO2009021126 |
| Donor acceptor type molecules | | WO2008056746 |
| Aza-carbazole/DBT/DBF | | JP2008074939 |

TABLE 1-continued
| MATERIAL | EXAMPLES OF MATERIAL | PUBLICATIONS |
|---|---|---|
| Polymers (e.g., PVK) | 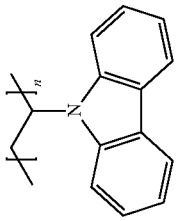 | Appl. Phys. Lett. 77, 2280 (2000) |
| Spirofluorene compounds | 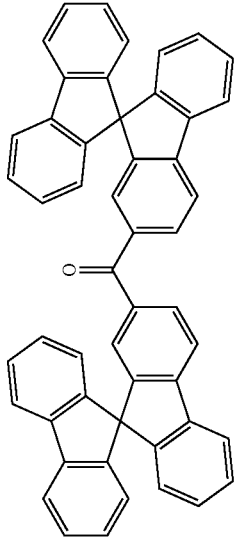 | WO2004093207 |
| Metal phenoxybenzooxazole compounds | 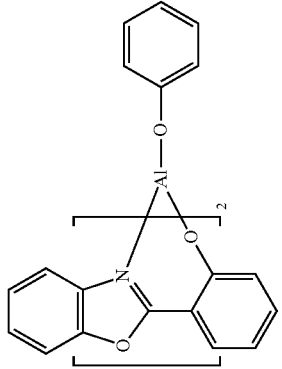 | WO2005089025 |
| |  | WO2006132173 |

TABLE 1-continued
| MATERIAL | EXAMPLES OF MATERIAL | PUBLICATIONS |
|---|---|---|
| | 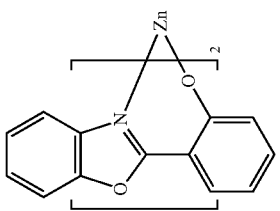 | JP200511610 |
| Spirofluorene-carbazole compounds | 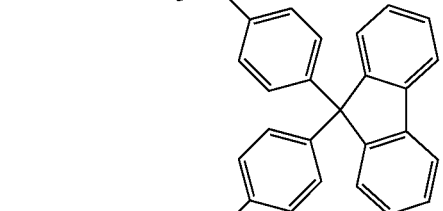 | JP2007254297<br><br>JP2007254297 |

TABLE 1-continued
| MATERIAL | EXAMPLES OF MATERIAL | PUBLICATIONS |
|---|---|---|
| Indolocabazoles | 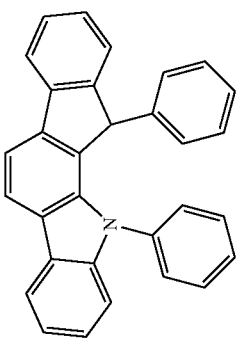 | WO2007063796 |
| | 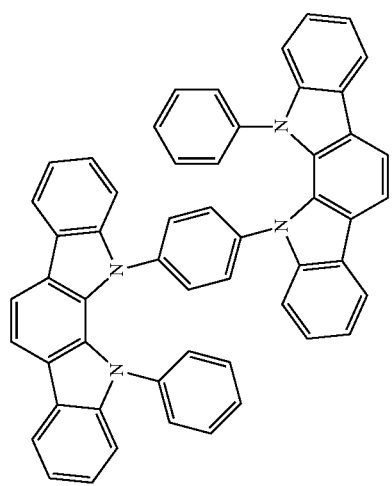 | WO2007063754 |
| 5-member ring electron deficient heterocycles (e.g. triazole, oxadiazole) | 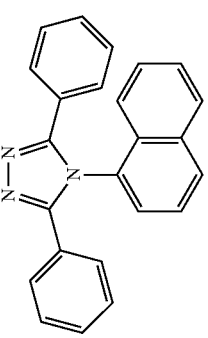 | J. Appl. Phys. 90, 5048 (2001) |

TABLE 1-continued
| MATERIAL | EXAMPLES OF MATERIAL | PUBLICATIONS |
|---|---|---|
| | 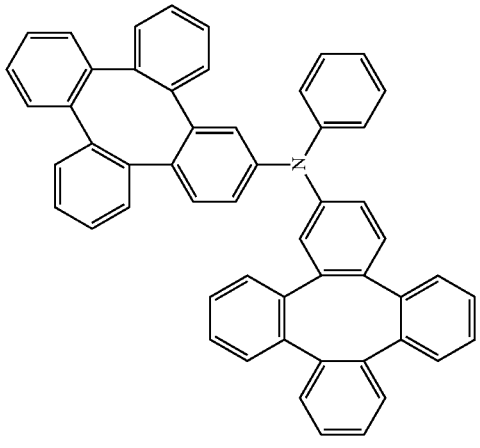 | WO2004107822 |
| Tetraphenylene complexes | 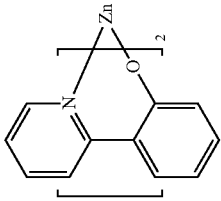 | US2005011240 |
| Metal phenoxypyridine compounds | 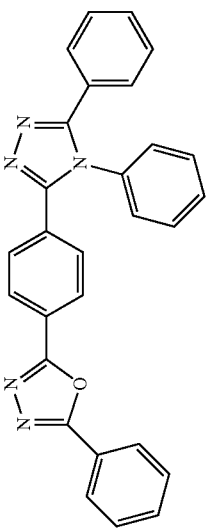 | WO2005030900 |

TABLE 1-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |
| Blue hosts | | |
| Arylcarbazoles | | Appl. Phys. Lett. 82, 2422 (2003) |
| | | US20070190359 |
| Dibenzothiophene/Dibenzofuran-carbazole compounds | | WO2006114966, US20090167162 |

TABLE 1-continued
| MATERIAL | EXAMPLES OF MATERIAL | PUBLICATIONS |
|---|---|---|
| | 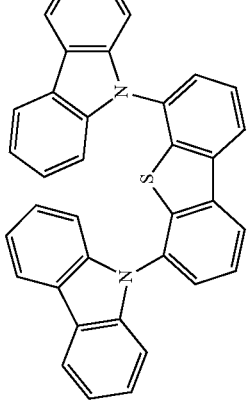 | US20090167162 |
| | 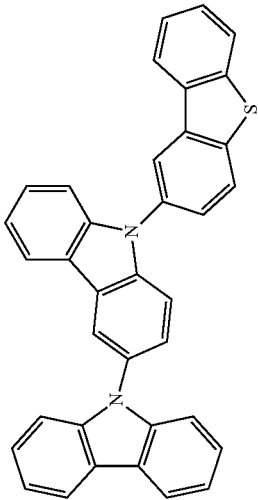 | WO2009086028 |
| | 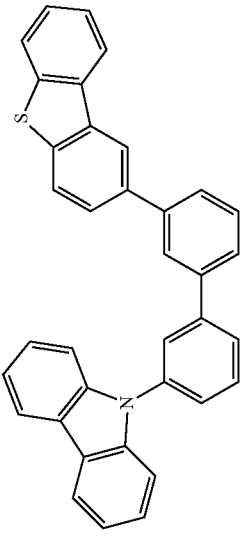 | US20090030202, US20090017330 |

TABLE 1-continued
| MATERIAL | EXAMPLES OF MATERIAL | PUBLICATIONS |
|---|---|---|
| Silicon aryl compounds | 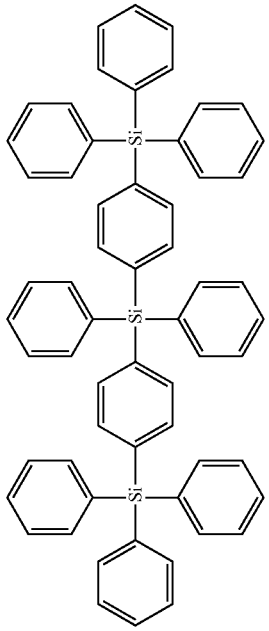 | US20050238919 |
| | 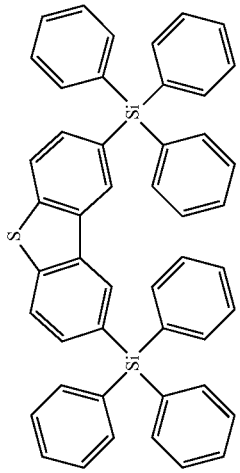 | WO2009003898 |
| Silicon/Germanium aryl compounds | 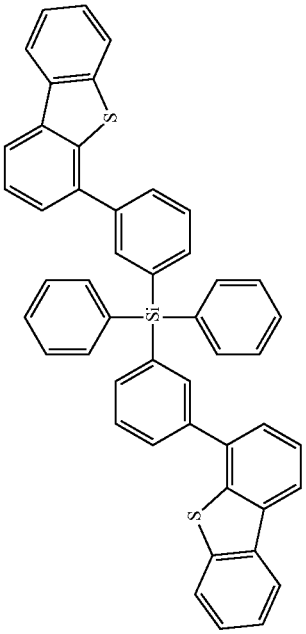 | EP2034538A |
| Aryl benzoyl ester | 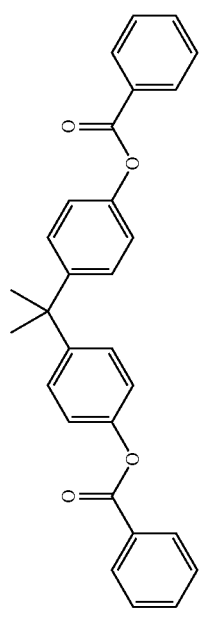 | WO2006100298 |

TABLE 1-continued

| MATERIAL | EXAMPLES OF MATERIAL | PUBLICATIONS |
| --- | --- | --- |
| High triplet metal organometallic complex | | U.S. Pat. No. 7,154,114 |
| Phosphorescent dopants | | |
| Red dopants | | |
| Heavy metal porphyrins (e.g. PtOEP) | | Nature 395, 151 (1998) |
| Iridium(III) organometallic complexes | | Appl. Phys. Lett. 78, 1622 (2001) |

TABLE 1-continued

| MATERIAL | EXAMPLES OF MATERIAL | PUBLICATIONS |
|---|---|---|
| | | US2006835469 |
| | | US2006835469 |
| | | US20060202194 |

TABLE 1-continued

| MATERIAL | EXAMPLES OF MATERIAL | PUBLICATIONS |
|---|---|---|
| | | US20060202194 |
| | | US20070087321 |
| | | US20070087321 |

TABLE 1-continued

| MATERIAL | EXAMPLES OF MATERIAL | PUBLICATIONS |
|---|---|---|
| | | Adv. Mater, 19, 739 (2007) |
| | | WO2009100991 |
| | | WO2008101842 |

TABLE 1-continued

| MATERIAL | EXAMPLES OF MATERIAL | PUBLICATIONS |
|---|---|---|
| Platinum(II) organometallic complexes | | WO2003040257 |
| Osminum(III) complexes | | Chem. Mater. 17, 3532 (2005) |
| Ruthenium(II) complexes | | Adv. Mater. 17, 1059 (2005) |
| Rhenium(I), (II), and (III) complexes | | US20050244673 |

TABLE 1-continued
| MATERIAL | EXAMPLES OF MATERIAL | PUBLICATIONS |
|---|---|---|
| Green dopants | | |
| Iridium(III) organometallic complexes | 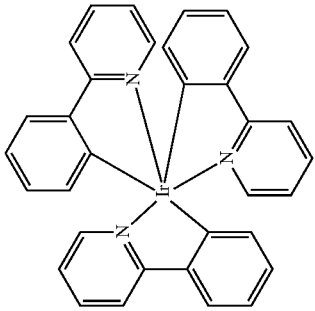 and its derivatives | Inorg. Chem. 40, 1704 (2001) |
| | 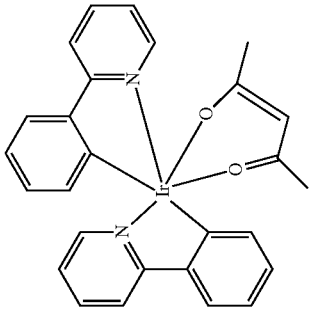 | US20020034656 |

| MATERIAL | EXAMPLES OF MATERIAL | PUBLICATIONS |
|---|---|---|
| | 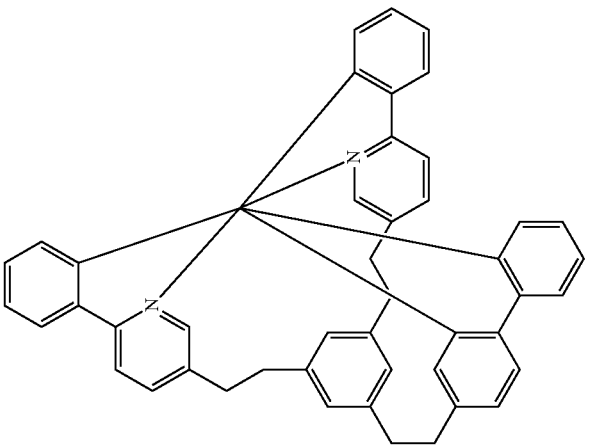 | U.S. Pat. No. 7,332,232<br><br>US2009108737 |

TABLE 1-continued
| MATERIAL | EXAMPLES OF MATERIAL | PUBLICATIONS |
|---|---|---|
| | 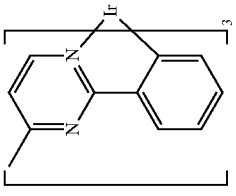 | US20090039776 |
| | 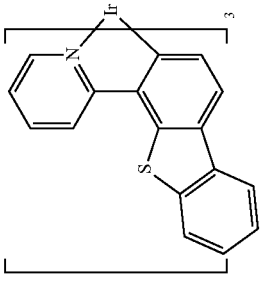 | U.S. 6,921,915 |
| | 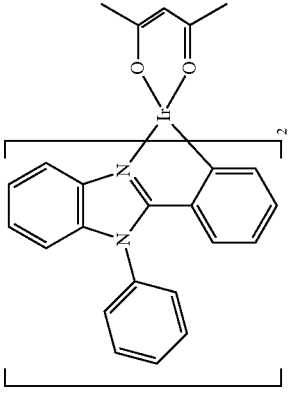 | U.S. Pat. No. 6,687,266 |

TABLE 1-continued

| MATERIAL | EXAMPLES OF MATERIAL | PUBLICATIONS |
|---|---|---|
| | | Chem. Mater, 16, 2480 (2004) |
| | | US20070190359 |
| | | US 20060008670<br>JP2007123392 |
| | | Adv. Mater. 16, 2003 (2004) |

TABLE 1-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |

TABLE 1-continued
| MATERIAL | EXAMPLES OF MATERIAL | PUBLICATIONS |
|---|---|---|
| | 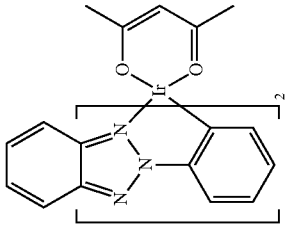 | US20080015355 |
| Monomer for polymeric metal organometallic compounds | 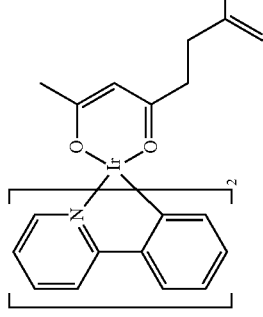 | US7250226, US7396598 |
| Pt(II) organometallic complexes, including polydentated ligands | 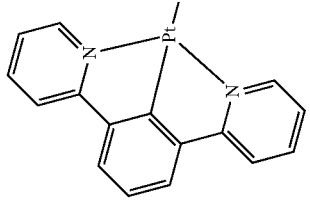 | Appl. Phys. Lett. 86, 153505 (2005) |

TABLE 1-continued
| MATERIAL | EXAMPLES OF MATERIAL | PUBLICATIONS |
|---|---|---|
| | 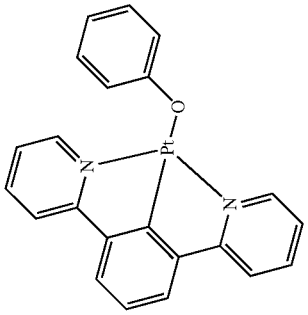 | Appl. Phys. Lett. 86, 153505 (2005) |
| | | Chem. Lett. 34, 592 (2005) |
| | 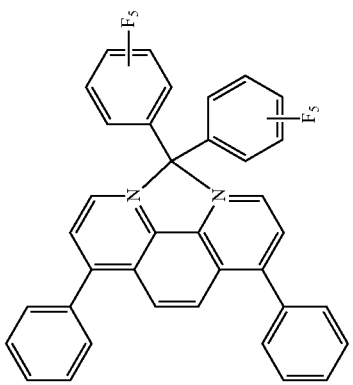 | WO2002015645 |

TABLE 1-continued
| MATERIAL | EXAMPLES OF MATERIAL | PUBLICATIONS |
|---|---|---|
| | 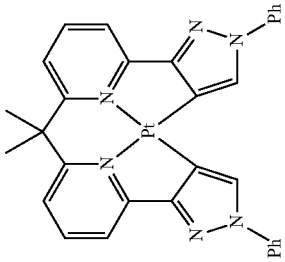 | US20060263635 |
| Cu complexes | 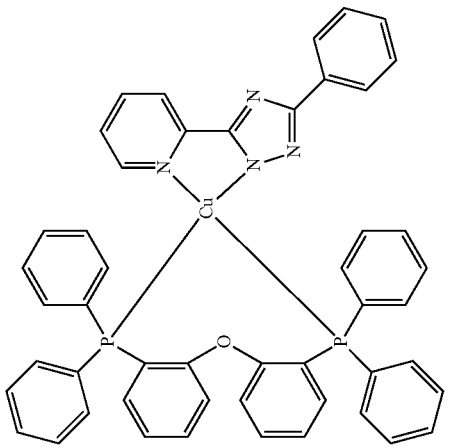 | WO2009000673 |
| Gold complexes | 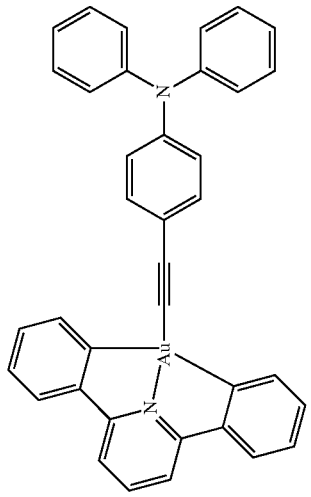 | Chem. Commun. 2906 (2005) |

TABLE 1-continued
| MATERIAL | EXAMPLES OF MATERIAL | PUBLICATIONS |
|---|---|---|
| Rhenium(III) complexes | 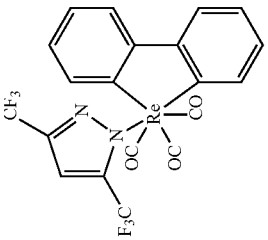 | Inorg. Chem. 42, 1248 (2003) |
| Deuterated organometallic complexes | 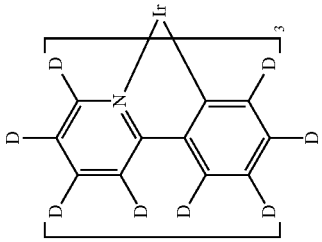 | US2003013865 7 |
| Organometallic complexes with two or more metal centers | 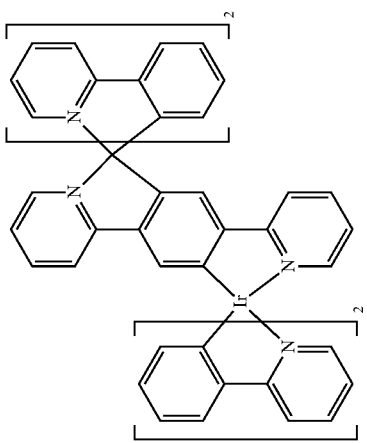 | US2003015280 2 |

TABLE 1-continued
| MATERIAL | EXAMPLES OF MATERIAL | PUBLICATIONS |
|---|---|---|
| | 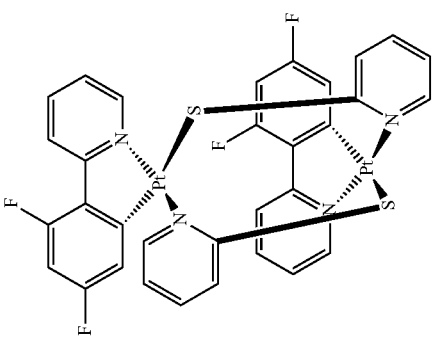 | U.S. Pat. No. 7,090,928 |
| Blue dopants | | |
| Iridium(III) organometallic complexes | 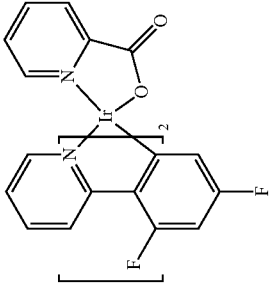 | WO2002002714<br><br>WO2006009024 |

TABLE 1-continued
| MATERIAL | EXAMPLES OF MATERIAL | PUBLICATIONS |
|---|---|---|
| | 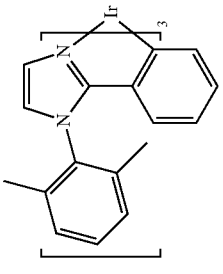 | US20060251923 |
| | 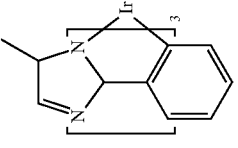 | U.S. Pat. No. 7,393,599, WO2006056418, US20050260441, WO2005019373 |
| | 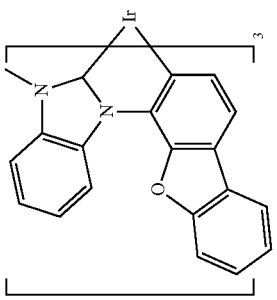 | U.S. Pat. No. 7,534,505 |

| MATERIAL | EXAMPLES OF MATERIAL | PUBLICATIONS |
|---|---|---|
| | 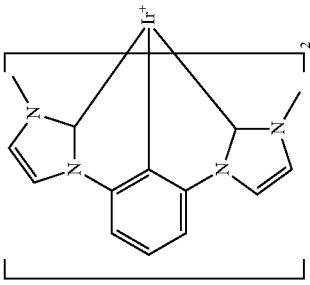 | U.S. Pat. No. 7,445,855 |
| | 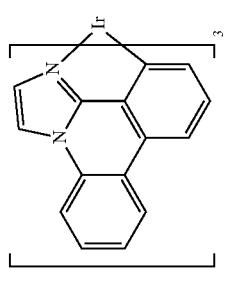 | US20070190359, US20080297033 |
| | 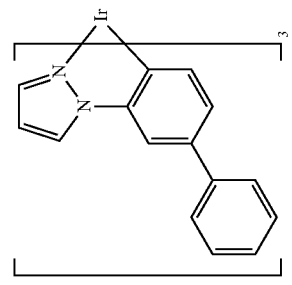 | U.S. Pat. No. 7,338,722 |

TABLE 1-continued
| MATERIAL | EXAMPLES OF MATERIAL | PUBLICATIONS |
|---|---|---|
| | 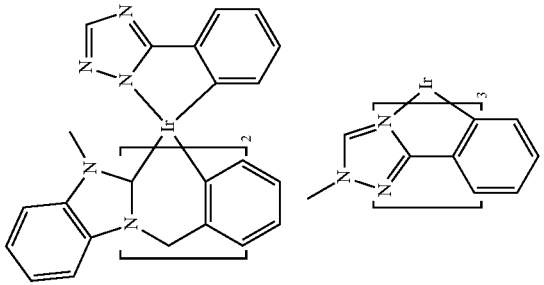 | US20020134984<br><br>Angew. Chem. Int. Ed. 47, 1 (2008)<br><br>Chem. Mater. 18, 5119 (2006) |

TABLE 1-continued
| MATERIAL | EXAMPLES OF MATERIAL | PUBLICATIONS |
|---|---|---|
| | 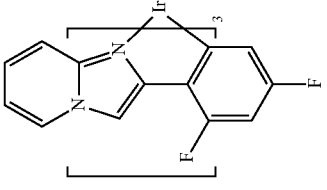 | Inorg. Chem. 46, 4308 (2007) |
| | 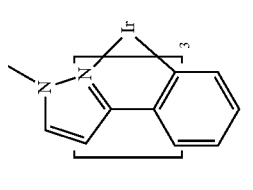 | WO2005123873 |
| | 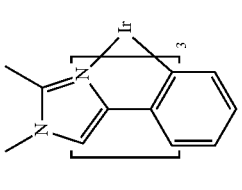 | WO2005123873 |
| | 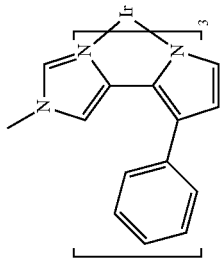 | WO2007004380 |

TABLE 1-continued
| MATERIAL | EXAMPLES OF MATERIAL | PUBLICATIONS |
|---|---|---|
| Osmium(II) complexes | 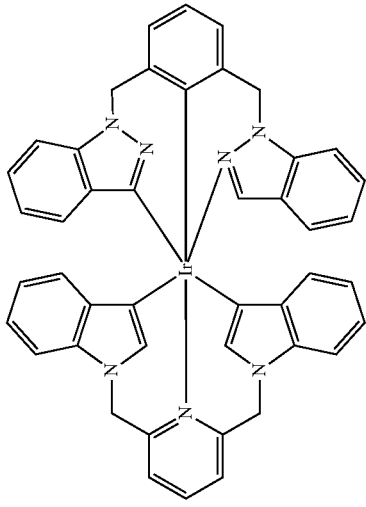 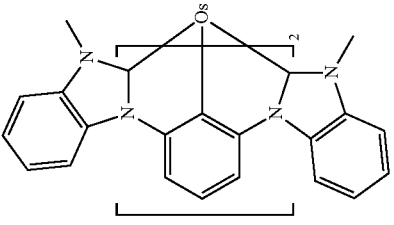 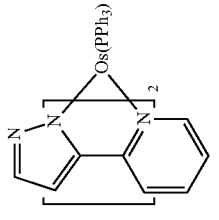 | WO2006082742<br><br>U.S. Pat. No. 7279704<br><br>Organometallics 23, 3745 (2004) |

TABLE 1-continued

| MATERIAL | EXAMPLES OF MATERIAL | PUBLICATIONS |
|---|---|---|
| Gold complexes | | Appl. Phys. Lett. 74, 1361 (1999) |
| Platinum(II) complexes | | WO2006098120, WO2006103874 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |

TABLE 1-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 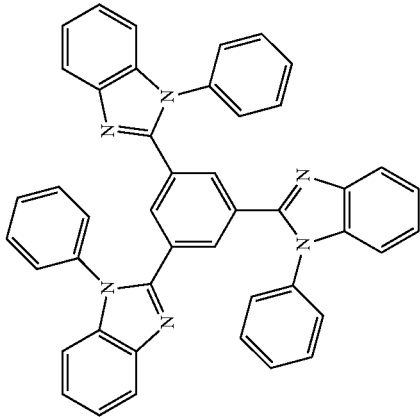 | Appl. Phys. Lett. 81, 162 (200) |
| Triphenylene compounds | 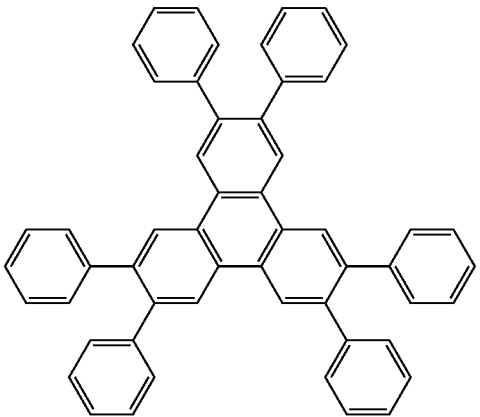 | US20050025993 |

TABLE 1-continued
| MATERIAL | EXAMPLES OF MATERIAL | PUBLICATIONS |
|---|---|---|
| Fluorinated aromatic compounds | 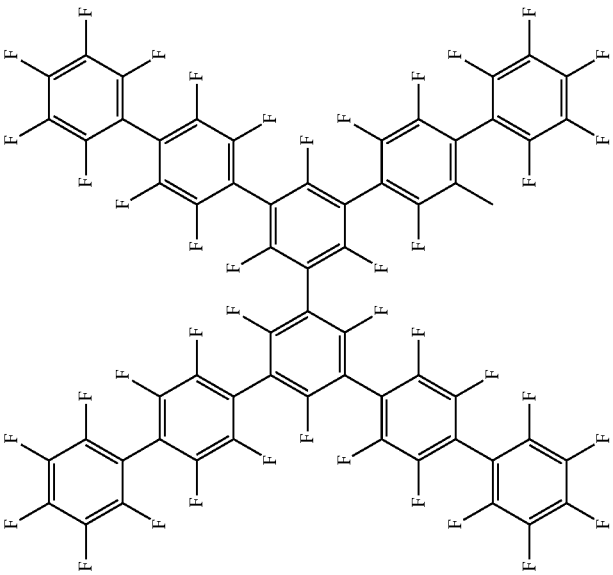 | Appl. Phys. Lett. 79, 156 (2001) |
| Phenothiazine-S-oxide | 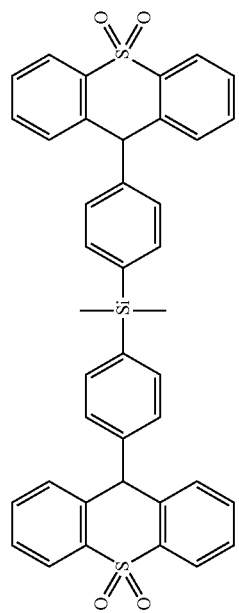 | WO2008132085 |

TABLE 1-continued
| MATERIAL | EXAMPLES OF MATERIAL | PUBLICATIONS |
|---|---|---|
| Electron transporting materials | | |
| Anthracene-benzoimidazole compounds | 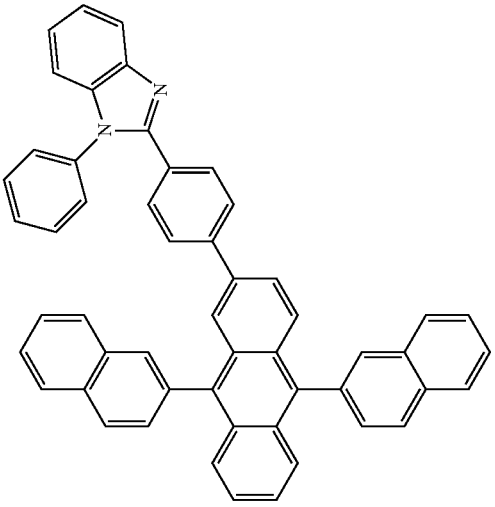 | WO2003060956 |
| | 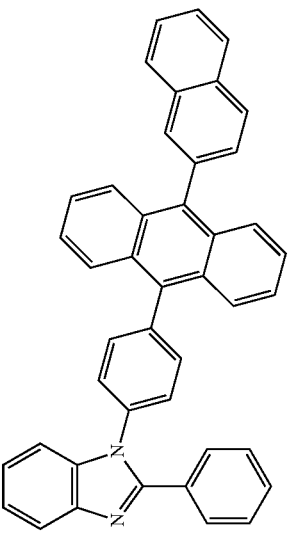 | US20090179554 |

TABLE 1-continued
| MATERIAL | EXAMPLES OF MATERIAL | PUBLICATIONS |
|---|---|---|
| Aza triphenylene derivatives | 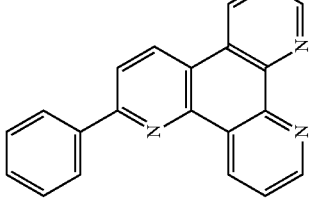 | US20090115316 |
| Anthracene-benzothiazole compounds | 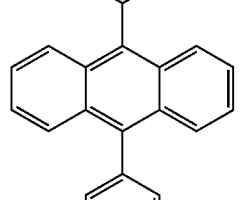 | Appl. Phys. Lett. 89, 063504 (2006) |
| Metal 8-hydroxyquinolates (e.g., Alq$_3$, Zrq$_4$) | 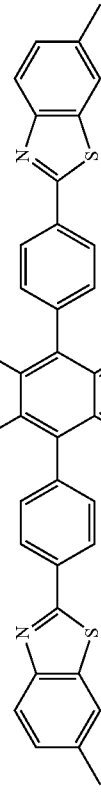 | Appl. Phys. Lett. 51, 913 (1987)<br>U.S. Pat. No. 7,230,107 |
| Metal hydroxybenoquinolates | 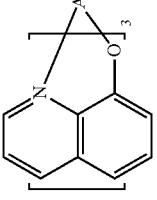 | Chem. Lett. 5, 905 (1993) |

TABLE 1-continued
| MATERIAL | EXAMPLES OF MATERIAL | PUBLICATIONS |
|---|---|---|
| Bathocuprine compounds such as BCP, BPhen, etc | 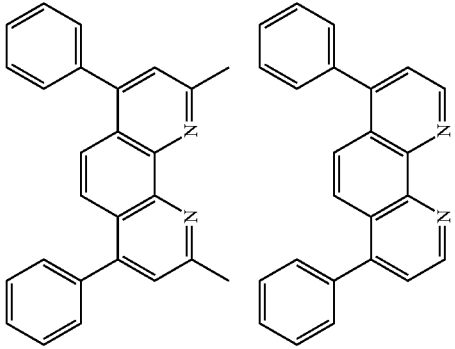 | Appl. Phys. Lett. 91, 263503 (2007)<br><br>Appl. Phys. Lett. 79, 449 (2001)<br><br>Appl. Phys. lett. 74, 865 (1999) |
| 5-member ring electron deficient heterocycles (e.g. triazole, oxadiazole, imidazole, benzoimidazole) | 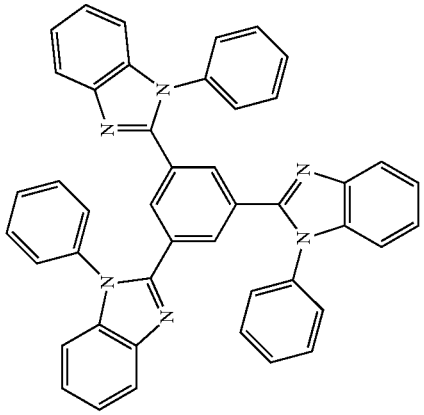<br>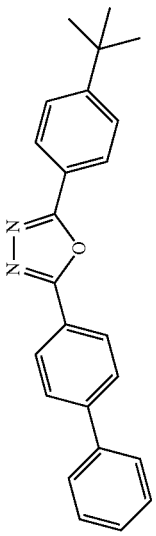 | Appl. Phys. Lett. 55, 1489 (1989) |

TABLE 1-continued
| MATERIAL | EXAMPLES OF MATERIAL | PUBLICATIONS |
|---|---|---|
| | 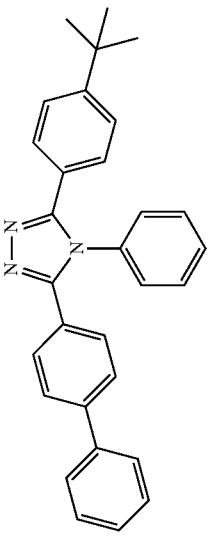 | Jpn. J. Apply. Phys. 32, L917 (1993) |
| Silole compounds | 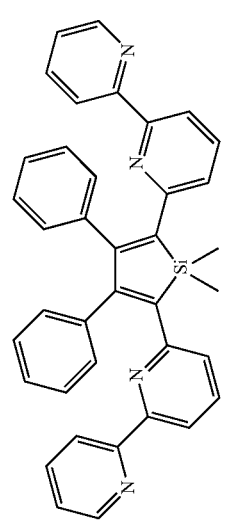 | Org. Electron. 4, 113 (2003) |
| Arylborane compounds | 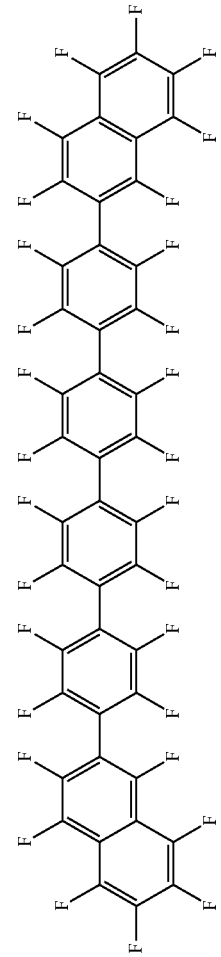 | J. Am. Chem. Soc. 120, 9714 (1998) |
| Fluorinated aromatic compounds | | J. Am. Chem. Soc. 122, 1832 (2000) |

TABLE 1-continued
| MATERIAL | EXAMPLES OF MATERIAL | PUBLICATIONS |
|---|---|---|
| Fullerene (e.g., C60) | 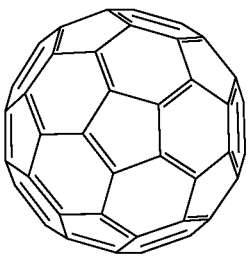 | US20090101870 |
| Triazine complexes | 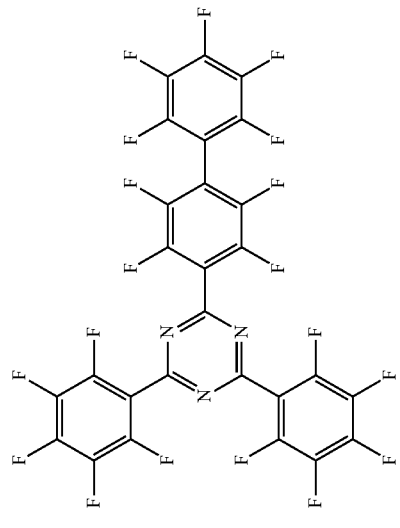 | US20040036077 |
| Zn (N^N) complexes | 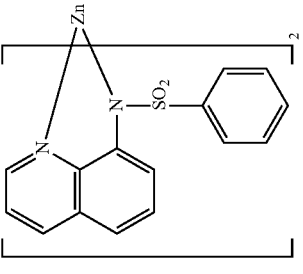 | U.S. Pat. No. 6,528,187 |

EXPERIMENTAL

Compound Examples

Several of the compounds were synthesized as follows:

Example 1

Synthesis of Compound 1

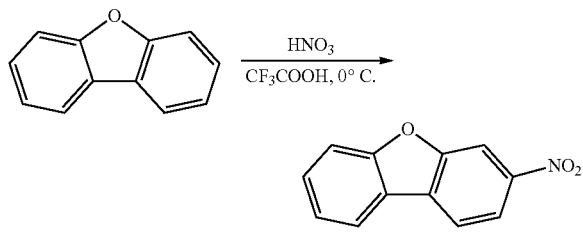

Synthesis of 3-nitrodibenzofuran

Dibenzofuran (30 g, 178 mmol) was dissolved in 276 ml, trifluoroacetic acid (TFA) and cooled in ice water bath. Fuming nitric acid 15 g (~17 mL) was diluted with 3 mL water and then dissolved in 25 mL TFA and added to dibenzofuran solution drop wise. Reaction takes place almost instantly and a thick light green color precipitate forms. At the end of addition, flask was stirred for 20 minutes more and then poured over ice. Light green precipitate was then filtered off, washed with 2 M NaOH, dried and recrystallized from boiling ethanol 30 g (76%) of product was obtained.

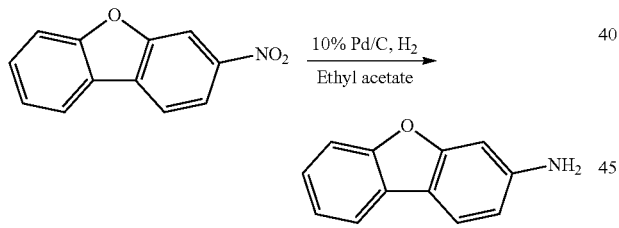

Synthesis of 3-Aminodibenzofuran 3-nitrodibenzofuran (30 g, 141 mmol) was stirred in 500 mL ethyl acetate and 3 g of 10% Pd/C were added to the slurry. Reaction mixture was hydrogenated for 30 minutes at 50 psi $H_2$ pressure. Reaction mixture was filtered through a small Celite pad. Filtrate was concentrated under reduced pressure and performed silica gel column using 9:1 DCM/Hexanes as eluent. Final isolated amount was 14.5 g (56% yield).

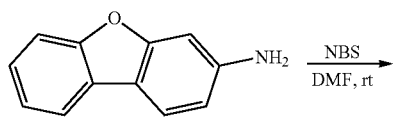

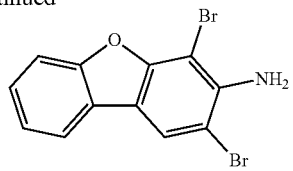

Synthesis of 2,4-Dibromo-3-Aminodibenzofuran

Dibenzofuran-3-amine (5.9 g, 32.2 mmol) was dissolved in dry DMF (25 mL) and at room temp a solution of N-bromosuccinamide (NBS) in DMF (25 mL) was added drop wise. The reaction mixture was stirred for 1 h, precipitate was formed which was filtered and washed with water several times. The precipitate was dissolved in methylene chloride dried over sodium sulfate, concentrated under reduced pressure. The crude product was purified by short silica column using hexanes and ethyl acetate as eluents to give 10.0 g (94% yield) of title compound.

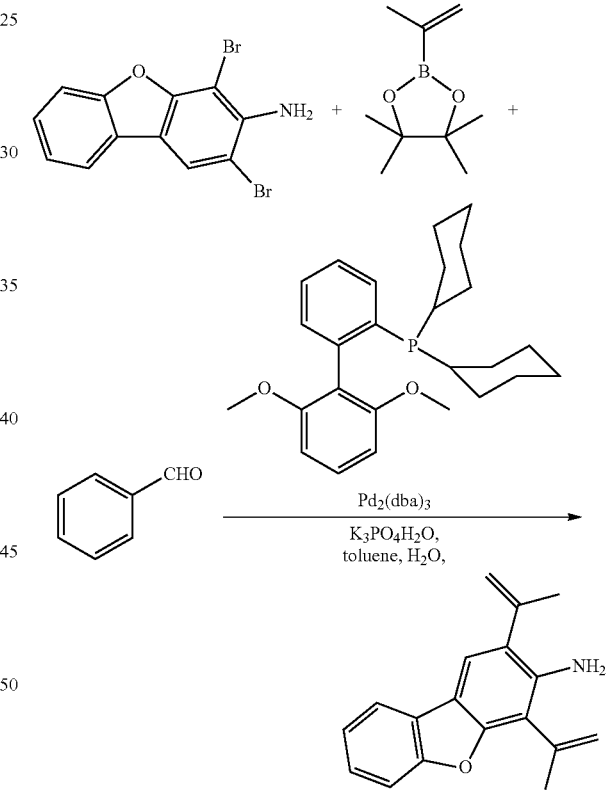

Synthesis of 2,4-bis(isopropenyl)dibenzo[b,d]furan-3-amine

A mixture of 2,4-dibromodibenzo[b,d]furan-3-amine (14.5 g, 42.5 mmol), benzaldehyde (4.96 g, 46.8 mmol), 4,4,5,5-tetramethyl-2-(prop-1-en-2-yl)-1,3,2-dioxaborolane (21.44 g, 128 mmol), and potassium phosphate (45.1 g, 213 mmol) in 250 mL of toluene and 25 mL of $H_2O$ was bubbled with $N_2$ for 20 minutes. Dicyclohexyl(2',6'-dimethoxybiphenyl-2-yl)phosphine (0.698 g, 1.701 mmol) and $Pd_2(dba)_3$ (0.389 g, 0.425 mmol) were then added, and the mixture was heated to reflux under N₂ for 14 h. GC-MS indicated the reaction was done. After cooled to room temperature, the toluene layer was decanted. The aqueous layer was washed with toluene, and the organic layers were combined. 60 mL of concentrated HCl was added. The mixture was stirred at room temperature for 1 h. The precipitated was collected by filtration. The solid was dissolved in dichloromethane and neutralized with NaOH and dried over magnesium sulfate. After solvent evaporation, the residue was purified by column chromatography using 5-10% of ethyl acetate/hexanes as solvent. 6.6 g (59% yield) of product was obtained after purification.

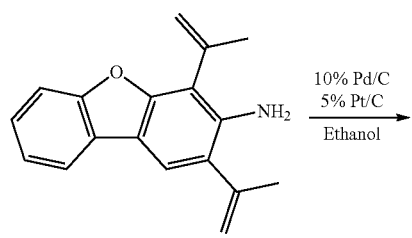

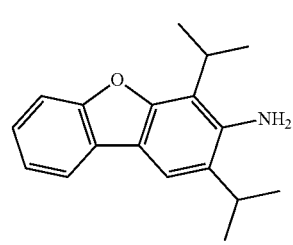

Synthesis of 2,4-diisopropyldibenzo[b,d]furan-3-amine 2,4-bis (isopropenyl)dibenzo[b,d]furan-3-amine (6.6 g, 25 mmol) was dissolved in ethanol (150 mL) and to it were added 10% Pd/C (1.5 g) and 5% Pt/C (1.5 g) and hydrogenated at 50 psi of H₂ over night. GC indicated complete conversion of olefin to alkane. The reaction mixture was filtered through a Celite pad and washed with methylene chloride. The filtrate was concentrated to produce 6 g (90% yield) of desired product.

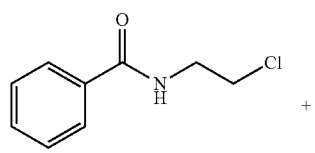

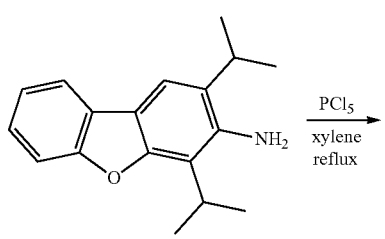

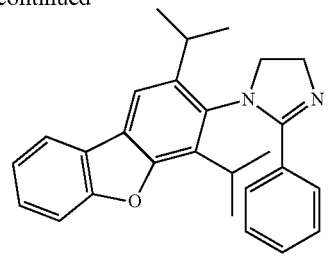

Synthesis of 1-(2,4-diisopropyldibenzo[b,d]furan-3-yl)-2-phenyl-4,5-dihydro-1H-imidazole N-(2-chloroethyl)benzamide (4.12 g, 22.44 mmol) and phosphorous pentachloride (7.01 g, 33.7 mmol) were refluxed in m-xylene under nitrogen for 2 h. The reaction mixture was cooled to room temperature. To the reaction was then added 2,4-diisopropyldibenzo[b,d]furan-3-amine (6 g, 22.44 mmol). The reaction was refluxed for 16 h. After cooled to room temperature, the precipitate was collected by filtration, and washed thoroughly with toluene and hexanes. Sodium hydroxide solution was added to the solid and then ethyl acetate. The organic layer was separated and dried over MgSO₄. The solvent was evaporated. 7.4 g (83% yield) of product was obtained.

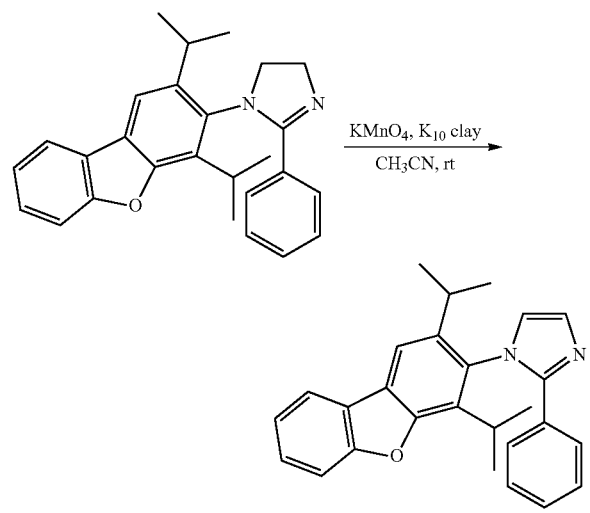

Synthesis of 1-(2,4-diisopropyldibenzo[b,d]furan-3-yl)-2-phenyl-1H-imidazole 1-(2,4-diisopropyldibenzo[b,d]furan-3-yl)-2-phenyl-4,5-dihydro-1H-imidazole (7.4 g, 18.66 mmol) was dissolved in 200 mL of acetonitrile and 100 mL of dichloromethane. Potassium Permanganate (5.90 g, 37.3 mmol) and Clay K10 (12 g, 30.7 mmol) were ground in a mortar. The solid was then added carefully to the solution. Heat was generated after a few minutes. The reaction was monitored by TLC. The reaction was quenched with methanol after 1.5 h. The reaction mixture was filtered through Celite. The solvent was evaporated and the residue was purified by column. 5.3 g (72% yield) of pure product was obtained.

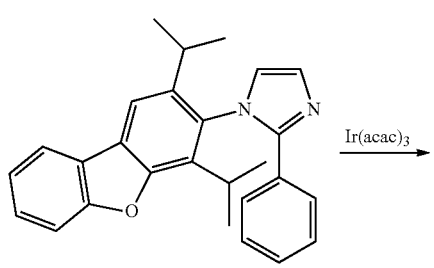

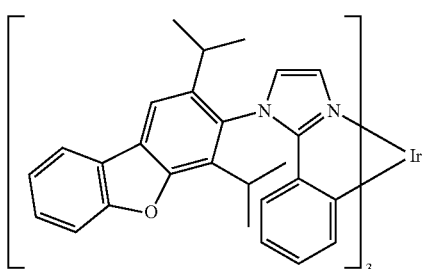

Compound 1

Synthesis of Compound 1

1-(2,4-diisopropyldibenzo[b,d]furan-3-yl)-2-phenyl-1H-imidazole (1.3 g, 3.30 mmol) and Tris(acetylacetonate)iridium (III) (0.323 g, 0.659 mmol) were added to a Schlenk tube. 1 mL of tridecane was added. The reaction flask was evacuated and backfilled with nitrogen. The process was repeated 3 times. The reaction was heated up to 255 degrees under nitrogen for 68 h. After completion, the reaction mixture was diluted with dichloromethane and coated on Ceilte. The product was purified by column using 2:3 dichloromethane and hexanes as solvent. 1.4 g (56% yield) of product was obtained after column.

Example 2

Synthesis of Compound 2

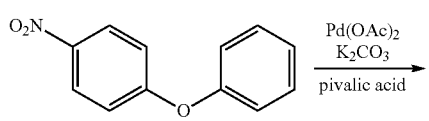

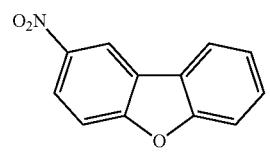

Synthesis of 2-nitrodibenzofuran

In a 1 L round-bottom flask, 1-nitro-4-phenoxybenzene (50 g, 232 mmol), potassium carbonate (3.21 g, 23.23 mmol), palladium acetate (2.61 g, 11.62 mmol), and 280 mL of pivalic acid were added. The mixture was heated to 120° C. in air. After 3 days the reaction mixture was cooled in an ice bath. 125 mL of 50% sodium hydroxide solution was added slowly in portions over time. The black emulsion was diluted with a large amount of water and ethyl acetate, filtered through Celite. The organic layer was separated, dried over magnesium sulfate, and filtered. The solvent was evaporated and pre-adsorbed onto Celite. The Celite mixture was purified by silica gel plug eluting with 10% to 50% dichloromethane in hexanes. 36.4 g (63% yield) desired product was obtained.

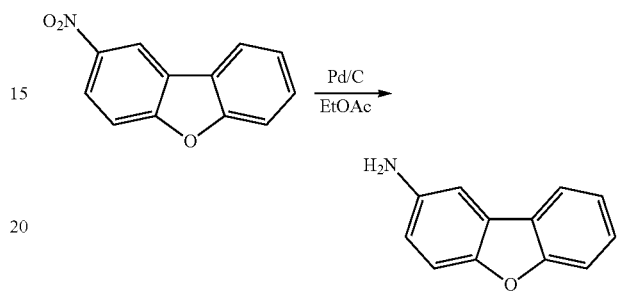

Synthesis of 2-aminodibenzofuran

In a Parr hydrogenation bottle, 10% Pd/C (0.77 g, 0.724 mmol) was added and the bottle purged with nitrogen. Next 2-nitrodibenzo[b,d]furan (15 g, 44.3 mmol) in 180 mL of ethyl acetate was added and the mixture was hydrogenated on a Parr Hydrogenator until no more hydrogen is taken up by the solution. The catalyst was filtered off through Celite and washed with ethyl acetate. The filtrate was evaporated and pre-absorbed onto Celite. The Celite mixture was purified using a Varian 400 g column eluting with dichloromethane. 10.9 g of product was obtained.

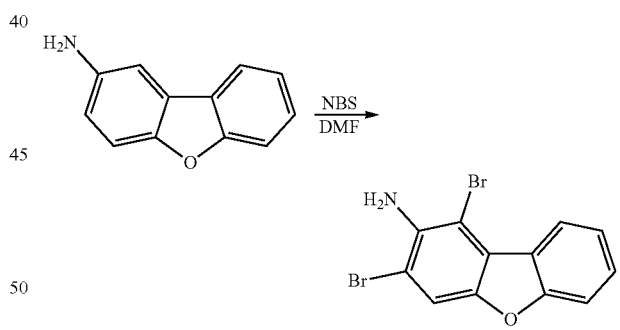

Synthesis of 2-amino-1,3-dibromobenzofuran

In a 3-neck round-bottom flask, dibenzo[b,d]furan-2-amine (20.8 g, 114 mmol) was dissolved in 160 mL of dry DMF and cooled to 0° C. A solution of N-bromosuccinimide (NBS) (44.5 g, 250 mmol) in 200 mL of DMF was added drop-wise over 1 h and the solution was stirred for 1 h. The solution was filtered through silica gel and dichloromethane was added. The organic layer was washed repeatedly with 10% LiCl solution to remove DMF. The organic layers were dried over magnesium sulfate, filtered evaporated to a purple residue. 19.24 g (50% yield) of product was obtained.

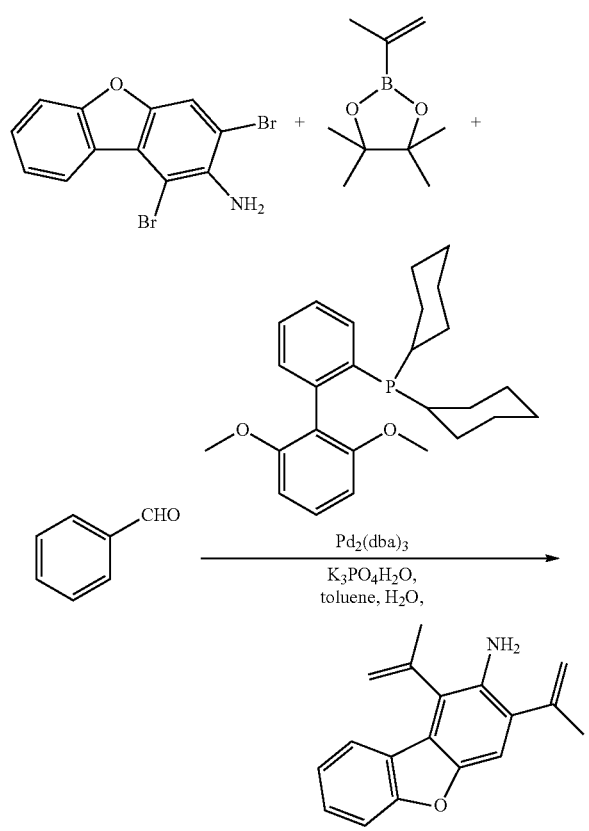

Synthesis of 1,3-di(prop-1-en-2-yl)dibenzo[b,d]furan-2-amine

In a 3-neck, 500 mL round-bottom flask, 1,3-dibromodibenzo[b,d]furan-2-amine (19.24 g, 56.4 mmol), 4,4,5,5-tetramethyl-2-(prop-1-en-2-yl)-1,3,2-dioxaborolane (30 g, 179 mmol), dicyclohexyl(2',6'-dimethoxybiphenyl-2-yl)phosphine (1.85 g, 4.51 mmol), benzaldehyde (5.7 mL, 56.4 mmol), potassium phosphate monohydrate (52 g, 226 mmol), toluene (400 mL), and water (40 mL) were mixed. Nitrogen was bubbled directly into the mixture for 15 minutes, then Pd$_2$(dba)$_3$ (1.03 g, 1.13 mmol) was added. The reaction mixture was heated to reflux overnight. After cooled to room temperature, the organic layer was separated. 40 mL of concentrated HCl was added to the organic layer. The mixture was vigorously stirred for 1 h. Aqueous sodium hydroxide solution was added to basify the mixture. The organic layer was separated and purify by silica gel plug eluting with 1:1 dichloromethane/hexanes 19.1 g of a brown oil was obtained.

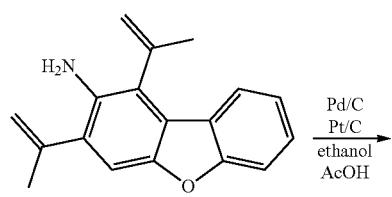

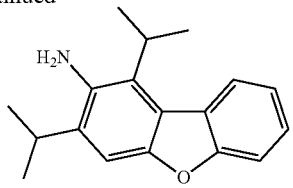

Synthesis of 1,3-diisopropyldibenzo[b,d]furan-2-amine

To a 500 mL Parr Hydrogenator bottle was added 1,2-di(prop-1-en-2-yl)dibenzo[b,d]furan-2-amine (19.1 g, 72.5 mmol), 10% palladium on carbon (5.7 g, 5.36 mmol), 5% platinum on carbon (5.7 g, 1.46 mmol), ethanol (180 mL), and acetic acid (20 mL). The mixture was hydrogenated on a Parr hydrogenator overnight. The reaction mixture was filtered through Celite and washed with dichloromethane. The filtrate was evaporated to brown oil. The oil was dissolved in dichloromethane, washed with 10% sodium hydroxide, dried over magnesium sulfate, filtered, evaporated to a brown oil. The oil was purified using a 200 g Varian column eluting with 10% ethyl acetate/hexanes. 6.55 g (34% yield) of product was obtained.

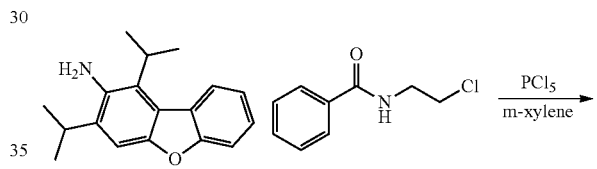

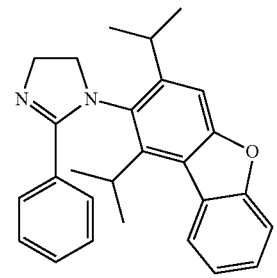

Synthesis of 1-(1,3-diisopropyldibenzo[b,d]furan-2-yl)-2-phenyl-4,5-dihydro-1H-imidazole N-(2-chloroethyl)benzamide (4.09 g, 22.27 mmol) and 90 mL m-xylene were added to a 250 ml, round-bottom flask. Next, phosphorus pentachloride (6.96 g, 33.4 mmol) was added carefully. The reaction mixture was heated to reflux under nitrogen for 2 h. The reaction mixture was cooled down to room temperature and 1,3-diisopropyldibenzo[b,d]furan-2-amine (6.55 g, 24.50 mmol) in 30 mL m-xylene was added. The reaction mixture was refluxed overnight under nitrogen. The reaction mixture was cooled in an ice bath. White solid was collected by filtration. The solid was washed with hexanes, dissolved in ethyl acetate, and washed twice with 10% sodium hydroxide solution. The organic layer was dried over magnesium sulfate, filtered, evaporated to a white solid which was dried under vacuum. 4.78 g (54% yield) of product was obtained.

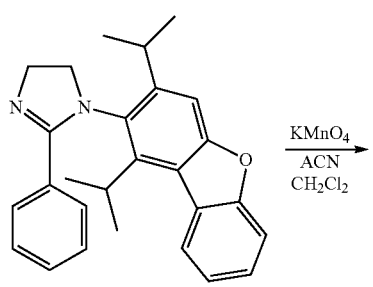

Synthesis of 1-(1,3-diisopropyldibenzo[b,d]furan-2-yl)-2-phenyl-1H-imidazole 1-(1,3-diisopropyldibenzo[b,d]furan-2-yl)-2-phenyl-4,5-dihydro-1H-imidazole (4.78 g, 12.05 mmol) in 70 mL of acetonitrile and 70 mL of dichloromethane were added to a 1 L round bottom flask. Potassium permanganate (3.81 g, 24.11 mmol) was ground in a mortar and pestle. Monmorilonite K was added and was ground together finely with the potassium permanganate. This mixture was added to the solution in portions over 0.5 hours. Reaction was done 1 h after first addition. 100 mL of methanol was added and stirred for 1 h. The solid was filtered through Celite. The material was purified using a 200 g Varian column eluting with 20% ethyl acetate/hexanes. 2.1 g (44% yield) of product was obtained after column.

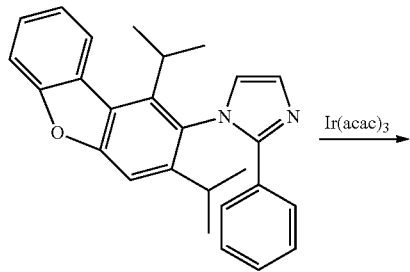

Compound 2

Synthesis of Compound 2

1-(1,3-diisopropyldibenzo[b,d]furan-2-yl)-2-phenyl-1H-imidazole (2.1 g, 5.32 mmol) and tris(acetylacetonate)iridium (III) (0.521 g, 1.065 mmol) were added to a Schlenk tube. 1 mL of tridecane was added. The reaction flask was evacuated and backfilled with nitrogen. The process was repeated 3 times. The reaction was heated up to 255 degrees under nitrogen for 70 h. After completion, the reaction mixture was diluted with dichloromethane and coated on Celite. The product was columned with 2:3 dichloromethane and hexanes. 1.0 g (68% yield) of product was obtained after column.

Example 3

Synthesis of Compound 3

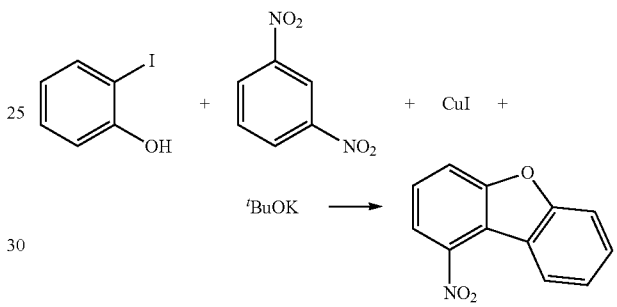

Synthesis of 1-nitrodibenzo[b,d]furan

In a flame dried 3-neck flask, CuI (10.3 g, 54.3 mmol) and 'BuOK (6.7 g, 60 mmol) were stirred in 120 mL dimethoxyethane for 1 h. To the stirred solution was added 280 mL pyridine and the solution turn purplish. In a separate flask 2-iodophenol (24.1 g, 109 mmol) and 'BuOK (12.9 g, 115 mmol) were dissolved in 60 mL dimethoxyethane and transferred to the reaction flask. Solid 2,4-dinitrodibenzofuran (16 g, 95 mmol) was then immediately added to the reaction flask and stirred for 10 minutes. Reaction mixture was then refluxed for 2.5 h. After completion, reaction mixture was cooled and carefully quenched with 8M H$_2$SO$_4$. Dark color solution was filtered thru a Celite and the filtrate was partitioned between ethylacetate and water. Aqueous layer was extracted twice with ethylacetate. Combined organic layer was washed with sodium sulfite solution followed by Na$_2$CO$_3$ solution and dried over anhydrous Na$_2$SO$_4$. Organic solvent was removed under vacuum. Crude product was purified by flash chromatography over silica gel with 20% DCM/Hexanes. Target compound (13 g, 64% yield) was isolated as yellow solid upon evaporation of organic solvent under vacuum.

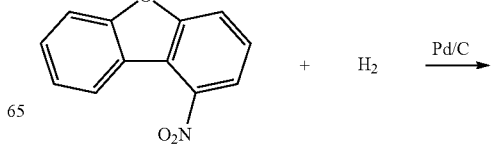

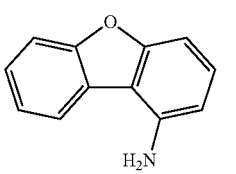

Synthesis of dibenzo[b,d]furan-1-amine 1-nitrodibenzo[b,d]furan (7.3 g, 34.2 mmol) and 730 mg 10% Pd/C were added to 150 mL ethylacetate and the reaction mixture was hydrogenated at 50 psi. Reaction mixture was then filtered out and concentrated under vacuum. Crude product was purified by flash chromatography over silica gel with 90% DCM/Hexanes. Target compound (5.1 g, 82% yield) was isolated as off white solid.

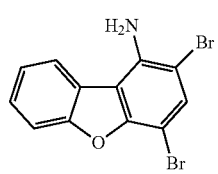

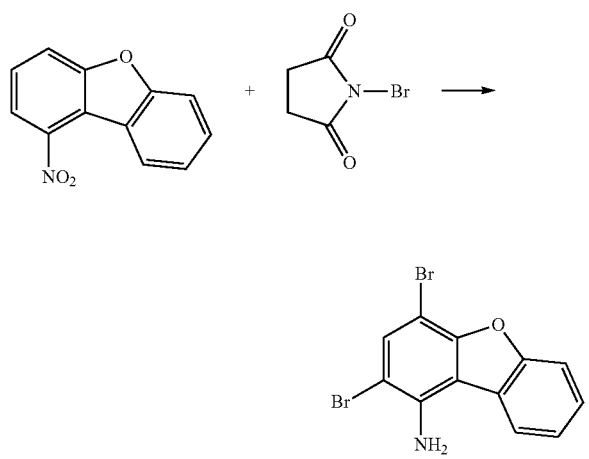

Synthesis of 2,4-dibromodibenzo[b,d]furan-1-amine

Dibenzo[b,d]furan-1-amine (5.1 g, 28 mmol) was dissolved in 120 mL DCM and cooled in an icebath. To the stirred solution, N-bromosuccinimide (10.9 g, 59 mmol) was added in small batches. After complete reaction, crude was partitioned in brine and DCM. Organic layer was washed with $Na_2CO_3$ solution followed by water and dried over anhydrous $Na_2SO_4$. Crude product was used for the next reaction.

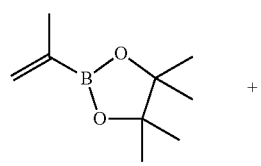

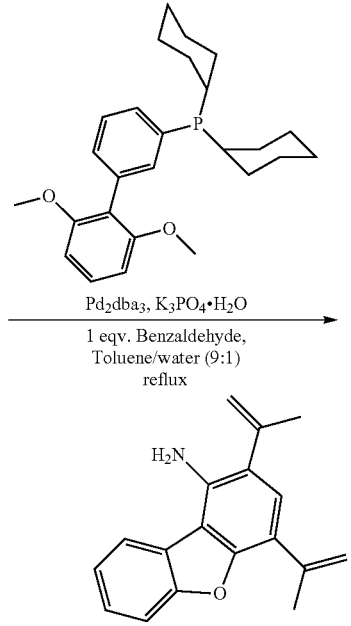

Synthesis of 2,4-di(prop-1-en-2-yl)dibenzo[b,d]furan-1-amine 2,4-dibromodibenzo[b,d]furan-1-amine (6.5 g, 18.5 mmol), isopropenylboronic acid pinacol ester (15.5 g, 92 mmol), potassium phosphate monohydrate (17 g, 74 mmol), dicyclohexyl(2',6'-dimethoxybiphenyl-3-yl)phosphine (0.6 g, 1.5 mmol), benzaldehyde (2 g, 18.5 mmol) were added to 170 mL 9:1 mixture of toluene and water. Reaction mixture was degassed via bubbling nitrogen for 30 minutes and $Pd_2dba_3$ (0.34 g, 0.4 mmol) was added at this time. Reaction mixture was degassed for another 10 minutes and then refluxed for 3 h. Crude reaction mixture was filtered through a Celite pad and partitioned between brine and ethylacetate. Ethylacetate layer was washed with 1N HCl followed by saturated $Na_2CO_3$ solution and finally dried over anhydrous $Na_2SO_4$. Crude product was purified by flash chromatography over silica gel with 40% DCM/Hexanes. Target compound (4.8 g, 99% yield) was isolated as light red color oil.

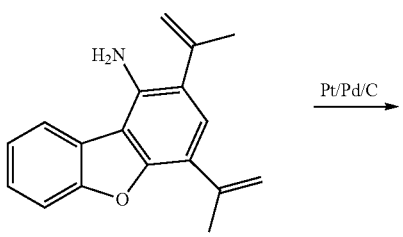

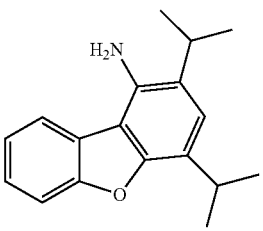

Synthesis of 2,4-diisopropyldibenzo[b,d]furan-1-amine 3,4-di(prop-1-en-2-yl)dibenzo[b,d]furan-1-amine (4.8 g, 18.2 mmol), and 5% Pt/C (0.48 g) and 10% Pd/C (0.48 g) were added to a mixture of ethanol (90 mL) and acetic acid (10 mL). Reaction mixture was hydrogenated overnight at 50 psi. Reaction mixture was filtered through a Celite pad and most of the organic solvent was evaporated under vacuum. Crude product was dissolved in ethylacetate and partitioned between 1N NaOH and ethylacetate to get rid of any acetic acid. Organic layer was dried over anhydrous $Na_2SO_4$, evaporated under vacuum and purified by flash chromatography over silica gel with 40% DCM/hexanes. Target compound (3.3 g, 68%) was isolated as white crystals.

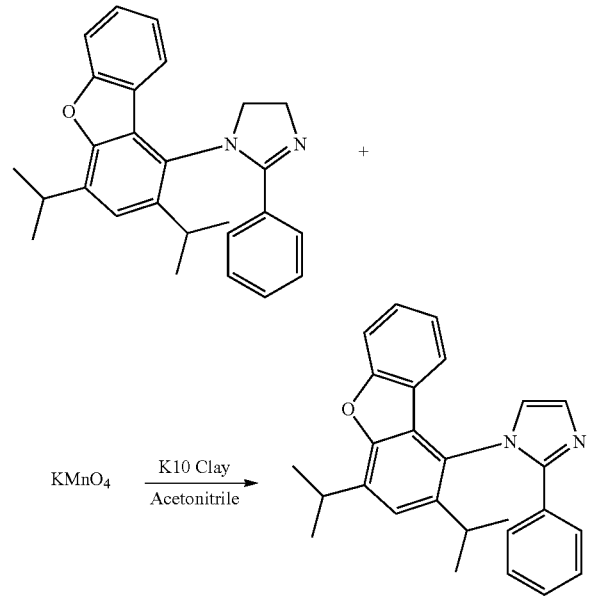

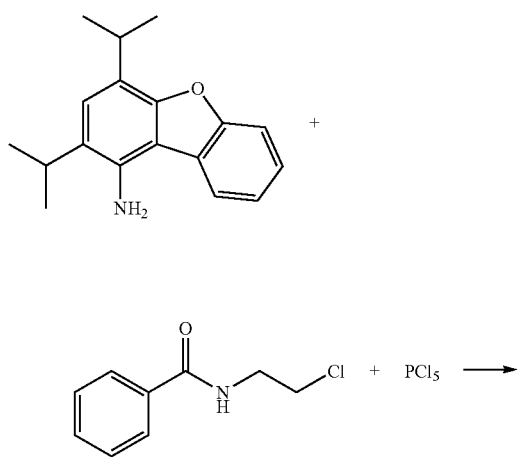

Synthesis of 1-(2,4-diisopropyldibenzo[b,d]furan-1-yl)-2-phenyl-4,5-dihydro-1H-imidazole N-(2-chloroethyl)benzamide (2.1 g, 11.2 mmol), $PCl_5$ (3.5 g, 16.8 mmol) were dissolved in m-Xylene (100 mL) and refluxed for 2 h. After cooling down the reaction flask to room temperature, 2,4-diisopropyldibenzo[b,d]furan-1-amine (3.3 g, 12.3 mmol) was added to it and the reaction mixture was refluxed overnight. From the cooled reaction mixture white precipitate was filtered out. Precipitate was dissolved in ethylacetate and partitioned between ethylacetate and aqueous $Na_2CO_3$. Organic phase was extracted out and dried under vacuum. Target compound (4 g, 90% yield) was used in next step without further purification.

Synthesis of 1-(2,4-diisopropyldibenzo[b,d]furan-1-yl)-2-phenyl-1H-imidazole 1-(2,4-diisopropyldibenzo[b,d]furan-1-yl)-2-phenyl-4,5-dihydro-1H-imidazole (4.7 g, 12 mmol) was dissolved in 100 mL acetonitrile. To the stirred solution fine mixture of $KMnO_4$ (3.8 g, 24 mmol) and 4 g montmorillonite K10 clay was added in small portions and the reaction mixture was stirred for 2 h. At the end, reaction was quenched with MeOH and filtered thru a Celite pad. Crude product was purified by flash chromatography over silica gel with 80% DCM/Hexane to 80% DCM/ethylacetate. 3 g light yellow color oil was isolated. This oil was further purified by reverse phase chromatography. Target compound (1.3 g, 28% yield) was isolated as white solid.

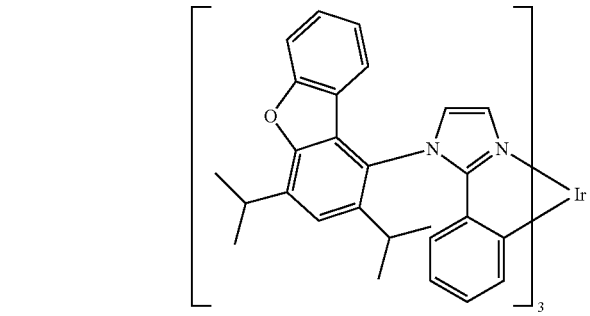

Compound 3

Synthesis of Compound 3

1-(2,4-diisopropyldibenzo[b,d]furan-1-yl)-2-phenyl-1H-imidazole (1.2 g, 3 mmol), Ir(acac)₃ and 100 μL tridecane were added in a Schlenk flask and purged with nitrogen. Reaction mixture was heated to 250° C. for 40 h. Cooled reaction mixture was chromatographed over silica gel with 1:1 DCM/hexanes. After sublimation, target compound (0.12 g, 14% yield) was obtained as yellow color crystal.

Example 4

Synthesis of Compound 4

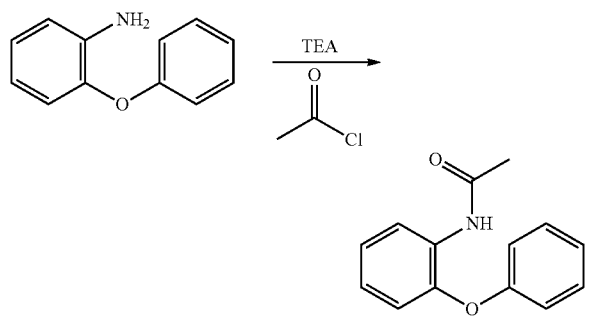

Synthesis of N-(2-phenoxyphenyl)acetamide

The mixture of 2-phenoxyaniline (100 g, 540 mmol), triethylamine (0.090 L, 648 mmol) and 1 L dichloromethane was cooled to 0° C. by ice bath. Acetyl chloride (0.04 L, 567 mmol) was added dropwise. After the addition completed, the reaction was stirred under room temperature for 2 h. The mixture was concentrated and diluted by dichloromethane. The organic phase was washed by water and dried over sodium sulfate. The crude product was purified by silica gel column (20% EtOAc in hexane) to give red brown oily solid N-(2-phenoxyphenyl)acetamide (120 g, 98% yield).

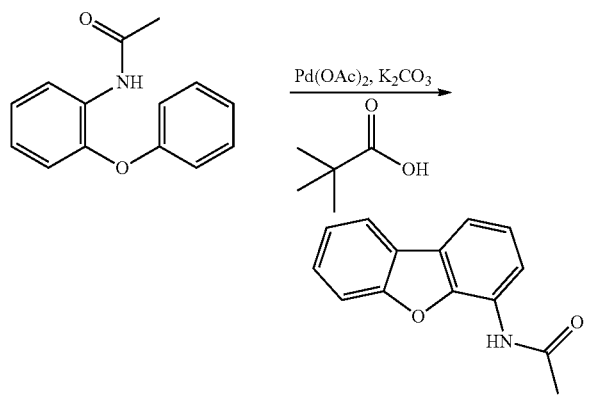

Synthesis of N-(dibenzo[b,d]furan-4-yl)acetamide

The mixture of N-(2-phenoxyphenyl)acetamide (120 g, 528 mmol), potassium carbonate (7.30 g, 52.8 mmol), palladium acetate (11.85 g, 52.8 mmol) and pivalic acid (539 g, 5280 mmol) was prepared and heated at 105° C. (inner temperature) under air for two days. GC-MS showed 60% product. The reaction was stirred at 115° C. (inner temperature) for another night. The reaction was then cooled to room temperature and neutralized by saturated sodium carbonate solution, which was then extracted by EtOAc three times. The extraction was concentrated to give the crude product N-(dibenzo[b,d]furan-4-yl)acetamide (90 g, 76% yield) as brown solid.

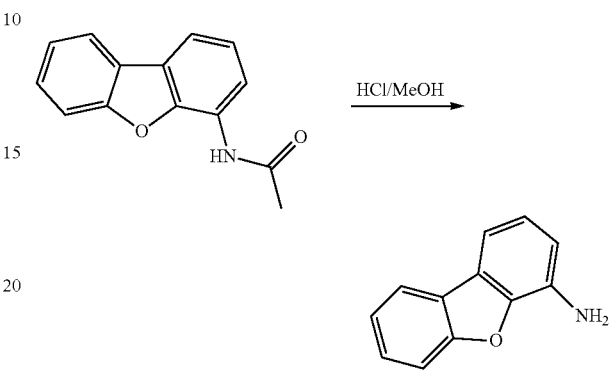

Synthesis of Dibenzo[b,d]furan-4-amine

N-(dibenzo[b,d]furan-4-yl)acetamide (90 g, 400 mmol) was suspended in the mixture of concentrated HCl (240 mL) and methanol (240 mL). The reaction was refluxed for 2 h and then cooled to room temperature. Saturated sodium carbonate was used to neutralize the solution. The residue was collected by filtration and redissolved in DCM. After dried over sodium sulfate, the solution was concentrated to give dibenzo[b,d]furan-4-amine (67 g, 92% yield) as brown solid.

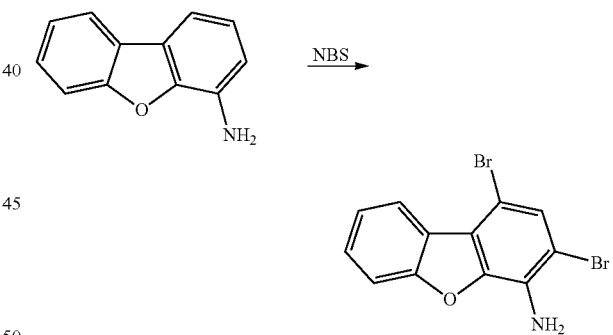

Synthesis of 1,3-Dibromodibenzo[b,d]furan-4-amine

Dibenzo[b,d]furan-4-amine (33.4 g, 182 mmol) was dissolved in DMF (300 mL) and cooled to 0° C. by ice bath. 1-bromopyrrolidine-2,5-dione (68.1 g, 383 mmol) was dissolved in DMF (300 mL) and added into the reaction solution dropwise. After the addition, the reaction was stirred at room temperature overnight. Then the reaction mixture was diluted by EtOAc and washed by 10% LiCl solution three times and saturated sodium bicarbonate twice. The organic layer was dried over sodium sulfate and concentrated. The crude product was purified with silica gel column (<15% EtOAc in hexane) to give red brown solid 1,3-dibromodibenzo[b,d]furan-4-amine (76 g, 122% yield, containing some succinimide).

Synthesis of N-(1,3-dibromodibenzo[b,d]furan-4-yl)acetamide

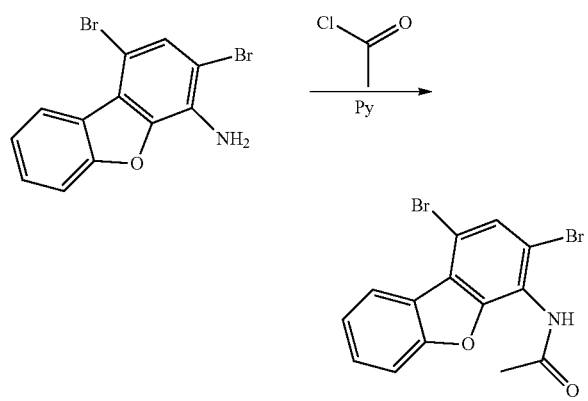

In a 2 L round-bottomed flask, 1,3-dibromodibenzo[b,d]furan-4-amine (76 g, 223 mmol) in dichloromethane (800 mL) and pyridine (180 mL, 2229 mmol) were cooled by ice bath. Acetyl chloride (31.7 mL, 446 mmol) was added dropwise while stirring. Then the ice bath was removed. The reaction was stirred at room temperature for 1 h. The residue was collected by filtration and washed by water and dichloromethane to give N-(1,3-dibromodibenzo[b,d]furan-4-yl)acetamide (60 g, 70.3% yield) as brown solid.

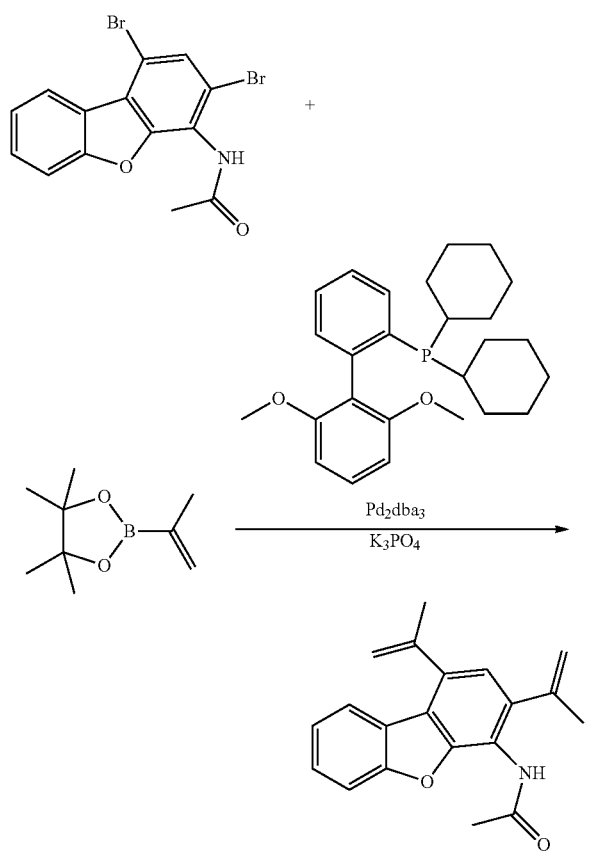

Synthesis of N-(1,3-di(prop-1-en-2-yl)dibenzo[b,d]furan-4-yl)acetamide

N-(1,3-dibromodibenzo[b,d]furan-4-yl)acetamide (55 g, 144 mmol), 4,4,5,5-tetramethyl-2-(prop-1-en-2-yl)-1,3,2-dioxaborolane (72.4 g, 431 mmol) and potassium phosphate tribasic (132 g, 574 mmol) were mixed into toluene (800 mL) and water (80 mL). The mixture was bubbled with nitrogen for 20 minutes. Then $Pd_2(dba)_3$ (2.63 g, 2.87 mmol) and dicyclohexyl(2',6'-dimethoxybiphenyl-2-yl)phosphine (4.72 g, 11.49 mmol) were added into the reaction mixture. After bubbled by nitrogen for another 20 minutes, the reaction was refluxed overnight under nitrogen. After cooled to room temperature, the organic layer was washed by water, dried over sodium sulfate and concentrated. After silica gel column (30%-50% EtOAc in hexane) got N-(1,3-di(prop-1-en-2-yl)dibenzo[b,d]furan-4-yl)acetamide (32.5 g, 74.1% yield) as brown solid.

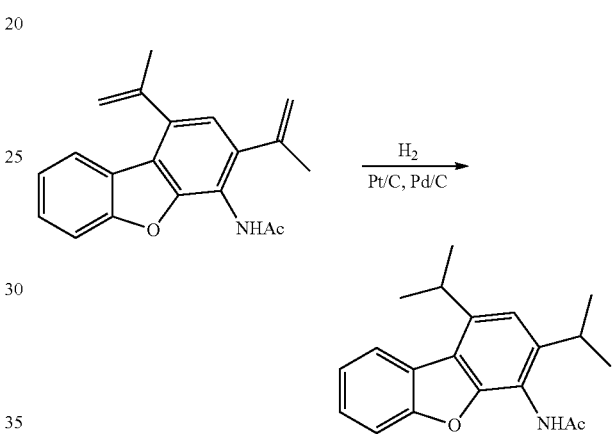

Synthesis of N-(1,3-diisopropyldibenzo[b,d]furan-4-yl)acetamide

In a 500 mL hydrogenation container was added N-(1,3-di(prop-1-en-2-yl)dibenzo[b,d]furan-4-yl)acetamide (22.6 g, 74.0 mmol), Pd/C, 10% (3 g, 74.0 mmol) and Pt/C, 5% (3 g, 74.0 mmol) in Ethanol (200 mL). After two days reaction, the solution was filtered through a Celite plug and washed with dichloromethane. The filtration was concentrated to give crude N-(1,3-diisopropyldibenzo[b,d]furan-4-yl)acetamide (18.8 g, 82% yield) as white solid.

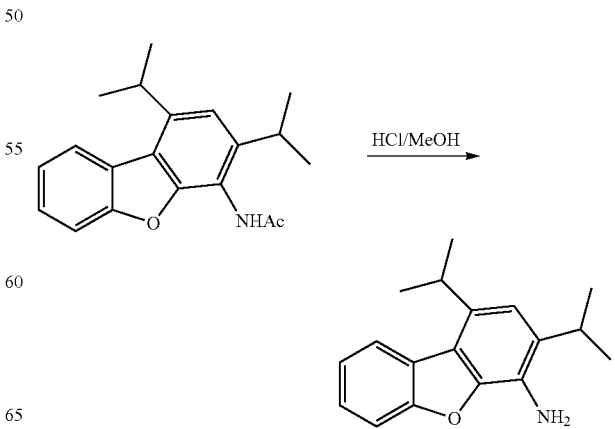

Synthesis of 1,3-Diisopropyldibenzo[b,d]furan-4-amine

N-(1,3-diisopropyldibenzo[b,d]furan-4-yl)acetamide (15 g, 48 mmol) was suspended in the mixture of Concentrated HCl (125 mL) and MeOH (125 mL). The mixture was refluxed for 2 h and then cooled to room temperature. Saturated sodium carbonate was used to neutralize the solution. The residue was collected by filtration and redissolved in DCM. After dried over sodium sulfate, the solution was concentrated to give 1,3-diisopropyldibenzo[b,d]furan-4-amine (10.5 g, 81% yield) as brown solid.

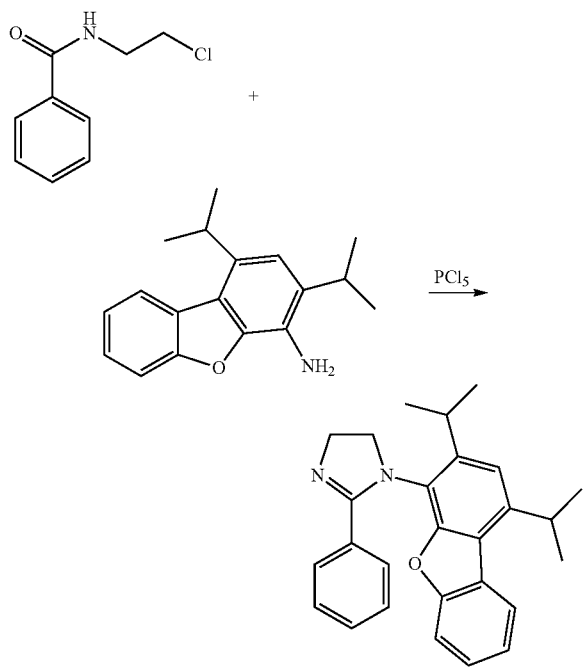

Synthesis of 1-(1,3-Diisopropyldibenzo[b,d]furan-4-yl)-2-phenyl-4,5-dihydro-1H-imidazole N-(2-chloroethyl)benzamide (6.3 g, 34 mmol) and PCl$_5$ (7.9 g, 38 mmol) were suspended in xylene (75 mL) and refluxed for two hours. Then 1,3-diisopropyldibenzo[b,d]furan-4-amine (10 g, 38 mmol) was added. The mixture was refluxed overnight. After cooling by ice-bath, no precipitation was observed. The mixture was concentrated and the residue was washed with small amount of toluene and hexane. The crude 1-(1,3-diisopropyldibenzo[b,d]furan-4-yl)-2-phenyl-4,5-dihydro-1H-imidazole (7.5 g, 19 mmol, 54.8% yield) was used without further purification for the next step.

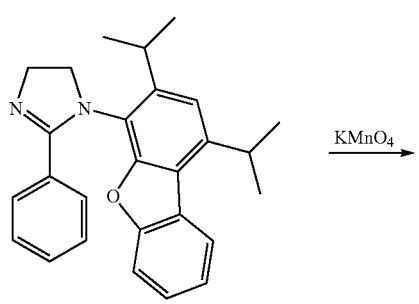

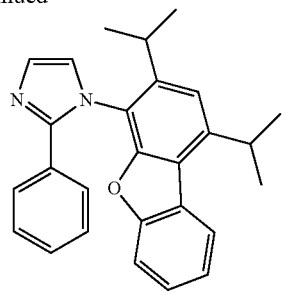

Synthesis of 1-(1,3-Diisopropyldibenzo[b,d]furan-4-yl)-2-phenyl-1H-imidazole

The potassium permanganate (5.58 g, 35.3 mmol) and Montmorillonite K-10 clay (10 g) were mixed and finely grounded. The mixture was slowly (about 15 minutes) added into the mixed solution of dichloromethane (50 mL), acetonitrile (150 mL) and 1-(1,3-diisopropyldibenzo[b,d]furan-4-yl)-2-phenyl-4,5-dihydro-1H-imidazole (7 g, 17.6 mmol), which was cooled by ice bath. Then the reaction was stirred for another hour and quenched by adding 20 mL of ethanol. Filtered through a Celite plug. The crude product was purified by silica gel column (up to 30% EtOAc in hexanes) and recrystallization from hexane. 1-(1,3-diisopropyldibenzo[b,d]furan-4-yl)-2-phenyl-1H-imidazole (2.6 g, 6.57 mmol, 37.2% yield) was obtained as white solid (99.8% HPLC).

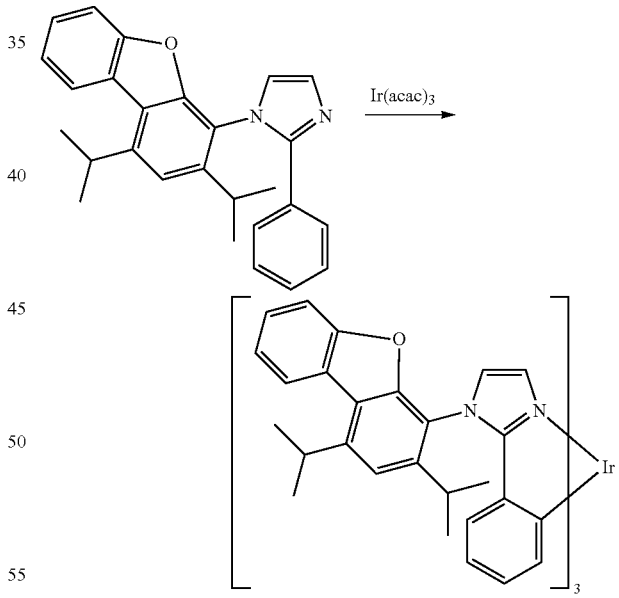

Compound 4

Synthesis of Compound 4

Ir(acac)$_3$ (0.620 g, 1.267 mmol), 1-(1,3-diisopropyldibenzo[b,d]furan-4-yl)-2-phenyl-1H-imidazole (2.5 g, 6.34 mmol) and tridecane (1 mL) were mixed in a Schlenk tube. After carefully vacuumed and refilled with nitrogen four times, the reaction was heated in 250° C. sand bath for three days. The crude product was purified by silica column with up to 80% dichloromethane in hexane to give product (700 mg, 40.2% yield) as yellow solid.

Example 5

Synthesis of Compound 5

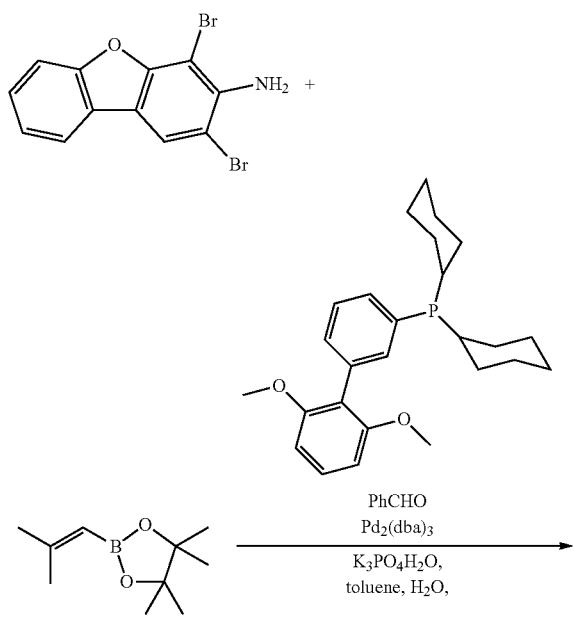

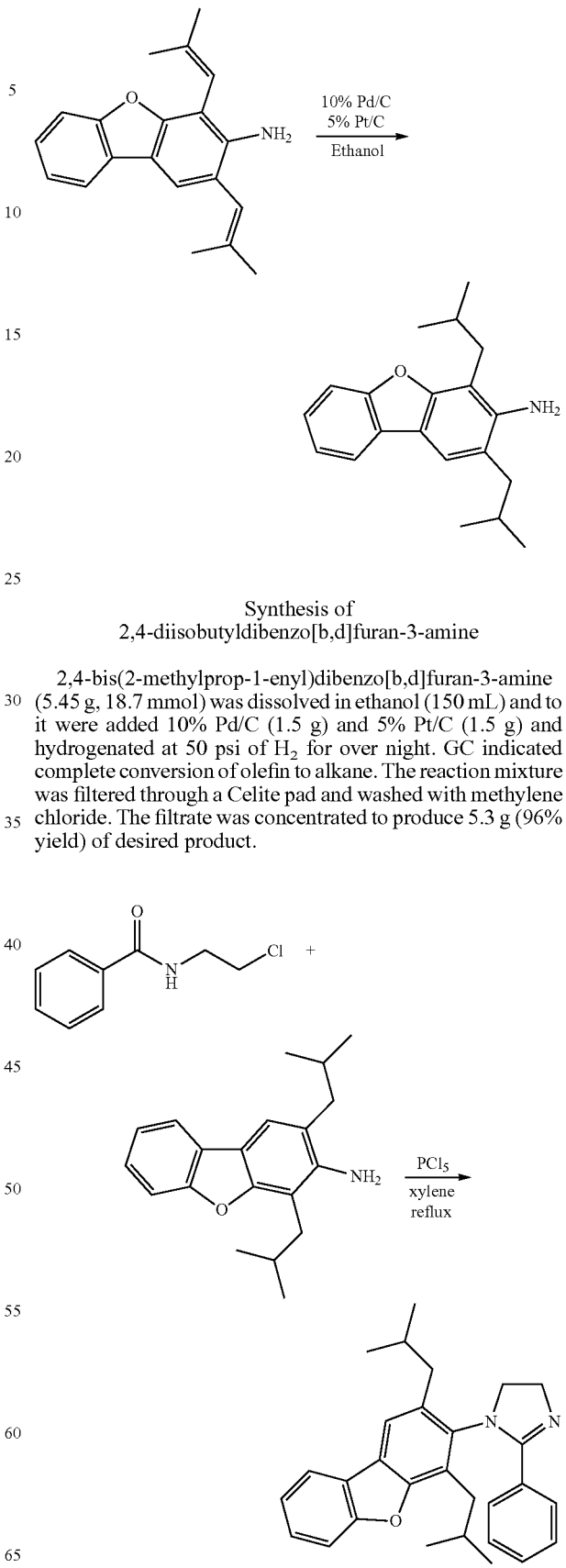

Synthesis of 2,4-bis(2-methylprop-1-enyl)dibenzo[b,d]furan-3-amine

To a degassed toluene (40 mL), 2,4-dibromodibenzofuran-3-amine (1.5 g, 4.4 mmol), benzaldehyde (0.47 g, 4.4 mmol) 4,4,5,5-tetramethyl-2-(2-methylprop-1-enyl)-1,3,2-dioxaborolane (3.2 g, 17.6 mmol), potassium phosphate (6.08 g, 26 mmol), 2-dicyclohexylphosphino-2',6'-dimethoxybiphenyl (0.28 g, 0.704 mmol), Pd$_2$(bda)$_3$ (0.161 g, 0176 mmol) and water (6 mL) were sequentially added. The solution was refluxed for overnight in an atmosphere of nitrogen and then allowed to cool to room temperature. The reaction was diluted with ethyl acetate and the organic phase was separated from the aqueous phase. The organic phase was dried over sodium sulfate and the solvent was removed under vacuum. The product was chromatographed using silica gel with ethylacetate and hexanes as the eluent. The solvent was removed to give 1.05 g (82% yield) of title compound.

Synthesis of 2,4-diisobutyldibenzo[b,d]furan-3-amine 2,4-bis(2-methylprop-1-enyl)dibenzo[b,d]furan-3-amine (5.45 g, 18.7 mmol) was dissolved in ethanol (150 mL) and to it were added 10% Pd/C (1.5 g) and 5% Pt/C (1.5 g) and hydrogenated at 50 psi of H$_2$ for over night. GC indicated complete conversion of olefin to alkane. The reaction mixture was filtered through a Celite pad and washed with methylene chloride. The filtrate was concentrated to produce 5.3 g (96% yield) of desired product.

Synthesis of 1-(2,4-diisobutyldibenzo[b,d]furan-3-yl)-2-phenyl-4,5-dihydro-1H-imidazole N-(2-chloroethyl)benzamide (3.1 g, 16.88 mmol) was dissolved in 40 mL anhydrous m-xylene under nitrogen. Phosphorus pentachloride (5.27 g, 25.3 mmol) was then carefully added and the mixture heated to reflux under nitrogen for 2 h. The solution was allowed to cooled to room temperature and 2,4-diisobutyldibenzo[b,d]furan-3-amine (5.49 g, 18.57 mmol) was added. The reaction mixture was heated to reflux for 20 h. After cooling, the precipitate was filtered and the solid imidazoline product was collected and washed with toluene followed by hexanes. The resultant crude product was dissolved in methylene chloride and washed twice with 50% NaOH. The organic layer was dried over $MgSO_4$, filtered and concentrated under reduced pressure to afford title product (5.5 g, 77%).

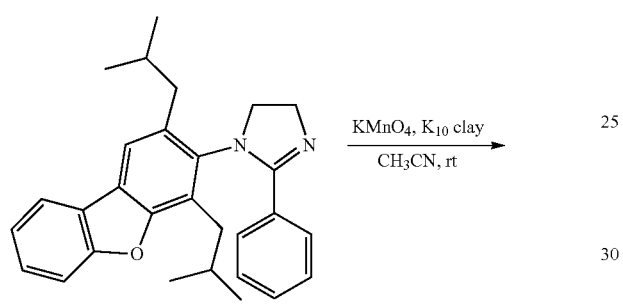

Synthesis of 1-(2,4-diisobutyldibenzo[b,d]furan-3-yl)-2-phenyl-1H-imidazole

Potassium permanganate (4.09 g 25.9 mmol) and K-10 (8.1 g) were ground together in a mortar until a fine homogeneous powder was obtained. This $KMnO_4$—K-10 powder was added portion-wise to a solution of 1-(2,4-diisobutyldibenzo[b,d]furan-3-yl)-2-phenyl-4,5-dihydro-1H-imidazole (5.5 g, 12.9 mmol) in $CH_3CN$ (100 mL) and the mixture stirred at room temperature for 2 h. Ethanol (5 mL) was added to reduce excess oxidant. After stirring for an additional 30 minutes, the mixture was filtered through a short pad of Celite and the solid washed with $CH_3CN$ (50 mL). The filtrate was evaporated and the resulting crude material was purified by chromatography on $SiO_2$ to obtain desired imidazole (2.76 g, 50%).

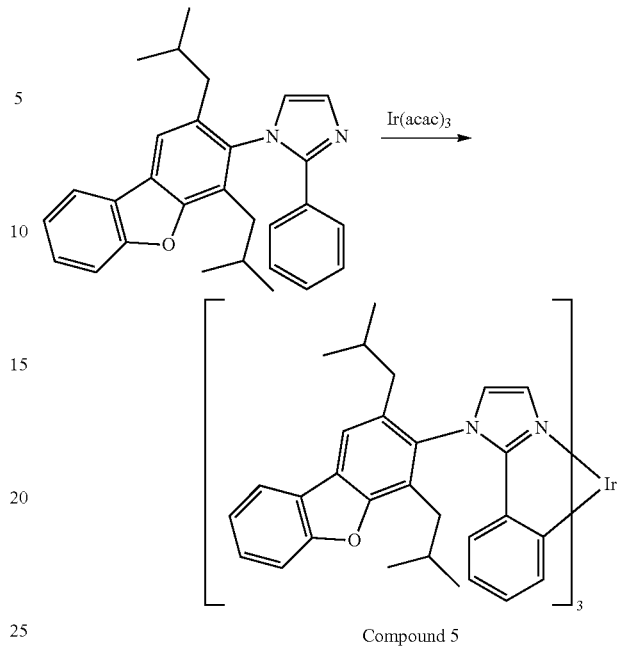

Compound 5

Synthesis of Compound 5

(1-(2,4-diisobutyldibenzo[b,d]furan-3-yl)-2-phenyl-1H-imidazole 1.97 g, 4.67 mmol), tridecane (0.1 mL), and Ir(acac)₃ (0.44 g, 0.899 mmol) were added to a Schlenk tube. The tube was evacuated and refilled with nitrogen. The process was repeated three times. The reaction was heated up to 250° C. for 40 h. After cooled to room temperature, the reaction was diluted with dichloromethane and purified by silica gel column chromatography using 1:1 hexanes and dichloromethane as eluent. 0.7 g (54% yield) of product was obtained.

Example 6

Synthesis of Compound 13

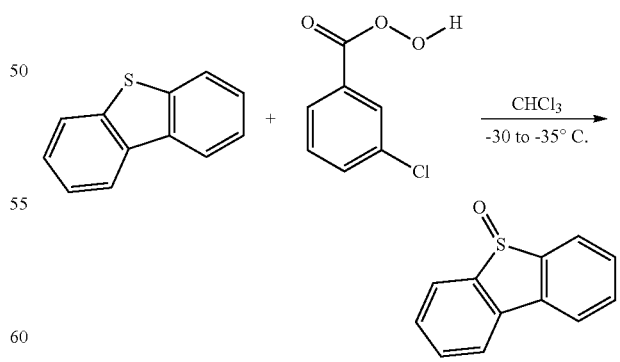

Synthesis of Dibenzothiophene-9-oxide

A solution of 3-chlorobenzoperoxoic acid (22.38 g, 100 mmol) (mcpba) in 200 mL of chloroform was dropwise added to dibenzo[b,d]thiophene (18.4 g, 100 mmol) in 200 mL of chloroform at −30° C. to −35° C. After stirring at −30° C. for 1 h, the reaction mixture was allowed to come to room temperature and stirred for 1 h at room temperature. The mixture was filtered thru a Celite pad and the residue was neutralized using aqueous $Na_2CO_3$. The organic layer from the reaction mixture was dried over $Na_2SO_4$, concentrated under reduced vacuum and performed silica gel column using 1:1 DCM/hexanes as eluents. The solid product was further re-crystallized from ethanol to afford the white dibenzothiophene-9-oxide (14.6 g, 73%).

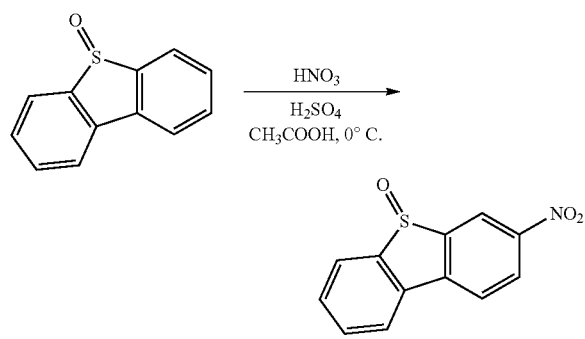

Synthesis of 3-Nitrodibenzothiophene-9-oxide

Dibenzothiophene-9-oxide (15 g, 74.9 mmol), was dissolved in 33 mL of acetic acid and 33 mL of sulfuric acid and cooled in ice bath to 0 C. 36 mL of Fuming nitric acid is added drop wise during a period of 15 minutes. The reaction mixture was stirred vigorously for 30 minutes at 0° C. Then ice cold water was added and yellow precipitate formed which was filtered and washed with plenty of water. The precipitate was dissolved in methylene chloride, dried over $Na_2SO_4$ and concentrated under reduced pressure. Finally, yellow solid was re-crystallized from ethanol to afford 3-nitrodibenzothiophene-9-oxide (11 g, 60%).

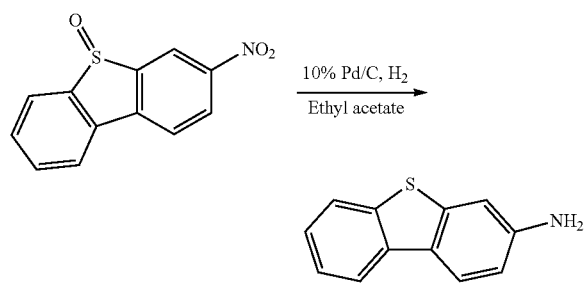

Synthesis of 3-Aminodibenzothiophene 3-nitrodibenzothiophene-9-oxide (11 g, 44.9 mmol) was slurred in 200 mL ethyl acetate and 5 g of 10% Pd/C was added to the flask. Reaction mixture was hydrogenated for 45 minutes at 50 psi $H_2$ pressure. Reaction mixture was filtered through a small Celite pad. Filtrate was concentrated under reduced pressure and performed silica gel column using DCM/Hexanes as eluents to produce desired compound (6.8 g, 76%).

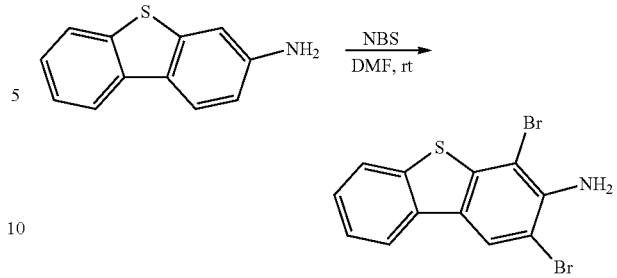

Synthesis of 2,4-Dibromo-3-aminodibenzothiophene

3-Aminodibenzothiophene (6.8 g, 34.1 mmol) was dissolved in dry DMF (25 mL) and cooled to 0° C. A solution of N-bromosuccinamide (NBS) in DMF (30 mL) was slowly cannulated to the reaction flask. The reaction mixture was stirred at 0° C. for 1 h, then water was added to the reaction mixture and precipitate was formed which was filtered and washed with water several times. The precipitate was dissolved in methylene chloride dried over sodium sulfate, concentrated under reduced pressure. The crude product was purified by short silica column using hexanes and ethyl acetate as eluents to give the title compound (12 g, 94%).

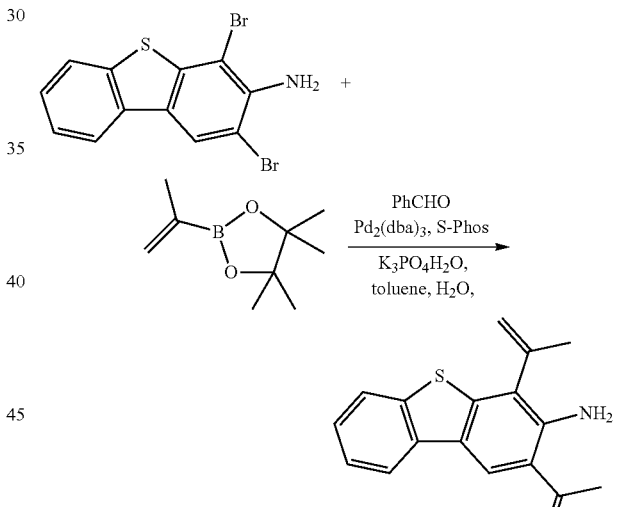

Synthesis of 2,4-di(prop-1-en-2-yl)dibenzo[b,d]thiophen-3-amine

To a degassed toluene (200 mL), 2,4-dibromodibenzo[b,d]thiophen-3-amine (12.15 g, 34.0 mmol), 4,4,5,5-tetramethyl-2-(prop-1-en-2-yl)-1,3,2-dioxaborolane (17.15 g, 102 mmol), benzaldehyde (3.61 g, 34.0 mmol), potassium phosphate (23.51 g, 102 mmol) dicyclohexyl(2',6'-dimethoxy-[1,1'-biphenyl]-2-yl)phosphine (1.676 g, 4.08 mmol) and $Pd_2(dba)_3$ (0.935 g, 1.021 mmol) and water (20 mL) were sequentially added. The solution was refluxed for overnight in an atmosphere of nitrogen and then allowed to cool to room temperature. The reaction was diluted with ethyl acetate and the organic phase was separated from the aqueous phase. The organic phase was dried over sodium sulfate and the solvent was removed under vacuum. The product was chromatographed using silica gel with ethylacetate and hexanes as the eluent. The solvent was removed to give the title compound (9.0, 95%).

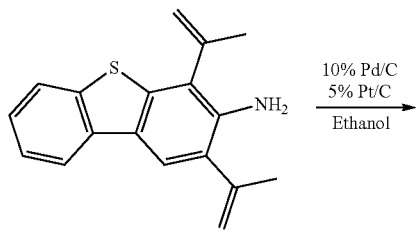

Synthesis of 2,4-diisopropyldibenzo[b,d]thiophen-3-amine 2,4-di(prop-1-en-2-yl)dibenzo[b,d]thiophen-3-amine (9 g, 32.2 mmol) was dissolved in ethanol (150 mL) and 9 mL of acetic acid was added. To the flask, 10% Pd/C (9.0 g) and 5% Pt/C (9.0 g) were added and hydrogenated at 40 psi of $H_2$ for over night. GC indicated complete conversion of olefin to alkane. The reaction mixture was filtered through a Celite pad and washed with methylene chloride. The filtrate was concentrated to produce 7.5 g (82%) of desired product.

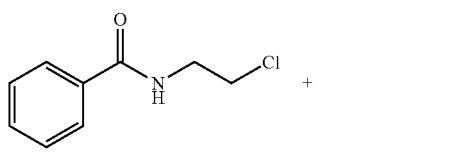

Synthesis of 1-(2,4-diisopropyldibenzo[b,d]thiophen-3-yl)-2-phenyl-4,5-dihydro-1H-imidazole N-(2-chloroethyl)benzamide (4.3 g, 23.42 mmol), was dissolved in 50 mL anhydrous m-xylene under nitrogen. Phosphorus pentachloride (7.31 g, 35.1 mmol) was then carefully added and the mixture heated to reflux under nitrogen for 2 h. The solution was allowed to cooled to room temperature and 2,4-diisopropyldibenzo[b,d]thiophen-3-amine (7.30 g, 25.8 mmol) was added. The reaction mixture was heated to reflux for 20 h. After cooling, the precipitate was filtered and the solid imidazoline product was collected and washed with toluene followed by hexanes. The resultant crude product was dissolved in methylene chloride and washed twice with 50% NaOH. The organic layer was dried over $MgSO_4$, filtered and concentrated under reduced pressure to afford title product (4.8 g, 50%).

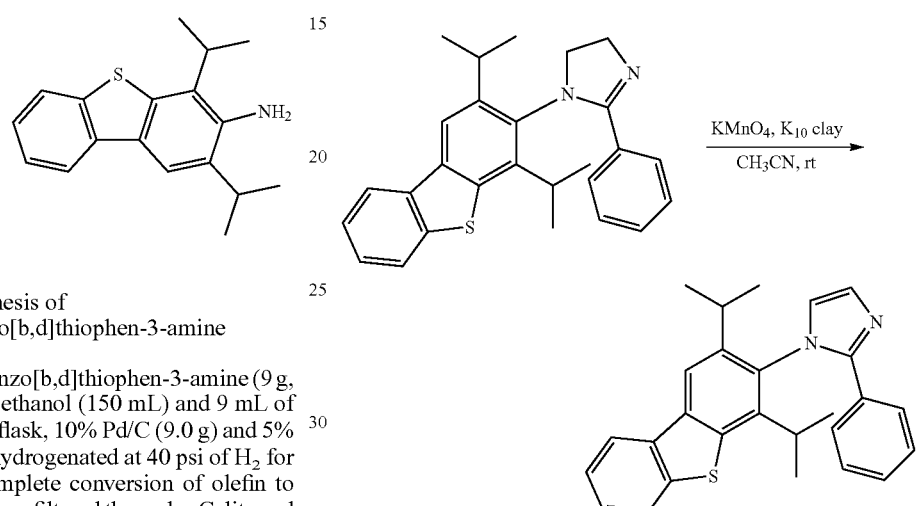

Synthesis of 1-(2,4-diisopropyldibenzo[b,d]thiophen-3-yl)-2-phenyl-1H-imidazole Potassium permanganate (3.6 g, 23.27 mmol) and K-10 mononitrile (7.2 g) were ground together in a mortar until a fine homogeneous powder was obtained. This $KMnO_4$—K-10 powder was added portion-wise to a solution of 1-(2,4-diisopropyldibenzo[b,d]thiophen-3-yl)-2-phenyl-4,5-dihydro-1H-imidazole (4.8 g, 11.63 mmol) in $CH_3CN$ (40 mL) and the mixture stirred at room temperature for 2 h. 5 mL ethanol was added to reduce excess oxidant. After stirring for an additional 30 minutes, the mixture was filtered through a short pad of Celite and the solid washed with methylene chloride (50 mL). The filtrate was evaporated and the resulting crude material was purified by chromatography on $SiO_2$ to obtain desired imidazole (1.2 g, 25%).

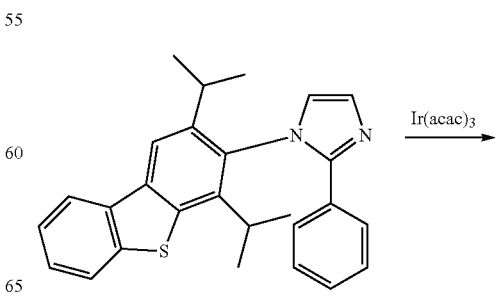

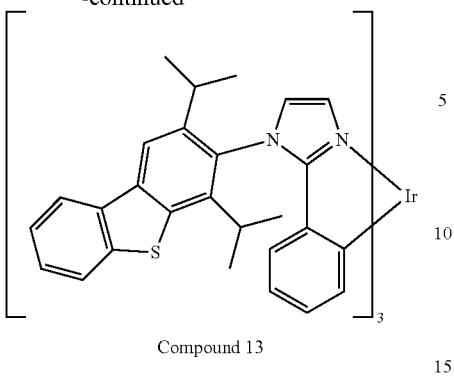

Compound 13

Synthesis of Compound 13

1-(2,4-diisopropyldibenzo[b,d]thiophen-3-yl)-2-phenyl-1H-imidazole (0.783 g, 1.907 mmol) and Tris(acetylacetonate)iridium (III) (0.187 g, 0.381 mmol) were added to a Schlenk tube. 0.2 mL of tridecane was added. The reaction flask was evacuated and backfilled with nitrogen. The process was repeated for 3 times. The reaction was heated up to 255 degrees under nitrogen for 70 h. After completion, the reaction mixture was diluted with dichloromethane and coated on Ceilte. The product was purified by column using 2:3 dichloromethane and hexanes as solvent. 0.3 g (55.4% yield) of product was obtained after purification.

Device Examples

All device examples were fabricated by high vacuum (<10$^{-7}$ Torr) thermal evaporation. The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

The organic stack of the Devices consisted of sequentially, from the ITO surface, 100 Å of E2 as the hole injection layer (HIL), 300 Å of 4,4'-bis[N-(1-naphthyl)-N-phenylamino]biphenyl (α-NPD) as the hole transporting later (HTL), 300 Å of H1 doped with 15% or 9% of the emissive dopant, e.g., Compounds 1 and 13, as the emissive layer (EML), 50 Å of H1 as the blocking layer (BL), and 400 Å of Alq$_3$ (tris-8-hydroxyquinoline aluminum) as the electron transporting layer (ETL).

Comparative Device Example 1 was fabricated similarly to Device Examples 1-3, except E1 was used the emitting dopant.

As used herein, the following compounds have the following structures:

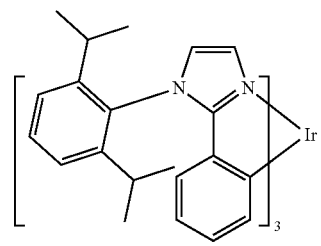

E1

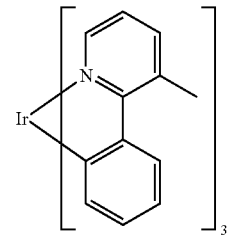

E2

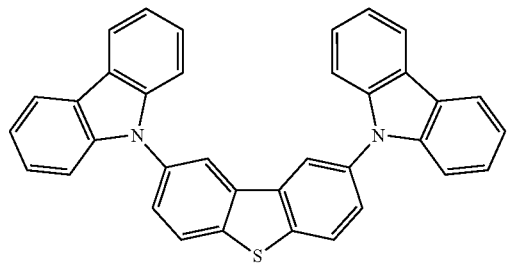 [SMILES: c1ccc2c(c1)c1ccccc1n2-c1ccc2sc3ccc(-n4c5ccccc5c5ccccc54)cc3c2c1]

H1

Particular emissive dopants for the emissive layer of an OLED are provided. These compound may lead to devices having particularly good properties. The device structures are provided in Table 2, and the corresponding device data are provided in Table 3. Cmpd. is an abbreviation for Compound. Ex. is an abbreviation for Example. Comp. is an abbreviation for Comparative.

TABLE 2

| Example | HIL | HTL | EML (300 Å, doping %) | | BL | ETL |
|---|---|---|---|---|---|---|
| Ex. 1 | E2 100 Å | NPD 300 Å | H1 | Cmpd. 1 9% | H1 50 Å | Alq 400 Å |
| Ex. 2 | E2 100 Å | NPD 300 Å | H1 | Cmpd. 1 15% | H1 50 Å | Alq 400 Å |
| Ex. 3 | E2 100 Å | NPD 300 Å | H1 | Cmpd. 13 15% | H1 50 Å | Alq 400 Å |
| Comp. Ex. 1 | E2 100 Å | NPD 300 Å | H1 | E1 15% | H1 50 Å | Alq 400 Å |

TABLE 3

| | 1931 CIE | | | FWHM | Voltage | At 1000 cd/m$^2$ | | | At 2000 cd/m$^2$ |
|---|---|---|---|---|---|---|---|---|---|
| | | | | | | LE | EQE | PE | LT$_{80\%}$ |
| Ex. | x | y | λ$_{max}$ | (nm) | (V) | (Cd/A) | (%) | (lm/W) | (h) |
| Ex. 1 | 0.182 | 0.377 | 474 | 54 | 8.1 | 27 | 12.1 | 10.5 | 210 |
| Ex. 2 | 0.183 | 0.381 | 474 | 52 | 7.1 | 31.2 | 14 | 13.8 | 320 |
| Ex. 3 | 0.180 | 0.397 | 474 | 56 | 7.8 | 31.9 | 13.9 | 12.9 | 264 |
| Comp. Ex. 1 | 0.175 | 0.384 | 474 | 56 | 5.9 | 40.2 | 18.4 | 21.3 | 155 |

From Device Examples 1-3, it can be seen that the invention compounds as emitting dopants in blue phosphorescent OLEDs give long device lifetime. In particular, the lifetime, $LT_{80\%}$ (defined as the time required for the initial luminescence, $L_0$, to decay 80% of its value, at a constant current density from an initial brightness of 2000 cd/m² at room temperature) of the invention compounds are much higher compared to E1. Specifically, Compounds 1 and 13 have a lifetime of 320 h and 264 h, respectively, compared to 155 h for E1.

The transient lifetimes of Compounds 1, 2, 3, 4, 13 and A are shown in Table 4. It was found that compounds with dibenzofuran (i.e., X is O) and dibenzothiophene (i.e., X is S) substitution have shorter transient lifetimes. In particular, the 77K PL transient lifetimes of Compounds 1-4 and 13 were less than lifetimes measured for previously reported compounds. Specifically, Compounds 1-4 and 13 had a lifetime of <2.6 μs compared to E1, which had a lifetime of 3.2 μs (see Table 4). The reduced transient lifetime may be an important photophysical property of the compounds, because compounds with shorter excited state lifetimes have higher radiative rates. Without being bound by theory, it is believed that these compounds may be more stable in the device because the molecule spends less time in the excited state. Thus, there is a reduced likelihood that photochemical reactions or quenching may occur. Therefore, these compounds may provide devices with improved lifetime.

TABLE 4

| Cmpd. | 77K LT (μs) |
|---|---|
| Cmpd. 1 | 2.34 |
| Cmpd. 2 | 2.52 |
| Cmpd. 3 | 2.56 |
| Cmpd. 4 | 2.55 |
| Cmpd. 13 | 2.27 |
| E1 | 3.2 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound comprising a ligand L having the formula:

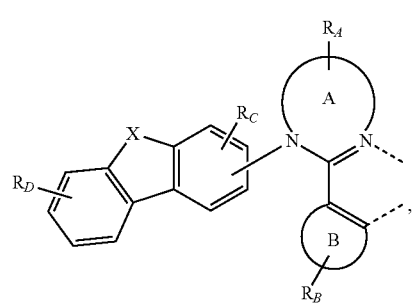

Formula I wherein A is a 5-membered heterocyclic ring;
wherein B is a 6-membered carbocyclic ring;
wherein $R_B$ and $R_D$ represent mono, di, tri, or tetra substitutions;
wherein $R_A$ represents mono or di substitution;
wherein $R_A$, $R_B$, and $R_D$ are independently selected from hydrogen, halogen, alkyl, alkoxy, amino, alkenyl, alkynyl, aryl and heteroaryl;
wherein $R_A$, $R_B$, and $R_D$ are optionally fused;
wherein X is selected from the group consisting of NR, O, and S;
wherein R is aryl or alkyl;
wherein $R_C$ represents two identical substituents with the two substituents having a meta relationship to each other;
wherein at least one $R_C$ is ortho to a carbon bonded to ring A;
wherein the $R_C$ substituents are selected from cyclic alkyl and branched alkyl;
wherein each $R_C$ has 3 or more carbon atoms; and
wherein the ligand L is coordinated to a metal M having an atomic number greater than 40.

2. The compound of claim 1, wherein the compound is heteroleptic and all of the ligands L in the compound have Formula I.

3. The compound of claim 1, wherein the compound is heteroleptic and at least one ligand L in the compound has Formula I.

4. The compound of claim 1, wherein B is phenyl.

5. The compound of claim 1, wherein M is Ir.

6. The compound of claim 1, wherein the ring containing $R_C$ has two substituents located at the positions ortho to the carbon atom connected to A.

7. The compound of claim 1, wherein the ring containing $R_C$ has one alkyl substituent having 3 or more carbon atoms that is located at a position ortho to the carbon atom attached to A and the other position ortho to the carbon atom attached to A is occupied by X or the phenyl ring containing $R_D$.

8. The compound of claim 1, wherein the compound is selected from the group consisting of:

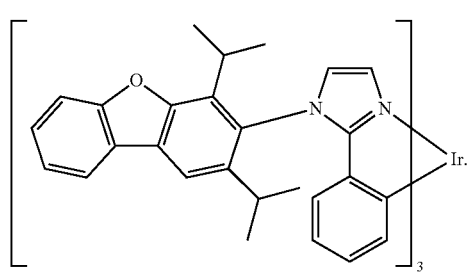

Compound 1

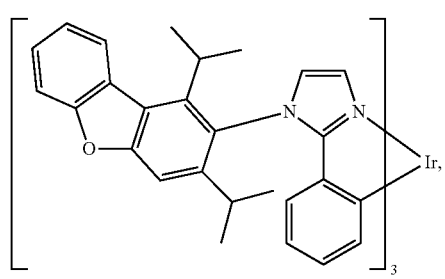

Compound 2

-continued
Compound 3
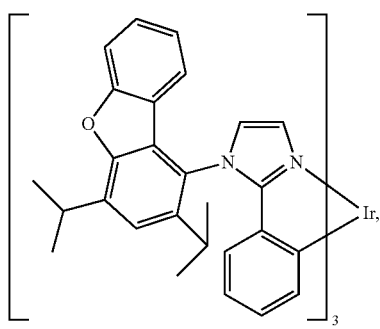
Compound 4
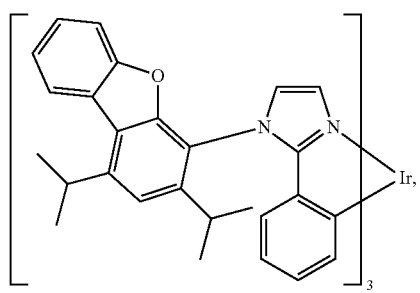
Compound 5
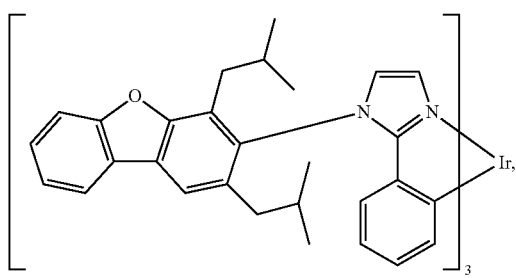
Compound 6
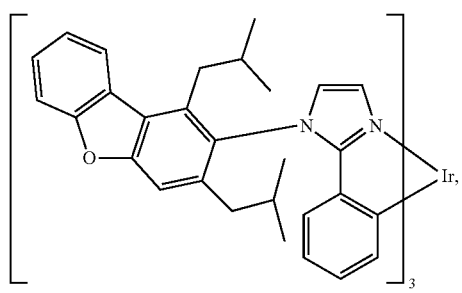
Compound 7
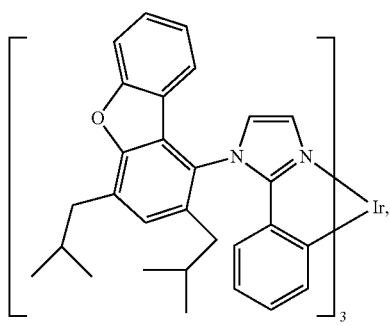
Compound 8
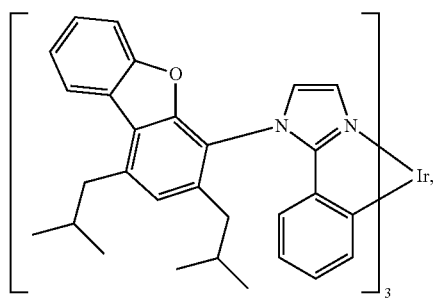
Compound 9
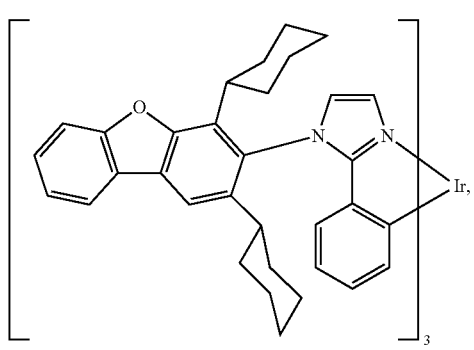
Compound 10
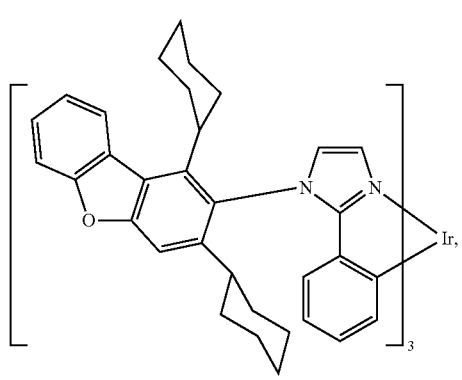

-continued
Compound 11
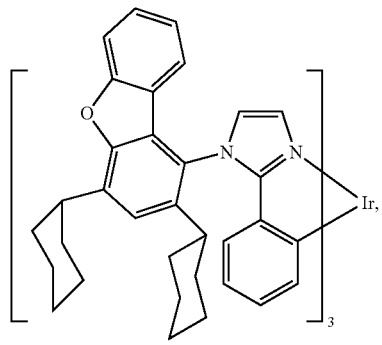
Compound 12
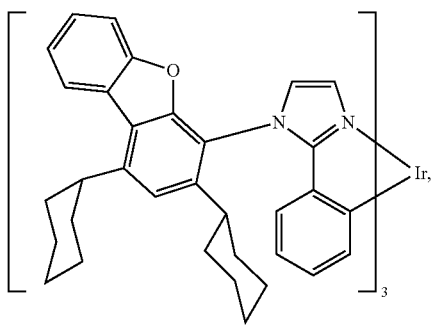
Compound 13
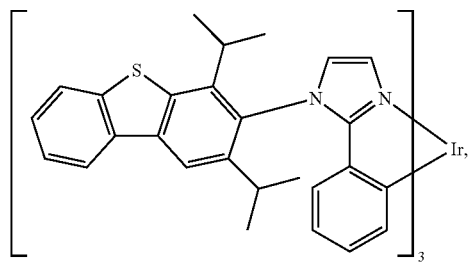
Compound 14
Compound 15
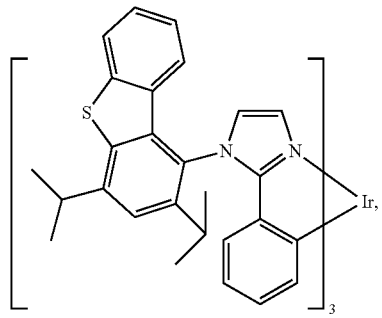
Compound 16
Compound 17
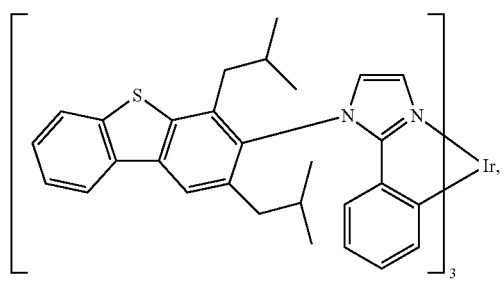
Compound 18
Compound 19
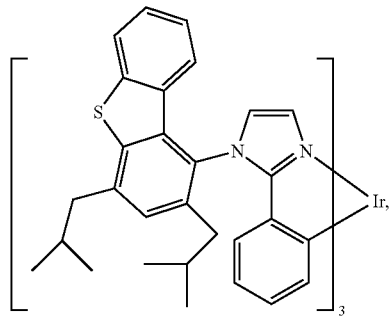
Compound 20
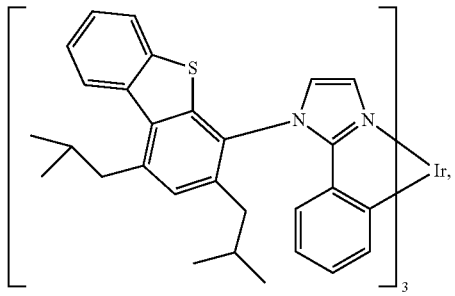

-continued
Compound 21
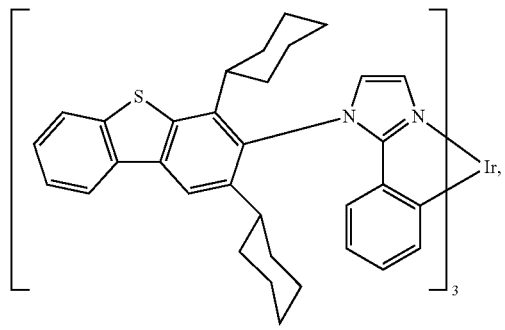
Compound 22
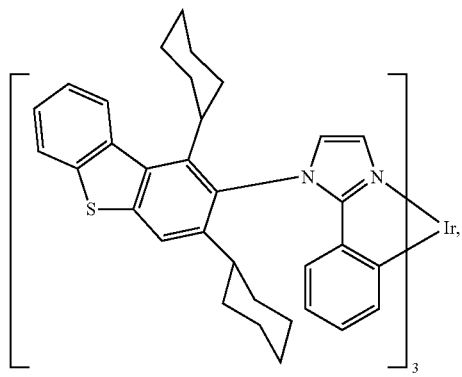
Compound 23
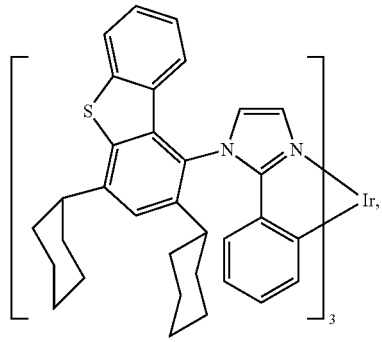
Compound 24
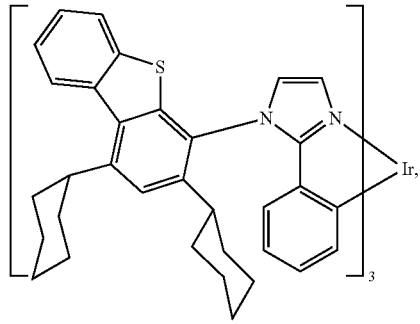
Compound 25
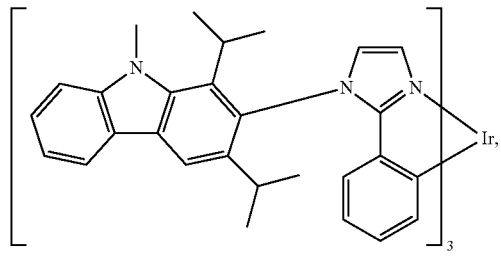
Compound 26
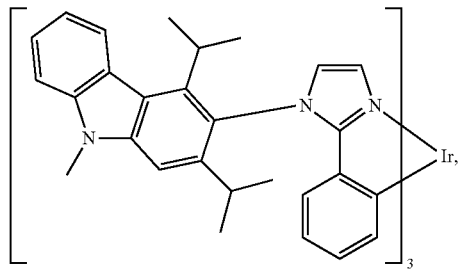
Compound 27
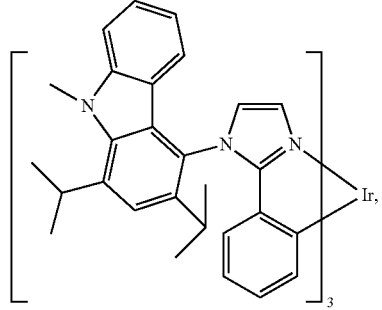
Compound 28
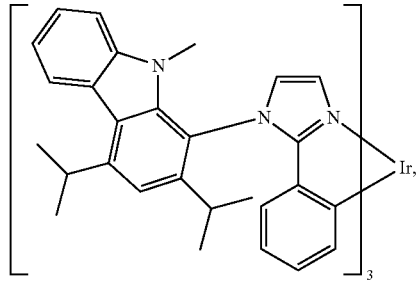

-continued
Compound 29
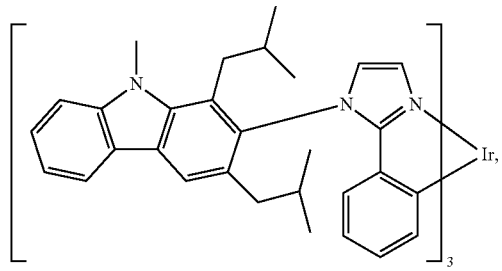
Compound 30
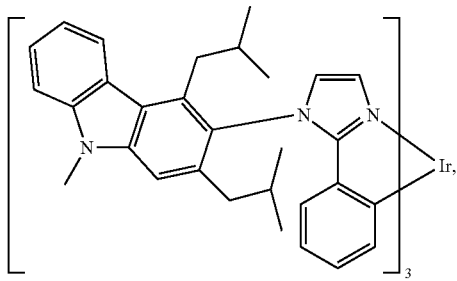
Compound 31
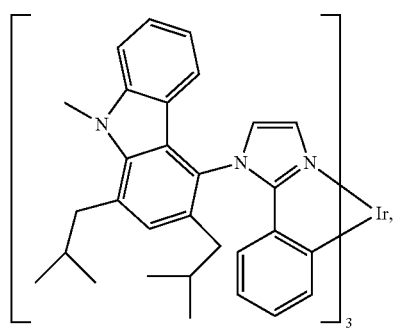
Compound 32
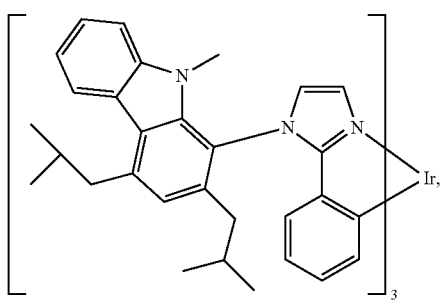
Compound 33
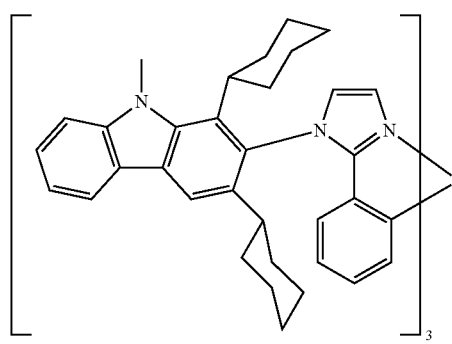
Compound 34
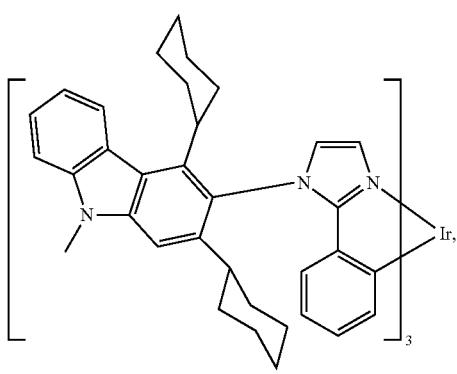
Compound 35
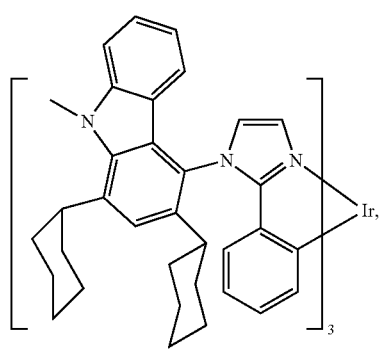
Compound 36
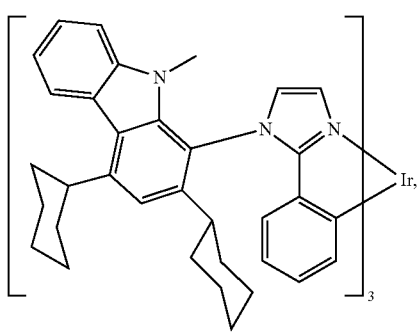
Compound 37
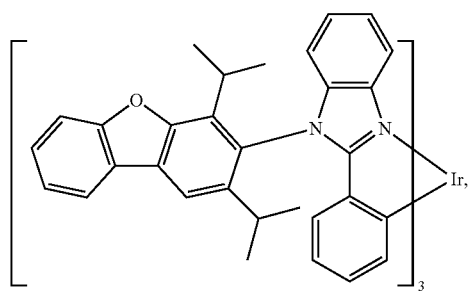
Compound 38
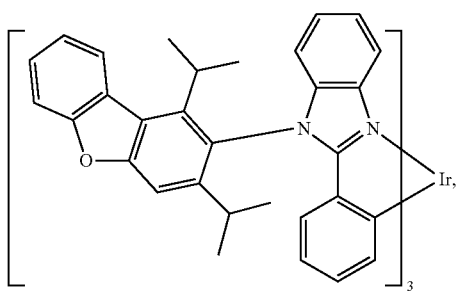

-continued
Compound 39
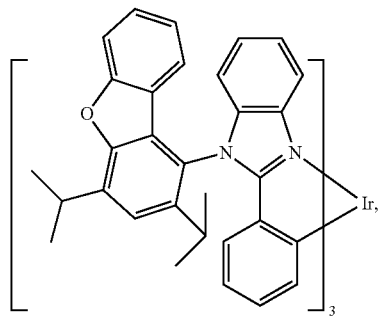
Compound 40
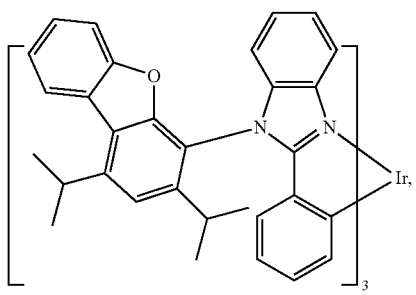
Compound 41
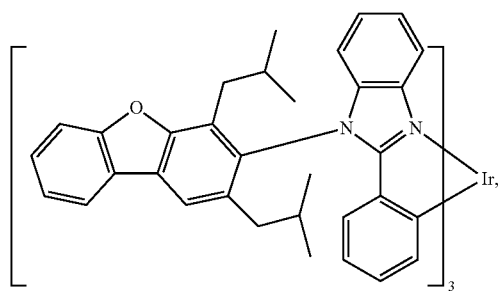
Compound 42
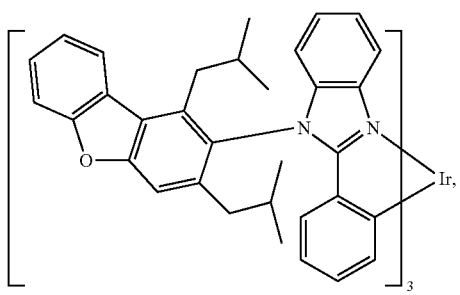
Compound 43
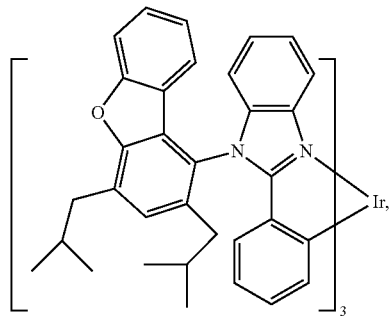
Compound 44
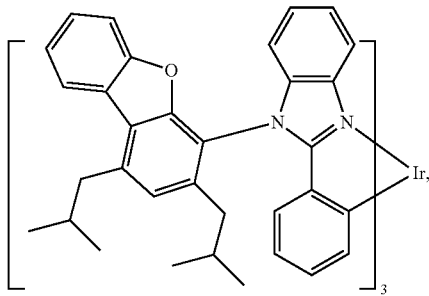
Compound 45
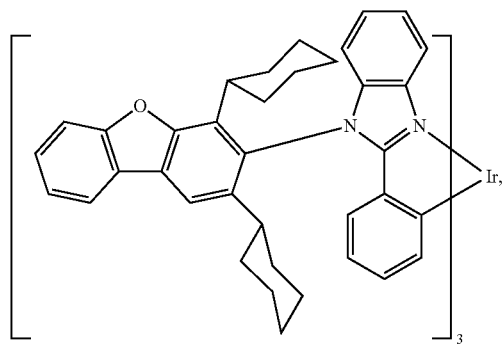
Compound 46
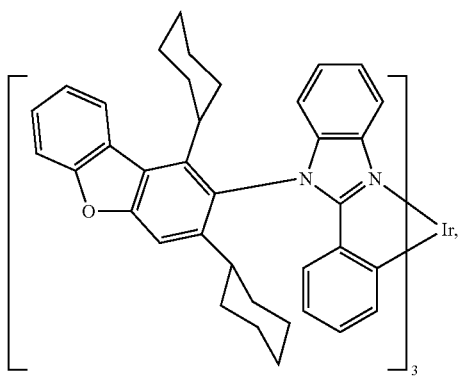

-continued
Compound 47
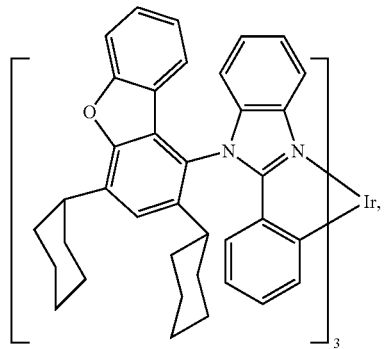
Compound 48
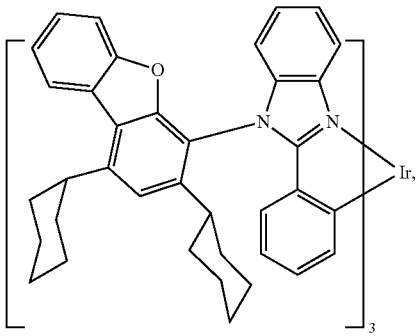
Compound 49
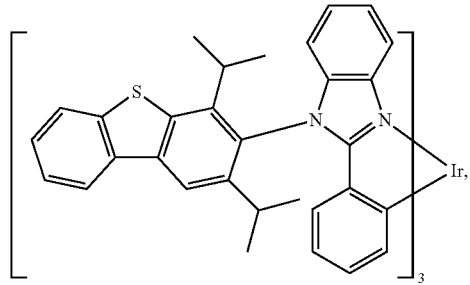
Compound 50
Compound 51
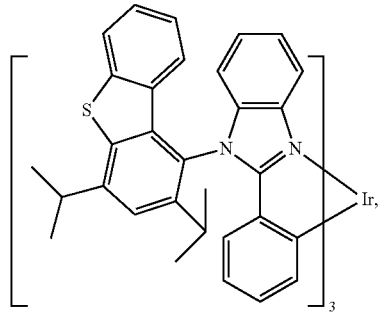
Compound 52
Compound 53
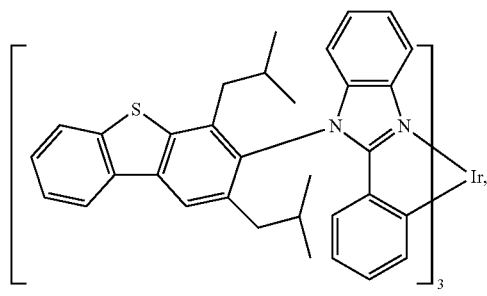
Compound 54
Compound 55
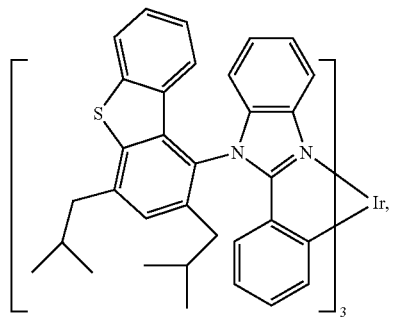
Compound 56
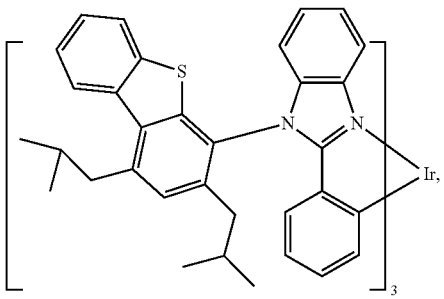

-continued
Compound 57
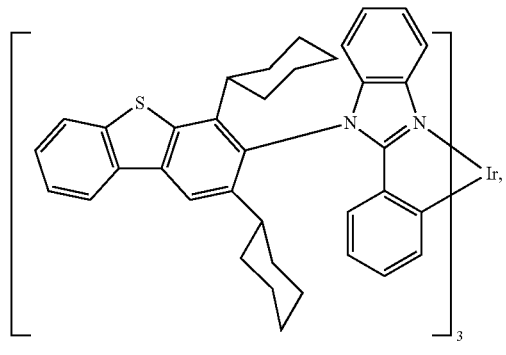
Compound 58
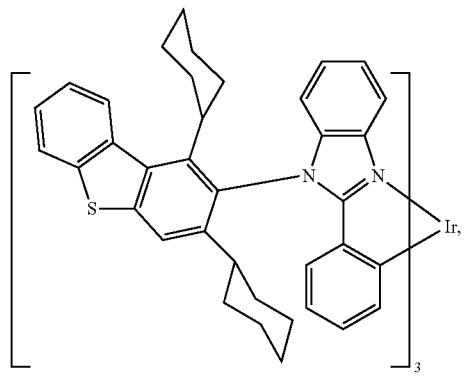
Compound 59
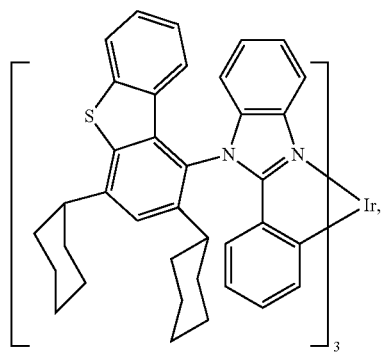
Compound 60
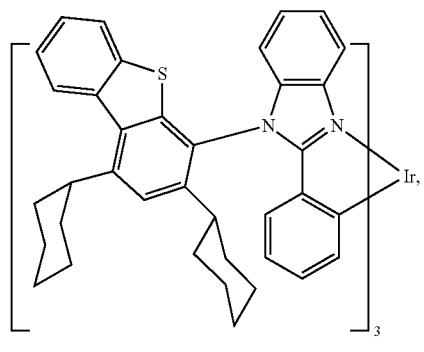
Compound 61
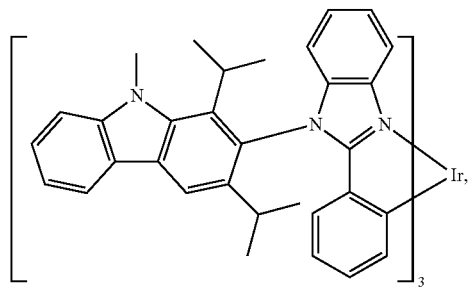
Compound 62
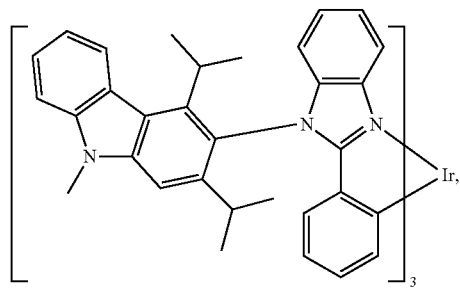
Compound 63
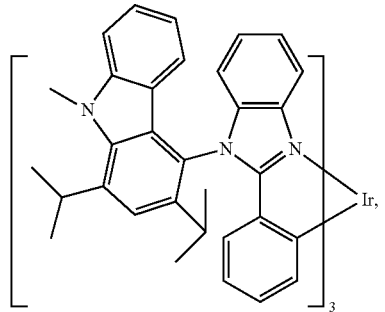
Compound 64
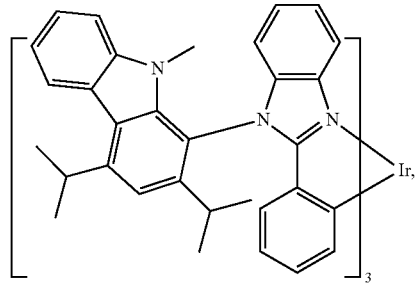

-continued
Compound 65
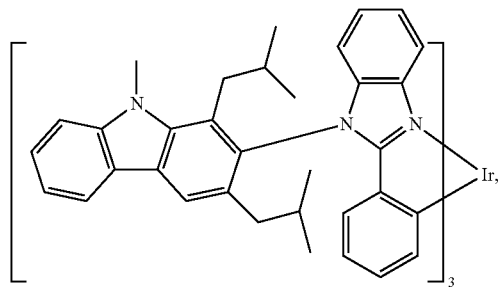
Compound 66
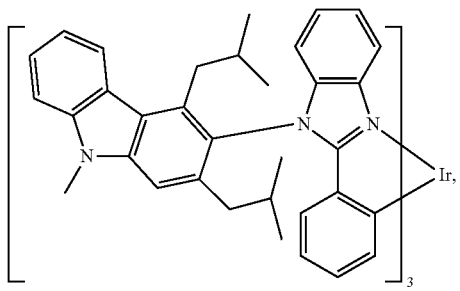
Compound 67
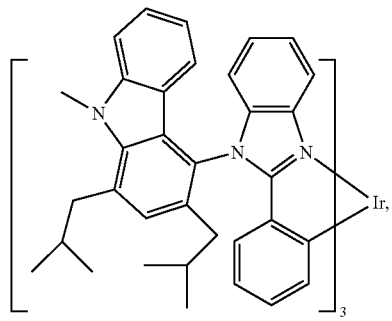
Compound 68
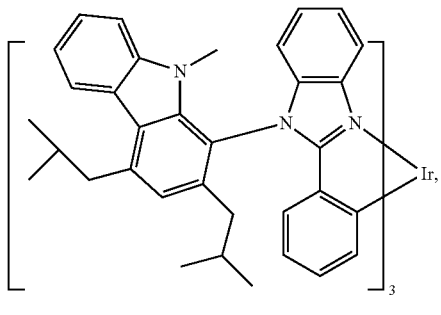
Compound 69
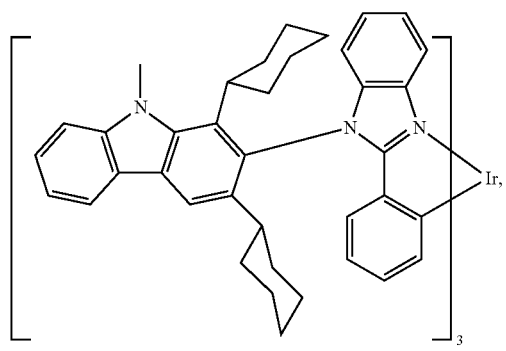
Compound 70
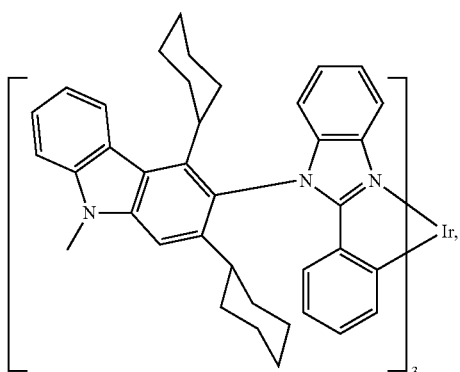
Compound 71
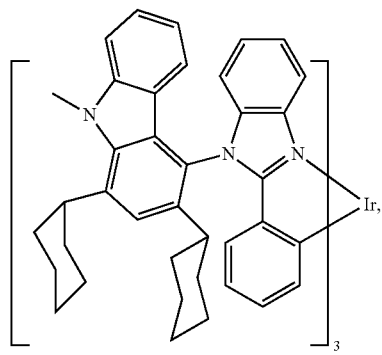
Compound 72
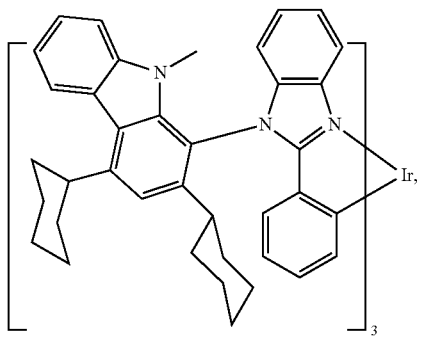
Compound 73
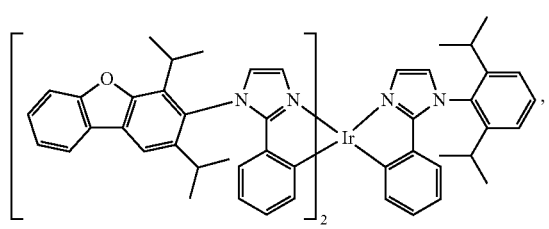
Compound 74
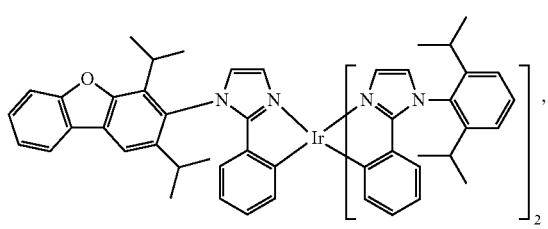

-continued
Compound 75
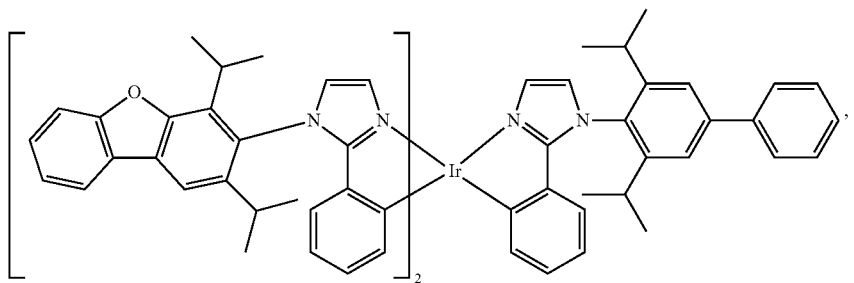
Compound 76
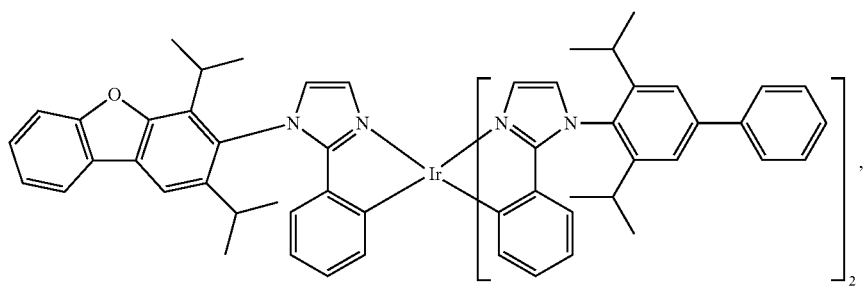
Compound 77
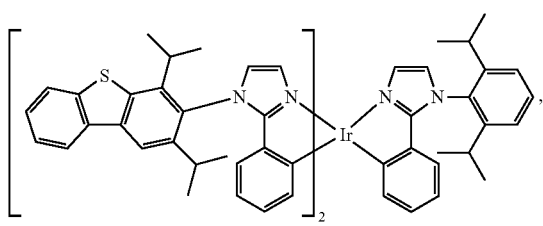
Compound 78
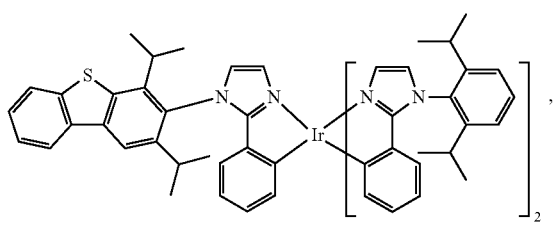
Compound 79
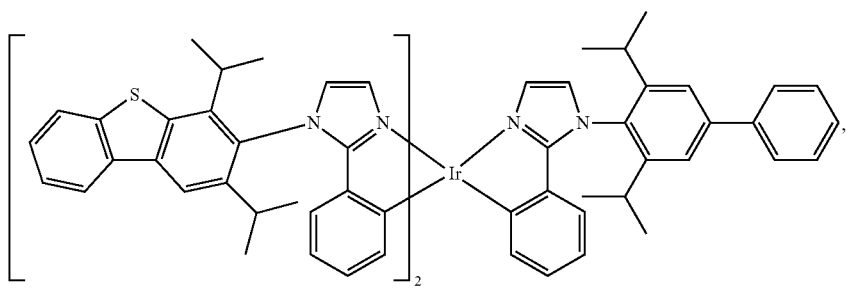
Compound 80
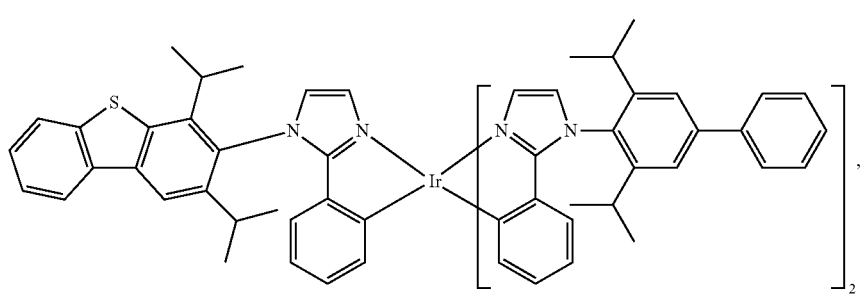

-continued
Compound 81
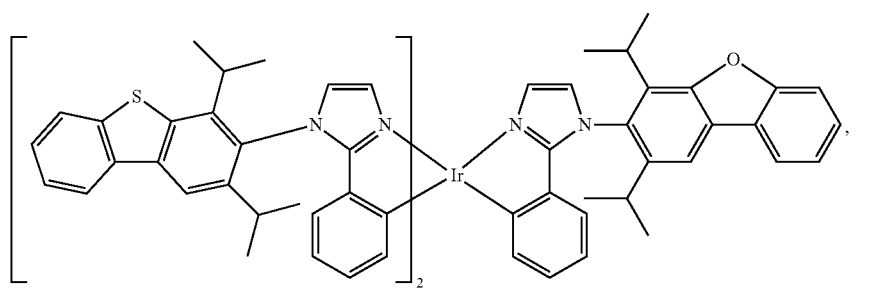
and
Compound 82
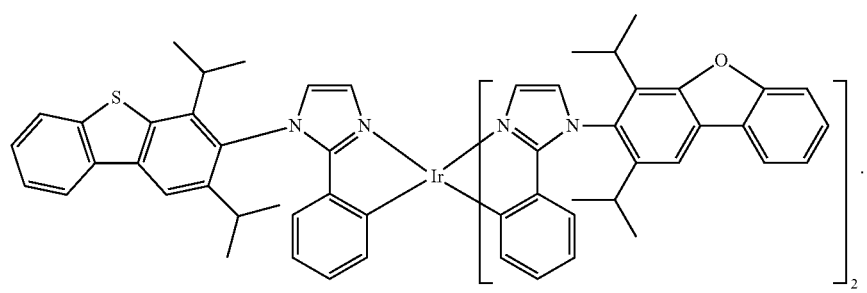
.
9. The compound of claim 1, wherein $R_A$ is fused to A.
10. The compound of claim 9, wherein the compound is selected from the group consisting of:
Compound 37
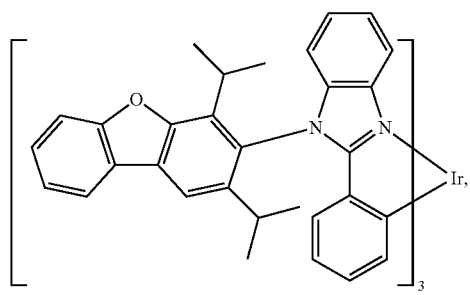
Compound 38
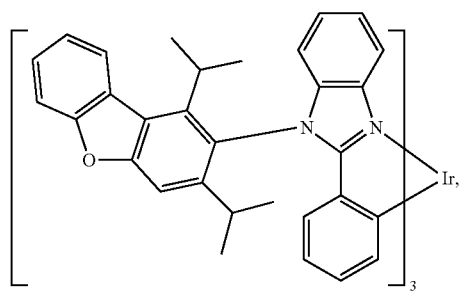
Compound 39
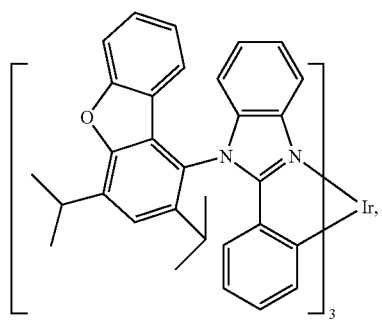
Compound 40
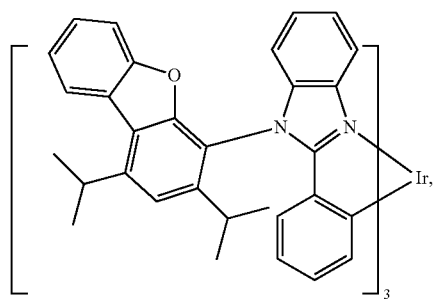

-continued
Compound 41
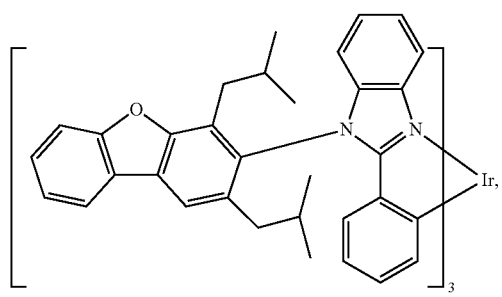
Compound 42
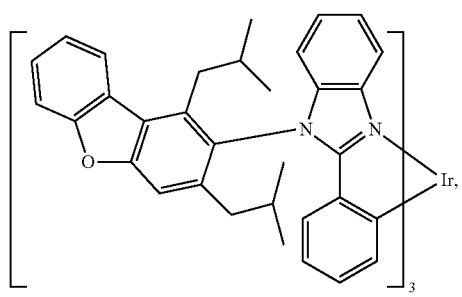
Compound 43
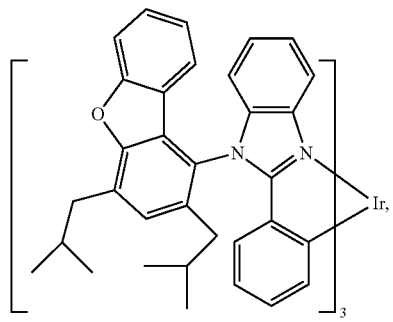
Compound 44
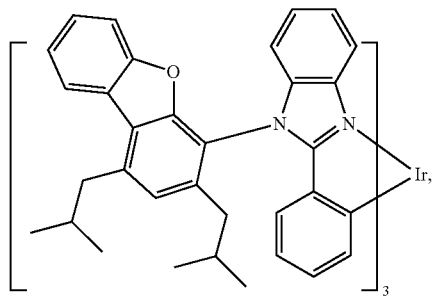
Compound 45
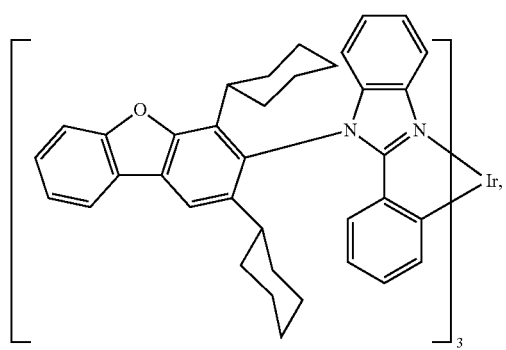
Compound 46
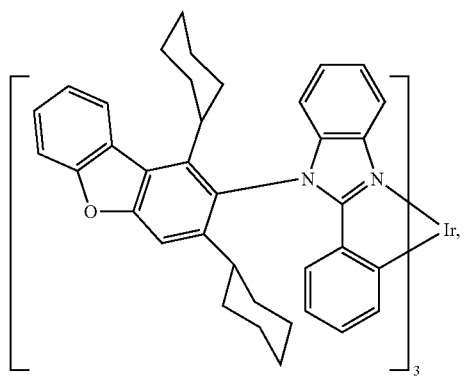
Compound 47
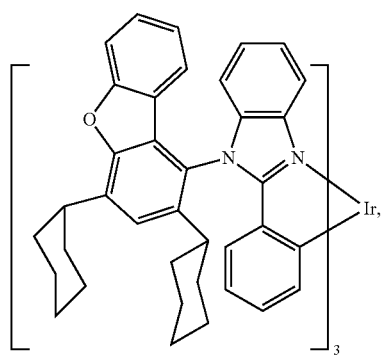
Compound 48
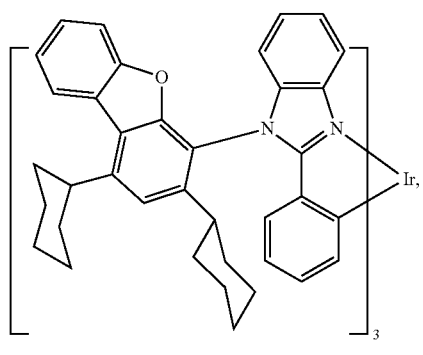

-continued
Compound 49
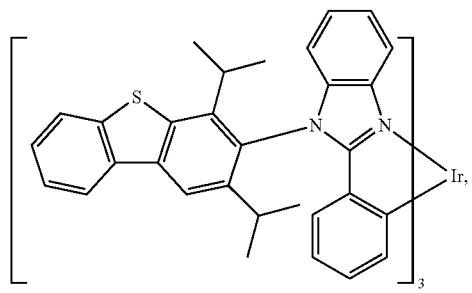
Compound 50
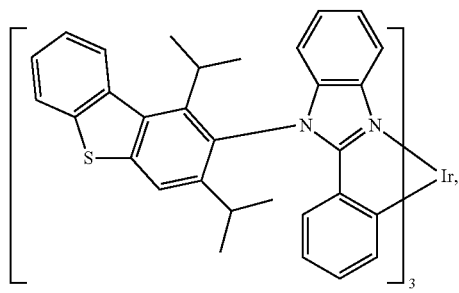
Compound 51
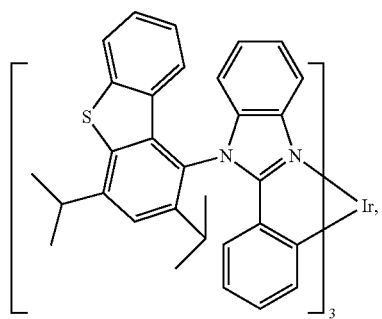
Compound 52
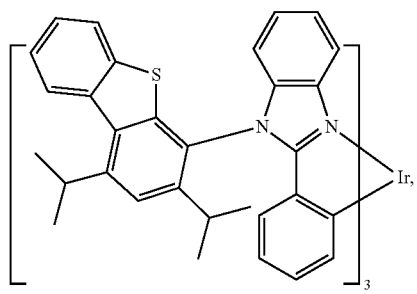
Compound 53
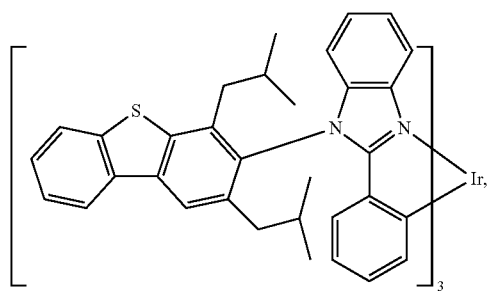
Compound 54
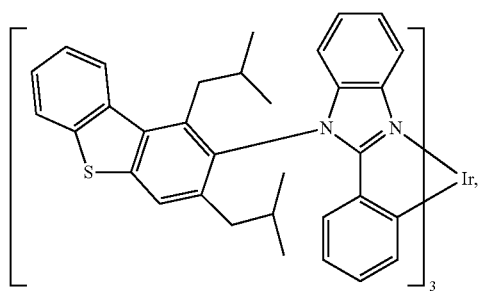
Compound 55
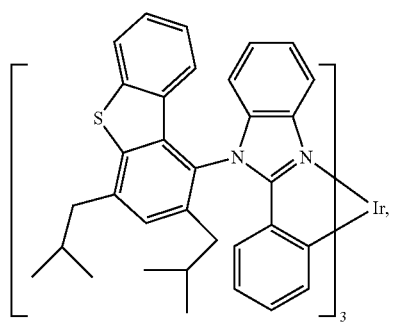
Compound 56
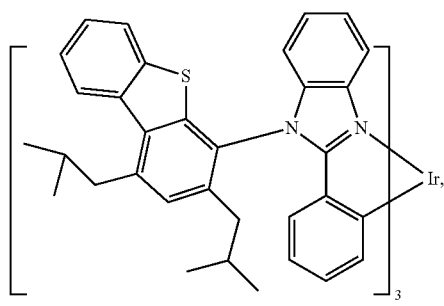
Compound 57
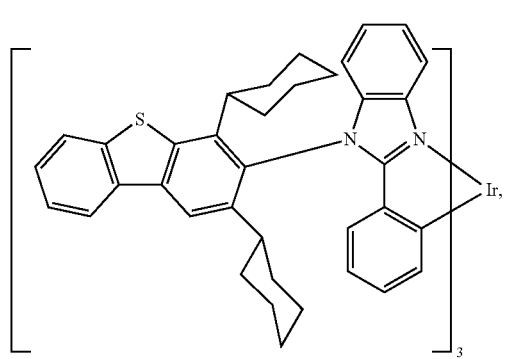
Compound 58
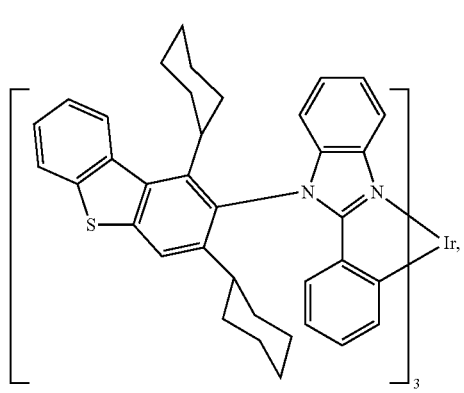

-continued
Compound 59
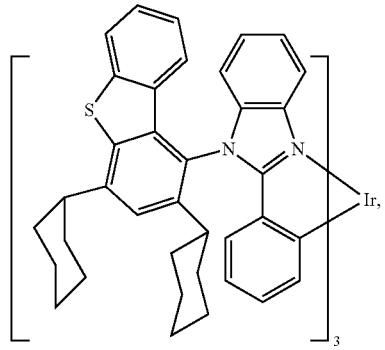
Compound 60
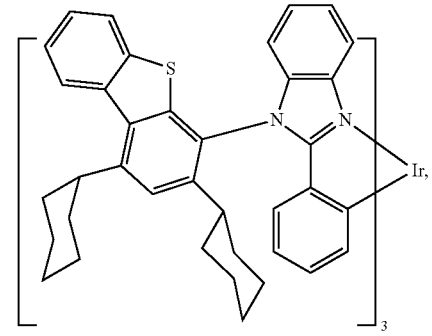
Compound 61
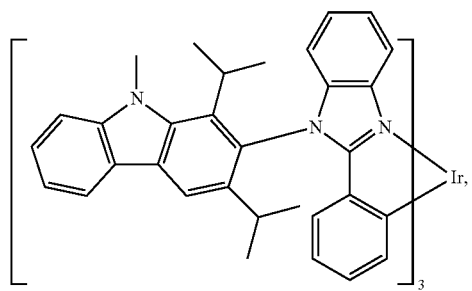
Compound 62
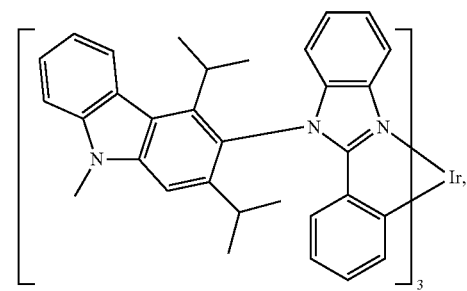
Compound 63
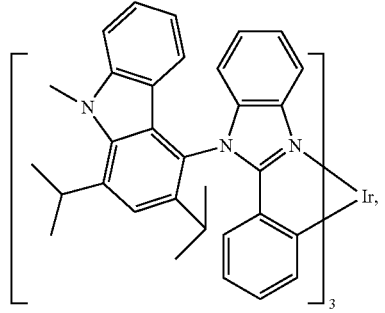
Compound 64
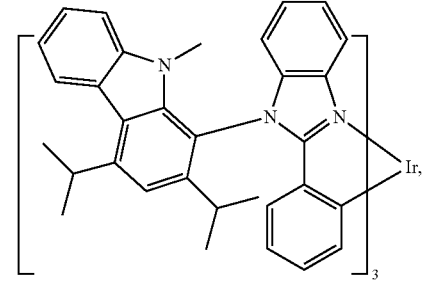
Compound 65
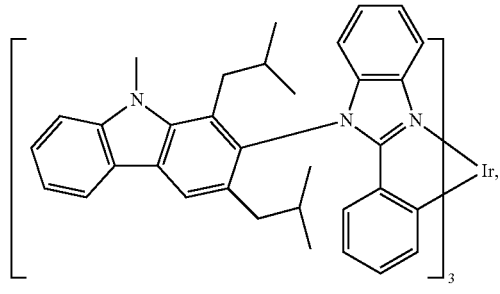
Compound 66
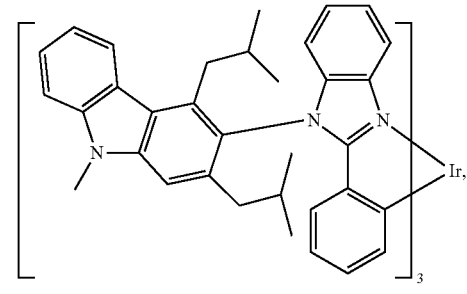
Compound 67
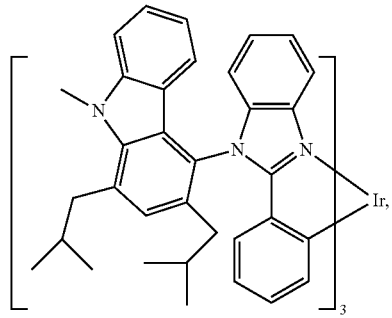
Compound 68
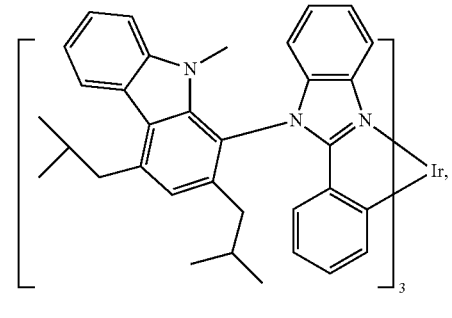

-continued
Compound 69
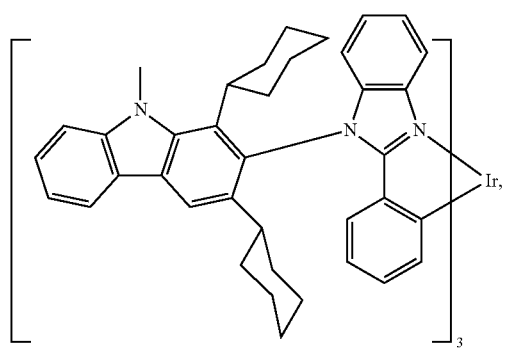
Compound 70
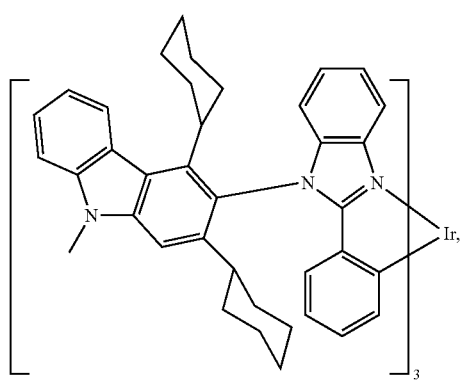
Compound 71
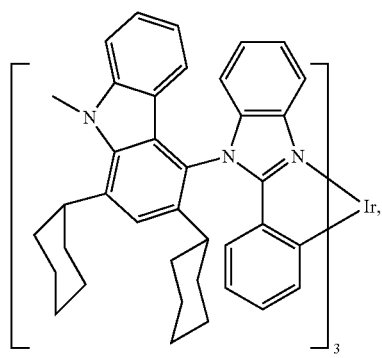
and
Compound 72
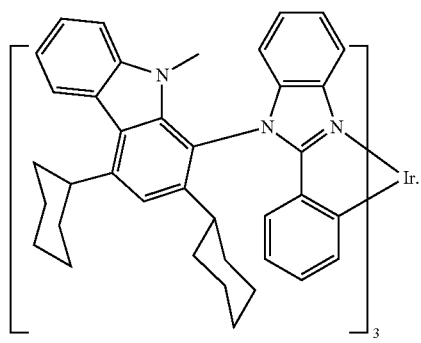
11. The compound of claim 1, wherein X is O.
12. The compound of claim 11, wherein the compound is selected from the group consisting of:
Compound 1
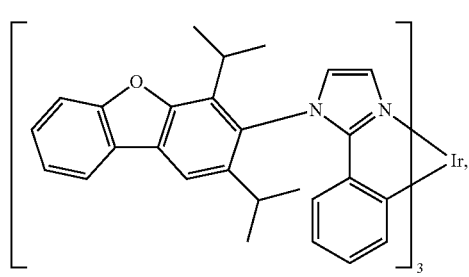
Compound 2
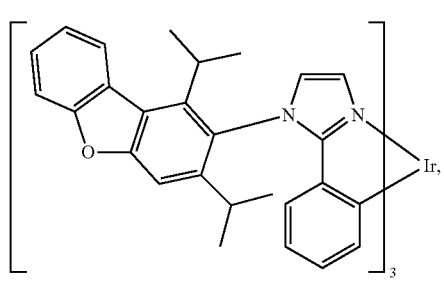
Compound 3
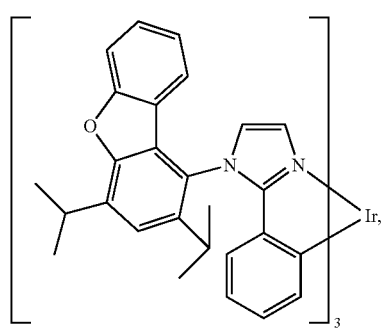
Compound 4
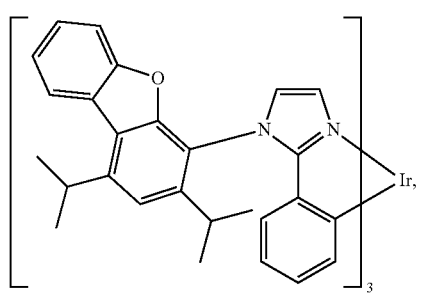

-continued
Compound 5
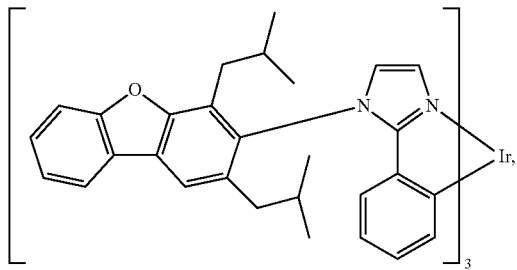
Compound 6
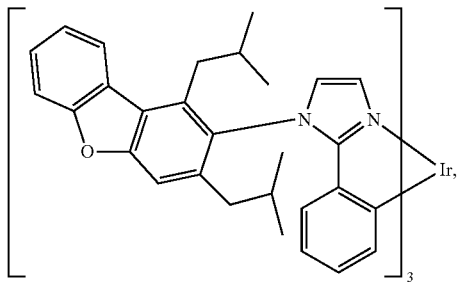
Compound 7
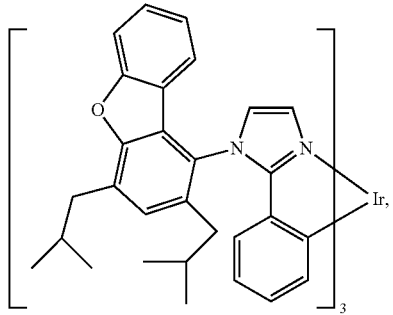
Compound 8
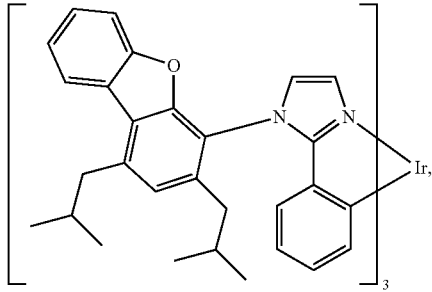
Compound 9
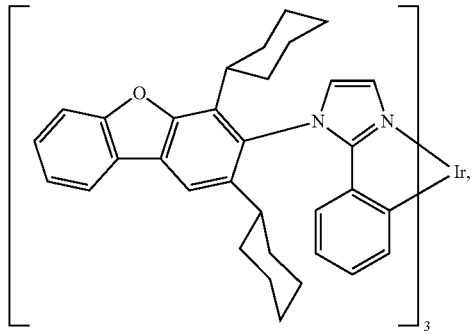
Compound 10
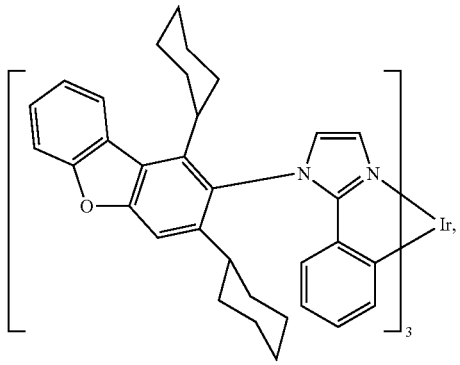
Compound 11
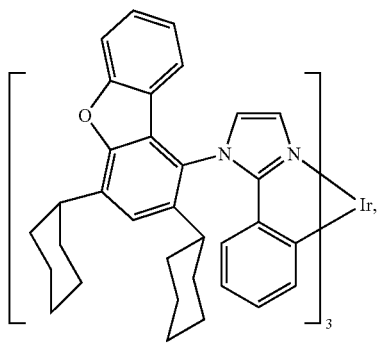
Compound 12
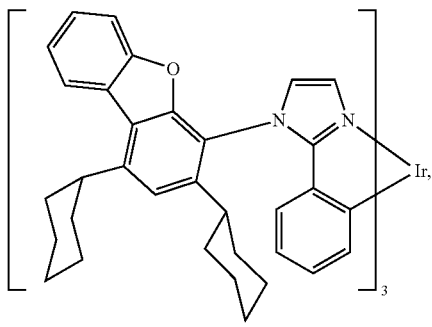
Compound 37
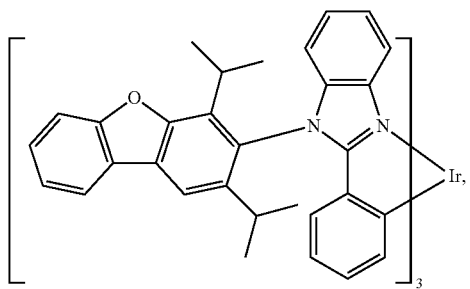
Compound 38
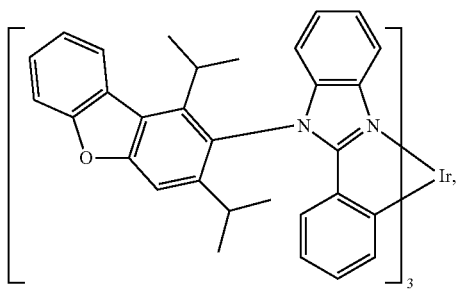

-continued
Compound 39
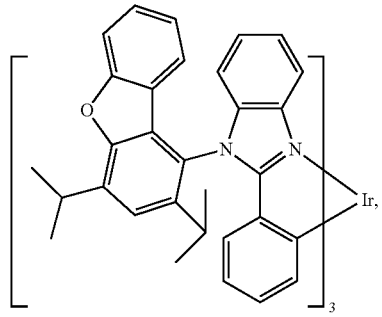
Compound 40
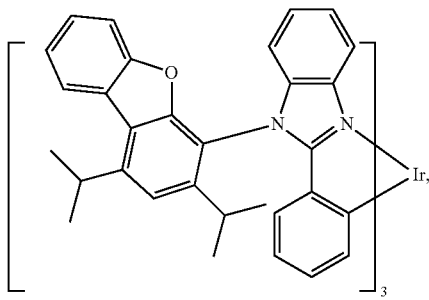
Compound 41
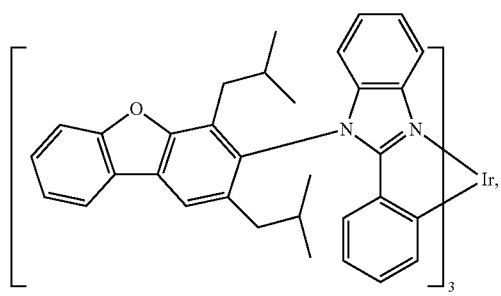
Compound 42
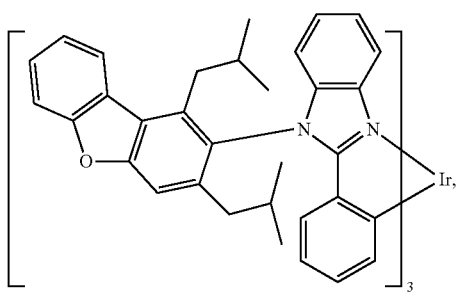
Compound 43
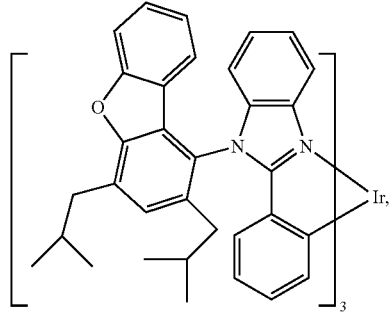
Compound 44
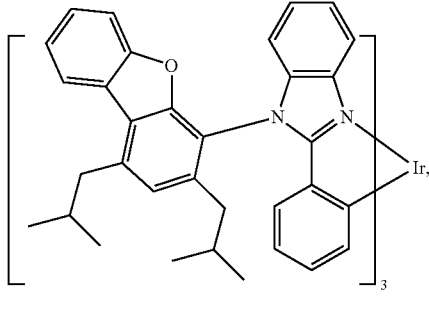
Compound 45
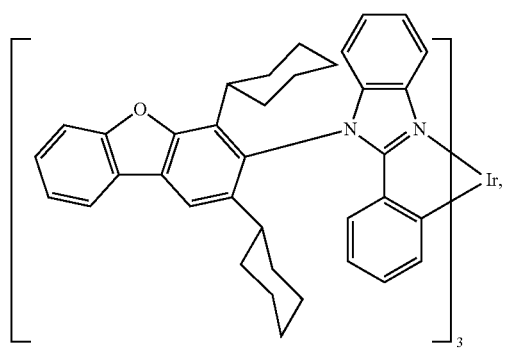
Compound 46
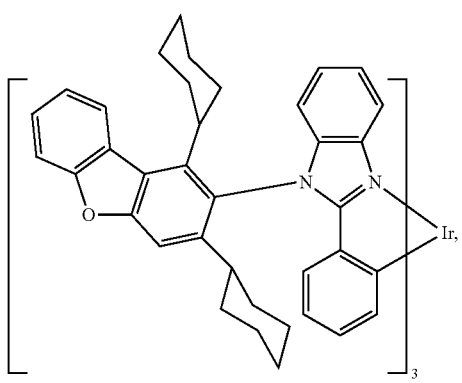

-continued
Compound 47
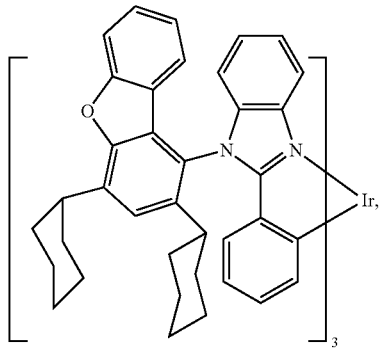
and
Compound 48
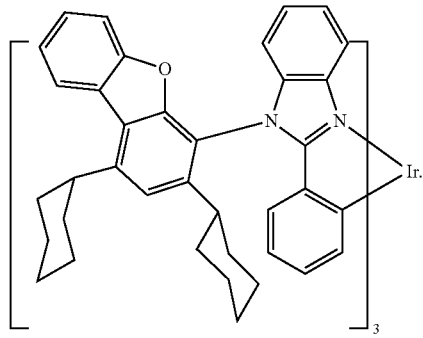
13. The compound of claim 1, wherein X is S.
14. The compound of claim 13, wherein the compound is selected from the group consisting of:
Compound 13
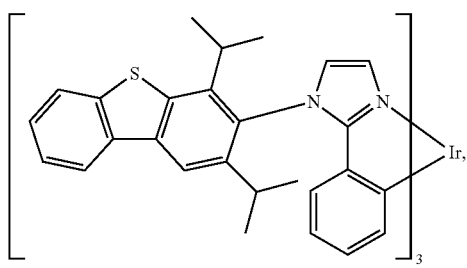
Compound 14
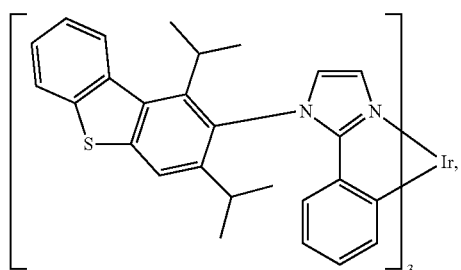
Compound 15
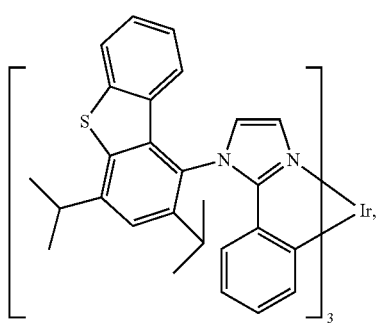
Compound 16
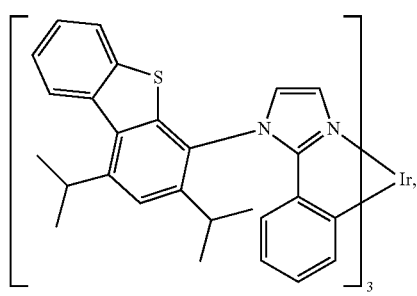
Compound 17
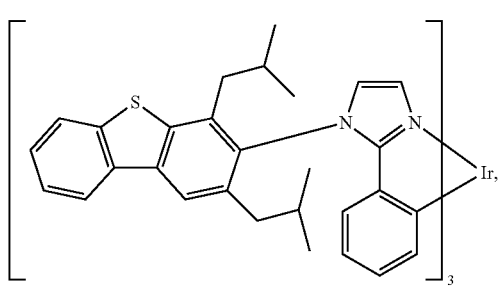
Compound 18
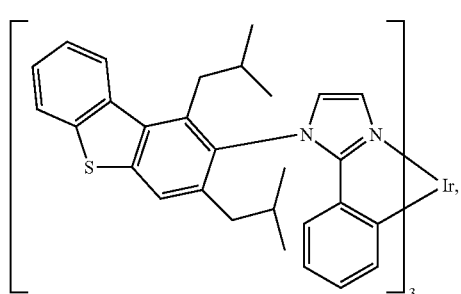

-continued
Compound 19
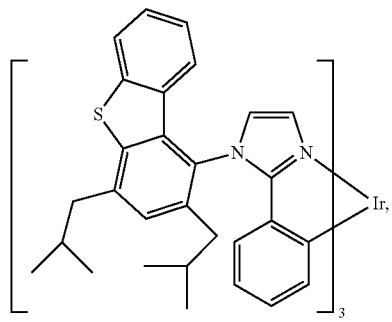
Compound 20
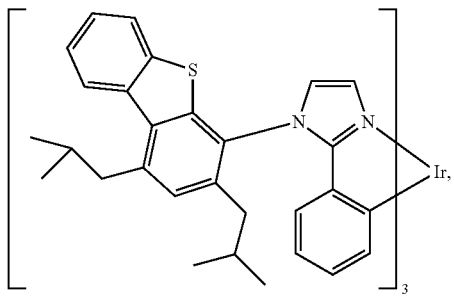
Compound 21
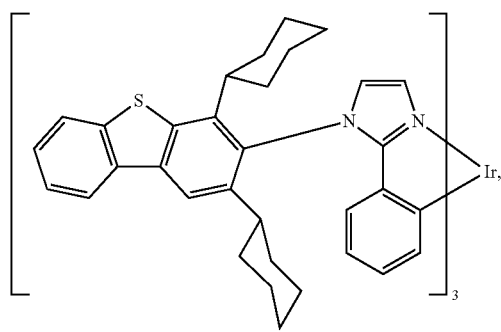
Compound 22
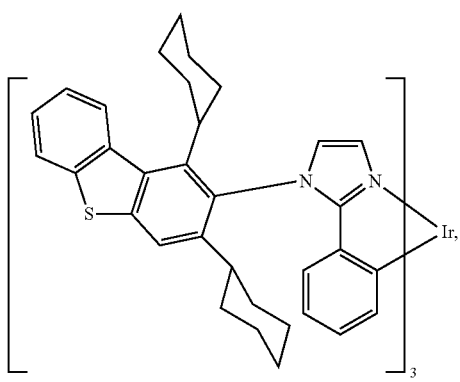
Compound 23
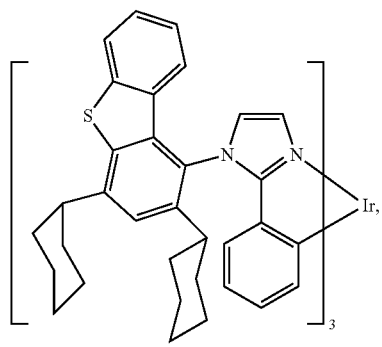
Compound 24
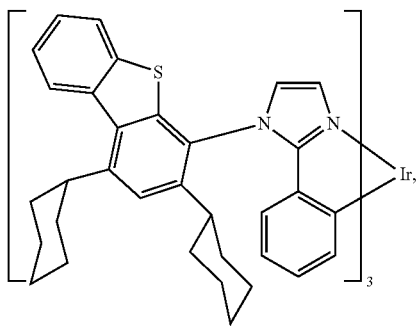
Compound 49
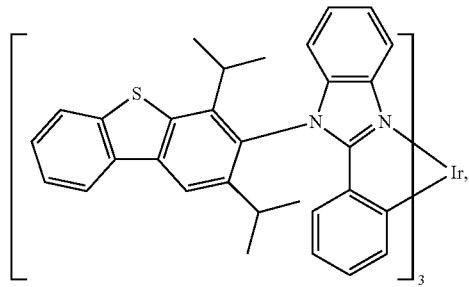
Compound 50
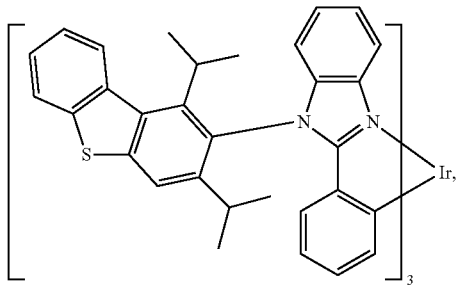

-continued
Compound 51
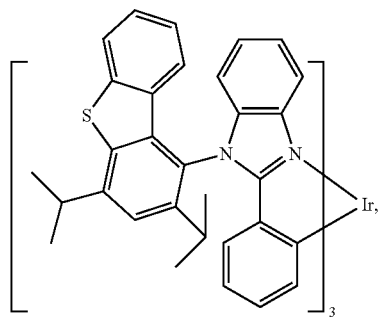
Compound 52
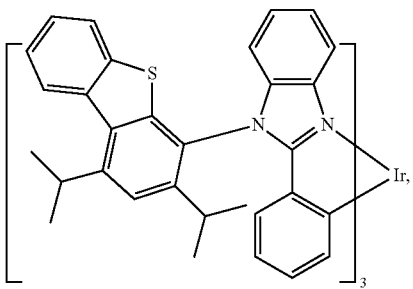
Compound 53
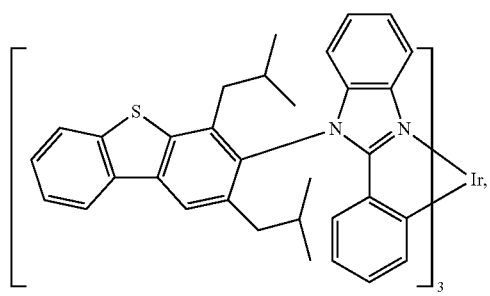
Compound 54
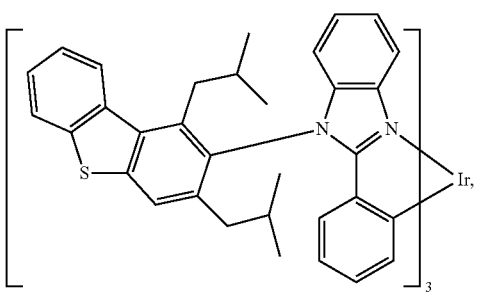
Compound 55
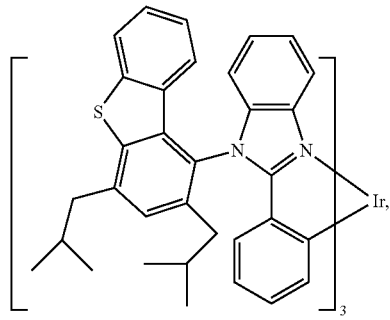
Compound 56
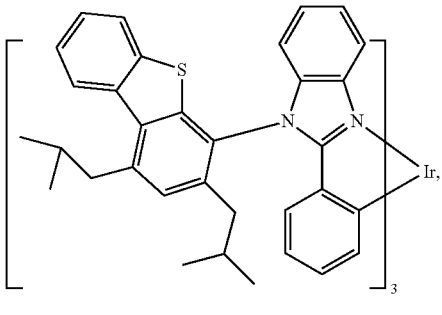
Compound 57
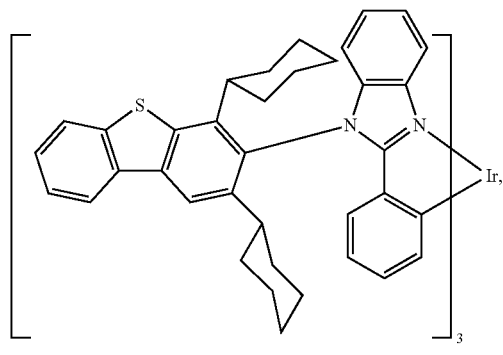
Compound 58
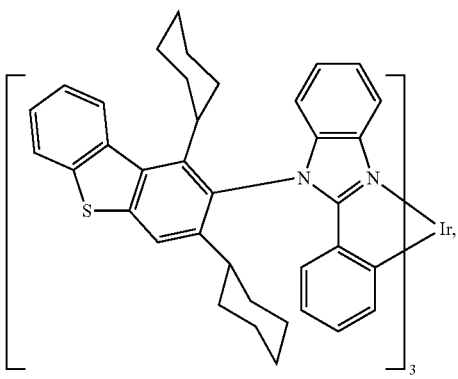

-continued
Compound 58
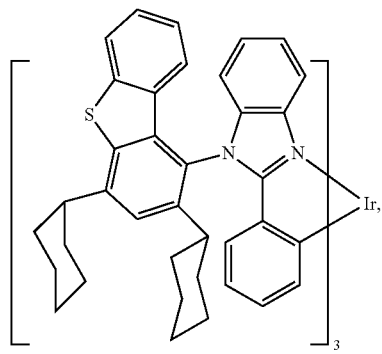
and
Compound 60
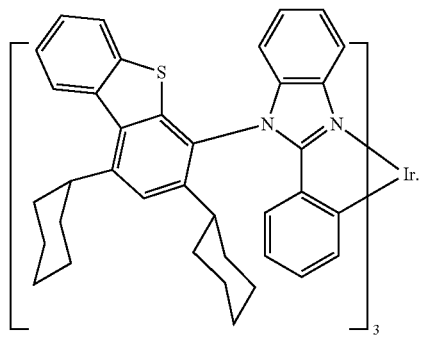
15. The compound of claim 1, wherein X is NR.
16. The compound of claim 1, wherein the compound is selected from the group consisting of:
Compound 25
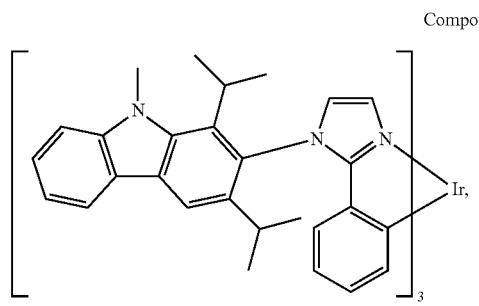
-continued
Compound 28
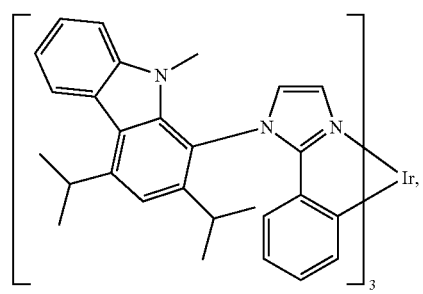
Compound 26
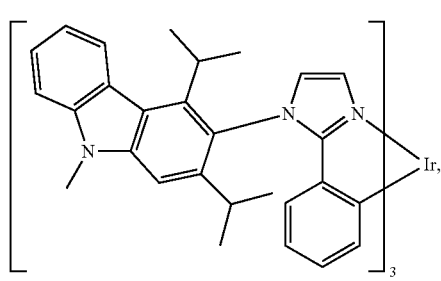
Compound 29
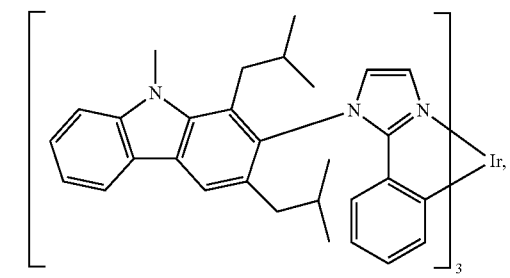
Compound 27
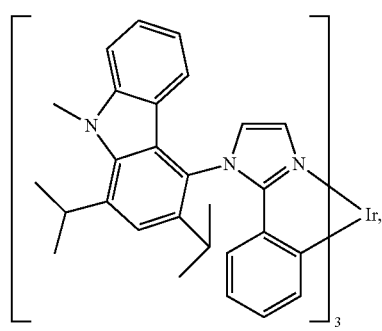
Compound 30
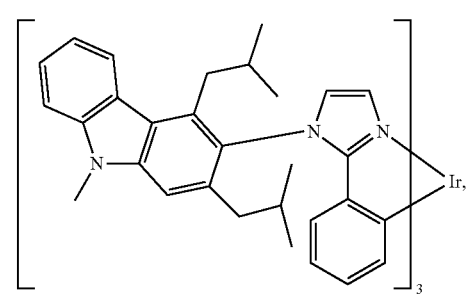

Compound 31
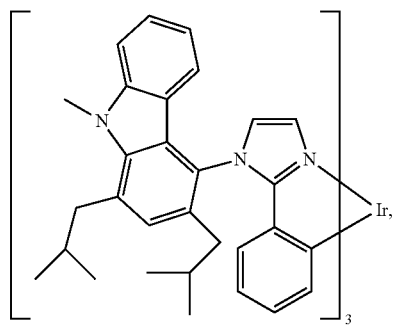
Compound 32
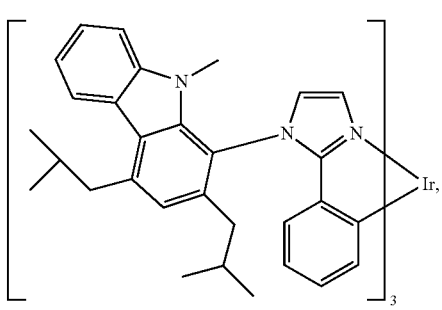
Compound 33
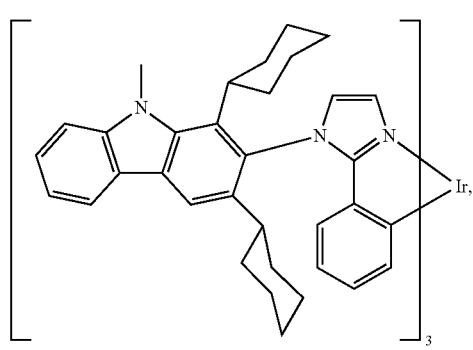
Compound 34
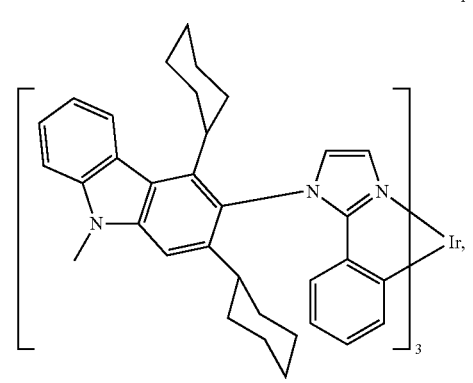
Compound 35
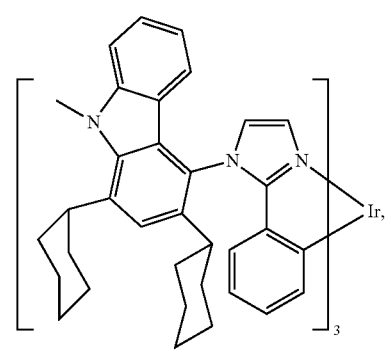
Compound 36
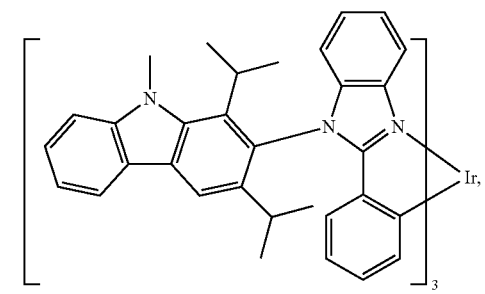
Compound 61
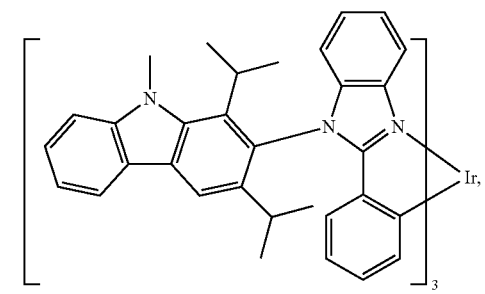
Compound 62
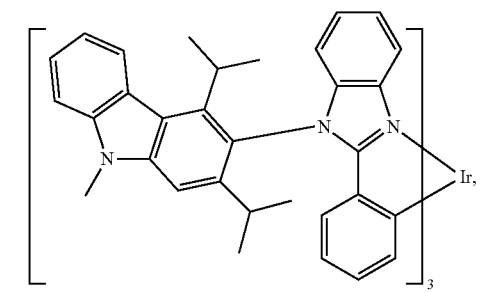
Compound 63
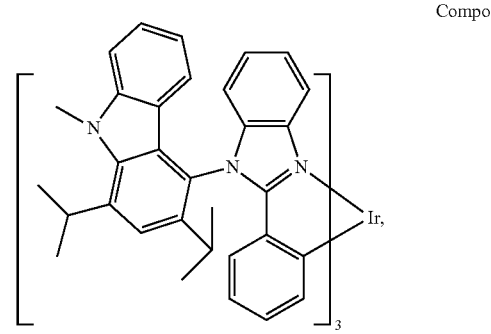

Compound 64
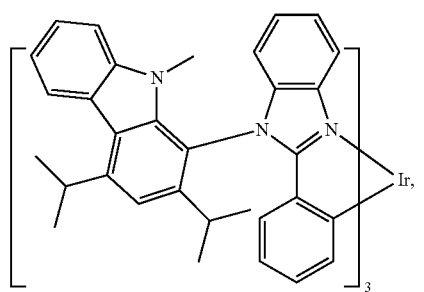
Compound 65
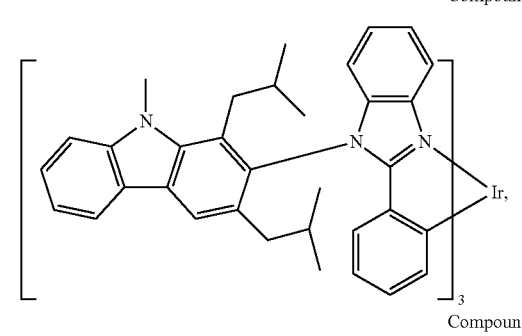
Compound 66
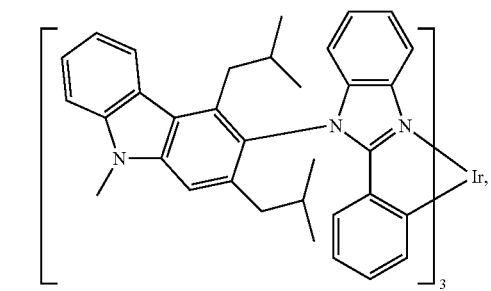
Compound 67
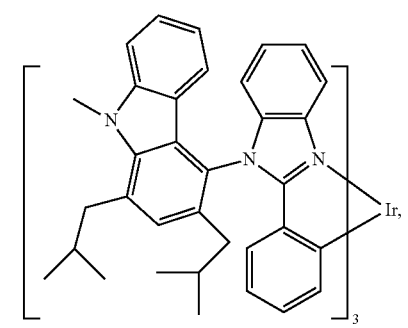
Compound 68
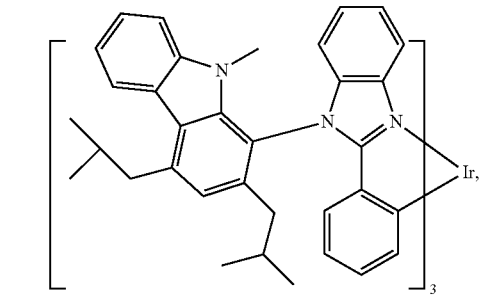
Compound 69
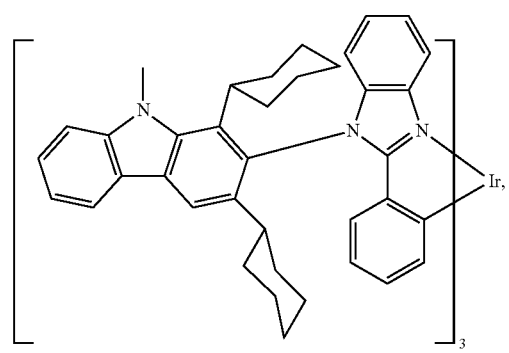
Compound 70
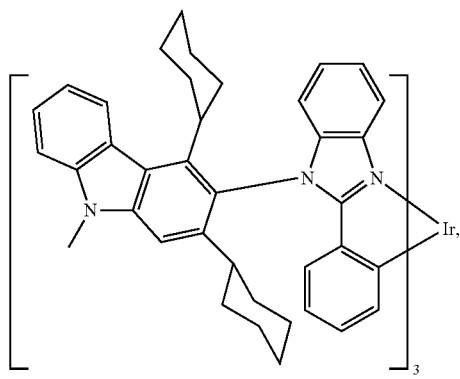
Compound 71
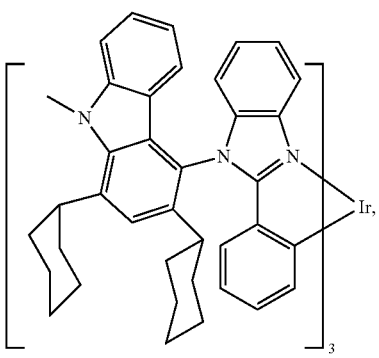
and
Compound 72
17. A first device comprising an organic light emitting device, comprising:
 an anode;
 a cathode; and an organic layer, disposed between the anode and the cathode, the organic layer comprising a compound comprising a ligand L having the formula:

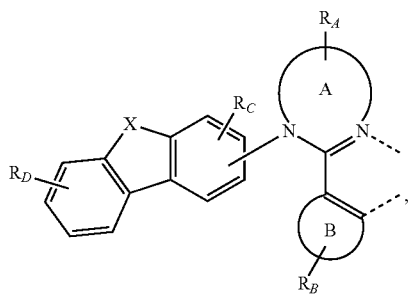

Formula I wherein A is a 5-membered heterocyclic ring;
wherein B is a 6-membered carbocyclic ring;
wherein $R_B$ and $R_D$ represent mono, di, tri, or tetra substitutions;
wherein $R_A$ represents mono or di substitution;
wherein $R_A$, $R_B$, and $R_D$ are independently selected from hydrogen, halogen, alkyl, alkoxy, amino, alkenyl, alkynyl, aryl and heteroaryl;
wherein $R_A$, $R_B$, and $R_D$ are optionally fused;
wherein X is selected from the group consisting of NR, O, and S;
wherein R is aryl or alkyl;
wherein $R_C$ represents two identical substituents with the two substituents having a meta relationship to each other;
wherein at least one $R_C$ is ortho to a carbon bonded to ring A;
wherein the $R_C$ substituents are selected from cyclic alkyl and branched alkyl;
wherein each $R_C$ has 3 or more carbon atoms; and
wherein the ligand L is coordinated to a metal M having an atomic number greater than 40.

18. The device of claim 17, wherein the first device is a consumer product.

19. The device of claim 17, wherein the organic layer is an emissive layer and the compound is an emitting dopant.

20. The device of claim 19, wherein the organic layer further comprises a host having the formula:

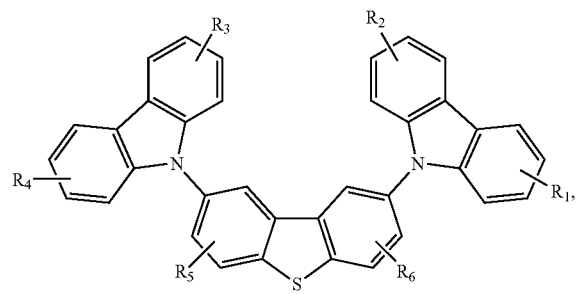

wherein $R_1$, $R_2$, $R_3$, $R_4$, $R_5$, and $R_6$ are independently selected from the group consisting of hydrogen, alkyl and aryl.

21. The compound of claim 1, wherein the compound is homoleptic.

* * * * *